US011287425B2

(12) United States Patent
Ward et al.

(10) Patent No.: US 11,287,425 B2
(45) Date of Patent: *Mar. 29, 2022

(54) GENETIC MARKERS ASSOCIATED WITH ENDOMETRIOSIS AND USE THEREOF

(75) Inventors: Kenneth Ward, Salt Lake City, UT (US); Hans Albertson, Salt Lake City, UT (US)

(73) Assignee: Juneau Biosciences, LLC, Salt Lake City, UT (US)

( * ) Notice: Subject to any disclaimer, the term of this patent is extended or adjusted under 35 U.S.C. 154(b) by 704 days.

This patent is subject to a terminal disclaimer.

(21) Appl. No.: 12/765,643

(22) Filed: Apr. 22, 2010

(65) Prior Publication Data

US 2010/0272713 A1 Oct. 28, 2010

Related U.S. Application Data

(60) Provisional application No. 61/171,717, filed on Apr. 22, 2009, provisional application No. 61/245,808, filed on Sep. 25, 2009.

(51) Int. Cl.
  *G01N 33/569* (2006.01)
  *G01N 33/68* (2006.01)
  *C12Q 1/6883* (2018.01)

(52) U.S. Cl.
  CPC ..... *G01N 33/56905* (2013.01); *C12Q 1/6883* (2013.01); *G01N 33/6893* (2013.01); *C12Q 2600/106* (2013.01); *C12Q 2600/156* (2013.01); *C12Q 2600/158* (2013.01); *C12Q 2600/172* (2013.01); *G01N 2333/445* (2013.01)

(58) Field of Classification Search
  None
  See application file for complete search history.

(56) References Cited

U.S. PATENT DOCUMENTS

| | | | |
|---|---|---|---|
| 6,525,187 B1 | 2/2003 | Shami et al. | 536/23.5 |
| 6,540,980 B1 | 4/2003 | Blumenthal et al. | 424/9.43 |
| 6,586,569 B1 | 7/2003 | Powitz et al. | 530/300 |
| 7,268,117 B2 | 9/2007 | Messer et al. | |
| 7,368,533 B2 | 5/2008 | Shami et al. | 530/350 |
| 7,399,598 B2 | 7/2008 | Yang et al. | 435/7.1 |
| 8,771,941 B2 | 7/2014 | Keefe | |
| 8,932,993 B1 | 1/2015 | Ward et al. | |
| 9,434,991 B2 | 9/2016 | Ward et al. | |
| 9,840,738 B2 | 12/2017 | Ward et al. | |
| 2002/0127555 A1 | 9/2002 | Baban et al. | 435/6 |
| 2002/0147155 A1 | 10/2002 | Foster et al. | 514/23 |
| 2002/0192647 A1 | 12/2002 | Smith | 435/6 |
| 2003/0077589 A1 | 4/2003 | Hess et al. | 435/6 |
| 2003/0109018 A1 | 6/2003 | Starzinski et al. | 435/195 |
| 2003/0124551 A1* | 7/2003 | Pappa | C07K 14/47 435/6.17 |
| 2003/0166014 A1 | 9/2003 | Timms | 435/7.2 |
| 2003/0219835 A1 | 11/2003 | Gosselin et al. | 435/7.2 |
| 2004/0048919 A1 | 3/2004 | Dreon et al. | 514/458 |
| 2004/0052787 A1 | 3/2004 | King et al. | 424/144.1 |
| 2004/0091912 A1 | 5/2004 | Smith | 435/6 |
| 2004/0210400 A1 | 10/2004 | Konvicka | |
| 2005/0085453 A1 | 4/2005 | Govindarajan et al. | |
| 2005/0112570 A1* | 5/2005 | Bougneres | 435/6 |
| 2005/0142580 A1 | 6/2005 | Tay et al. | 435/6 |
| 2005/0130182 A1 | 7/2005 | Messer et al. | 435/6 |
| 2005/0214836 A1 | 9/2005 | Nakamura et al. | 435/6 |
| 2006/0014166 A1 | 1/2006 | Cohen et al. | 435/6 |
| 2006/0057584 A1 | 3/2006 | Baban et al. | 435/6 |
| 2007/0015160 A1 | 1/2007 | Kuroda et al. | 435/6 |
| 2007/0087386 A1 | 4/2007 | Yang et al. | 435/7.1 |
| 2007/0092484 A1 | 4/2007 | Levine et al. | 424/85.1 |
| 2007/0264270 A1 | 11/2007 | Barnhart et al. | 424/184.1 |
| 2007/0287676 A1 | 12/2007 | Guo et al. | 514/43 |
| 2008/0008650 A1 | 1/2008 | Fukuda et al. | 424/9.1 |
| 2008/0187527 A1 | 8/2008 | Powitz et al. | 424/130 |
| 2008/0241852 A1 | 10/2008 | Messer et al. | 435/7.1 |
| 2008/0305967 A1 | 12/2008 | Ward et al. | |
| 2008/0306034 A1 | 12/2008 | Ward | |
| 2008/0318237 A1 | 12/2008 | Giudice | 435/6 |
| 2009/0099789 A1 | 4/2009 | Stephan et al. | |
| 2011/0110946 A1 | 5/2011 | Gross et al. | |
| 2013/0005697 A1 | 1/2013 | Schwede et al. | |
| 2013/0022593 A1 | 1/2013 | Giudice | |
| 2015/0361494 A1 | 12/2015 | Ward et al. | |
| 2015/0363558 A1 | 12/2015 | Ward et al. | |

(Continued)

FOREIGN PATENT DOCUMENTS

| | | | |
|---|---|---|---|
| CA | 2329527 | 5/1999 | C12Q 1/68 |
| CA | 2399259 | 8/2001 | C12Q 1/68 |
| CA | 2497132 | 3/2004 | C12Q 1/68 |

(Continued)

OTHER PUBLICATIONS

Hegele. Arterioscler Thromb Vasc Biol. 2002; 22:1058-1061.*
Lucentini (2004) The Scientist. Dec. 20, 2004, p. 20.*
NCBI dbSNP record rs6675661 accessed from http://www.ncbi.nlm.nih.gov/projects/SNP/snp_ref.cgi?rs=6675661 on Feb. 15, 2013.*
NCBI dbSNP record rs860792 accessed from http://www.ncbi.nlm.nih.gov/projects/SNP/snp_ref.cgi?rs=860792 on Feb. 15, 2013.*
Sotos et al. Statistics Education Research Journal 2009, Nov. 8(2):33-55.*
Terwilliger and Hiekkalinna European Journal of Human Genetics (2006) 14, 426-437 published online Feb. 15, 2006.*
Zill et al.Molecular Psychiatry (2004) 9, 1030-1036.*

(Continued)

*Primary Examiner* — Amanda Haney
(74) *Attorney, Agent, or Firm* — Greenberg Traurig, LLP

(57) ABSTRACT

The present invention relates to novel genetic markers associated with endometriosis and risk of developing endometriosis, and methods and materials for determining whether a human subject has endometriosis or is at risk of developing endometriosis and the use of such risk information in selectively administering a treatment that at least partially prevents or compensates for an endometriosis related symptom.

9 Claims, No Drawings

Specification includes a Sequence Listing.

(56) References Cited

U.S. PATENT DOCUMENTS

| | | | |
|---|---|---|---|
| 2016/0367568 A1 | 12/2016 | Ward et al. | |
| 2018/0245156 A1 | 8/2018 | Ward et al. | |

FOREIGN PATENT DOCUMENTS

| | | | |
|---|---|---|---|
| CA | 2596932 | 8/2006 | ............... C12Q 1/68 |
| CA | 2607341 | 11/2006 | ............... C12Q 1/68 |
| CA | 2681933 | 11/2007 | ............. G01N 33/68 |
| CA | 2676415 | 10/2008 | ............. C40B 40/06 |
| CN | 101334410 | 12/2008 | ............. G01N 33/68 |
| JP | 2009168646 | 7/2009 | ............. G01N 27/62 |
| WO | WO1999063079 | 12/1999 | ............... C12Q 1/68 |
| WO | WO-0007599 A1 | 2/2000 | |
| WO | WO2001032920 | 5/2001 | ............... C12Q 1/68 |
| WO | WO-0162959 A2 | 8/2001 | |
| WO | WO-0162959 A3 | 1/2003 | |
| WO | WO2004024952 | 3/2004 | ............... C12Q 1/68 |
| WO | WO2006091254 | 8/2006 | ............... C12Q 1/68 |
| WO | WO 2006/116873 | * 9/2006 | |
| WO | WO2006116873 | 11/2006 | ............... C12Q 1/68 |
| WO | WO-2007031277 A2 | 3/2007 | |
| WO | WO-2007031277 A3 | 6/2007 | |
| WO | WO2007126982 | 11/2007 | ............. G01N 33/68 |
| WO | WO2008049175 | 5/2008 | ............. G01N 33/68 |
| WO | WO2008103812 | 8/2008 | ........... C07K 14/745 |
| WO | WO 2008/123901 | * 10/2008 | |
| WO | WO2008123901 | 10/2008 | ............... C12Q 1/68 |
| WO | WO-2008154352 A2 | 12/2008 | |
| WO | WO2009068254 | 6/2009 | ............. G01N 33/68 |
| WO | WO-2009140126 A1 | 11/2009 | |
| WO | WO2010010951 | 1/2010 | ............... C12Q 1/68 |
| WO | WO-2010124101 A2 | 10/2010 | |
| WO | WO-2010124101 A3 | 5/2011 | |
| WO | WO-2012112883 A1 | 8/2012 | |
| WO | WO-2017015334 A1 | 1/2017 | |
| WO | WO-2018170325 A1 | 9/2018 | |

OTHER PUBLICATIONS

Langdahl (Journal of Bone and Mineral Research 2000 vol. 15, No. 3, pp. 402-414).*

Wall (Nature Reviews Genetics (2003) vol. 4, pp. 587-597).*

Andiappan (BMC Genetics. Nov. 2010 : 36).*

Nishida, Nao et al. BMC Genomics Sep. 22, 2008 9:431 pp. 9-10.*

Laufer (J Pediatr Adolesc Gynecol 2003 vol. 16 S3-S11).*

Setakis (Genome Research 2006 vol. 16 pp. 290-296).*

Mummidi et al. (Journal of Biological Chemistry 2000 vol. 275 No. 25 pp. 18946-18961).*

GenBank (dbSNP record for rs17265665 first added with build 123 on Oct. 28, 2004).*

Zheng (Nature Genetics Feb. 15, 2009 vol. 41 No. 3 pp. 324-328).*

U.S. Appl. No. 60/948,565, Belouchi et al, filed Jul. 9, 2007.

U.S. Appl. No. 60/899,615, Belouchi et al, filed Feb. 6, 2007.

U.S. Appl. No. 60/875,527, Goldman et al, filed Jun. 6, 2007.

U.S. Appl. No. 60/788,058, Goldman et al, filed Apr. 3, 2006.

Altinkaya SO, et al. Vascular endothelial growth factor +405 C/G polymorphism is highly associated with an increased risk of endometriosis in Turkish women. Arch Gynecol Obstet. Dec. 30, 2009.

Ammendola M, et al. Acid phosphatase locus 1 genetic polymorphism, endometriosis, and allergy. Fertil Steril. Oct. 2008;90(4): 1203-1205.

Arvanitis DA, et al. CYP1A1, CYP19, and GSTM1 polymorphisms increase the risk of endometriosis. Fertil Steril. Mar. 2003;79 Suppl 1:702-709.

Asghar T, et al. The tumor necrosis factor-alpha promoter—103 IC polymorphism is associated with decreased risk of endometriosis in a Japanese population. Hum Reprod. Nov. 2004;19(11):2509-2514.

Babu KA, et al. GSTM1, GSTT1 and CYP1A1 detoxification gene polymorphisms and their relationship with advanced stages of endometriosis in South Indian women. Pharmacogenet Genomics. Mar. 2005;15(3):167-172.

Bedaiwy MA, et al. Genetic polymorphism in the fibrinolytic system and endometriosis. Obstet Gynecol. Jul. 2006;108(1): 162-168.

Bhanoori M, et al. The G2964A 3'-untranslated region polymorphism of the signal transducer and activator of transcription 6 gene is associated with endometriosis in South Indian women. Hum Reprod. Apr. 2007;22(4):1026-1030.

Bhanoori M, et al. The vascular endothelial growth factor (VEGF) +405GG>C5'—untranslated region polymorphism and increased risk of endometriosis in South Indian woman: a case control study Hum Repod. Jul. 2005;20(7):1844-1849.

Bianco B, et al. +1730 G/A polymorphism of the estrogen receptor beta gene (ERbeta) may be an important genetic factor predisposing to endometriosis. Acta Obstet Gynecol Scand. 2009;88(12):1397-1401.

Borghese B, et al. Genetic polymorphisms of matrix metalloproeinase 12 and 13 genes are implicated in endometriosis progression. Hum Reprod. May 2008;23(5):1207-1213.

Caballero V, et al. Preliminary molecular genetic analysis of the Receptor Interacting Protein 140 (RIP140) in women affected by endometriosis. J Exp Clin Assist Reprod. Aug. 30, 2005;2:11.

Cayan F, et al. Association of G1057D variant of insulin receptor substrate-2 with endometriosis. Fertil Steril. Oct. 28, 2009.

Chae SJ, et al. Tumor necrosis factor (TNF)-TNF receptor gene polymorphisms and their serum levels in Korean women with endometriosis. Am J Reprod Immunol. Nov. 2008;60(5):432-439.

Chang CC, et al. The proline form of p53 codon 72 polymorphism is associated with endometriosis. Fertil Steril. Jan 2002;77(1)43-45.

Ertunc D, et al. Glutathione-S-transferase P1 gene polymorphism and susceptibility to endometriosis. Hum Reprod. Aug. 2005;20(8):2157-2161.

Gentilini D, et al. Progesterone receptor +331G/A polymorphism in endometriosis and deep-infiltrating endometriosis. Fertil Steril. Oct. 2008;90(4):1243-1245.

Gomes FM, et al. PTPN22 C1858T polymorphism in women with endometriosis. Am J Reprod Immunol. Mar. 1, 2010;63(3):227-232.

Govindan S, et al. Estrogen receptor-alpha gene (T/C) Pvu II polymorphism in endometriosis and uterine fibroids. Dis Markers. 2009;26(4)149-154.

Han YJ, et al. Haplotype analysis of the martix metalloproteinase-9 gene associated with advanced-stage endometriosis. Fertil Steril. Jun. 2009;91(6):2324-2330.

Hsieh YY, et al. Angiotensin I-converting enzyme Ace 2350*G and ACE-240*T-related genotypes and alleles are associated with higher susceptibility to endometriosis. Mol Hum Reprod. Jan. 2005;11(1):11-14.

Hsieh YY, et al. Angiotensin I-converting enzyme insertion-related genotypes and allele are associated with higher susceptibility of endometriosis and leiomyoma. Mol Reprod Dev. Jul. 2007;74(7):808-814.

Hsieh YY, et al. Estrogen receptor alpha dinucleotide repeat and cytochrome P450c17alpha gene polymorphisms are associated with susceptibility to endometriosis. Fertil Steril. Mar. 2005;83(3):567-572.

Hsieh YY, et al. Glutathione S-transferase M1*null genotype but not myeloperoxidase promoter G-463A polymorphism is associated with higher susceptibility to endometriosis. Mol Hum Reprod. Oct. 2004;10(10):713-717.

Hsieh YY, et al. Interleukin-2 receptor beta (IL-2R beta)-627*C homozygote but not IL-12R beta 1 codon 378 or IL-18 105 polymorphism is associated with higher susceptibility to endometriosis. Fertil Steril. Aug. 2005;84(2):510-512.

Hsieh YY, et al. T homozygote and allele of epidermal growth factor receptor 2073 gene polymorphism are associated with higher susceptibility to endometriosis and leiomyomas. Fertil Steril. Mar. 2005;83(3):796-799.

Ivashchenko TE, et al. Analysis of the polymorphic alleles of genes encoding phase 1 and phase 2 detoxication enzymes in patients with endometriosis. Genetika. Apr. 2003;39(4):427-430.

Kim JG, et al. Association between human alpha 2-Heremans Schmidt glycoprotein (AHSG) polymorphism and endometriosis in Korean women. Fertil Steril. Dec. 2004;82(6): 1497-1500.

(56) References Cited

OTHER PUBLICATIONS

Kim SH, et al. Association between susceptibility to advanced stage endometriosis and the genetic polymorphisms of aryl hydrocarbon receptor repressor and glutathione-S-transferase T1 genes, Hum Reprod. May 18, 2007;22(7): 1866-1870.
Kim SH, et al. Vascular endothelial growth factor gene +405 C/G polymorphism is associated with susceptibility to advanced stage endometriosis. Hum Reprod. Oct. 2005;20(10):2904-2908.
Kitawaki J, et al. Association of HLA class I and class II alleles with susceptibility to endometriosis. Hum Immunol. Nov. 2002;63(11): 1033-1038.
Kitawaki J, et al. Genetic contribution of the interleukin-10 promoter polymorphism in endometriosis susceptibility. Am J Reprod Immunol. Jan. 2002;47(1):12-18.
Kitawaki J, et al. Interferon-gamma gene dinucleotide (CA) repeat and interleukin-4 promoter region (-590C/T) polymorphisms in Japanese patients with endometriosis. Hum Reprod. Aug. 2004;19(8):1765-1769.
Kitawaki J, et al. Synergistic effect of interleukin-6 promoter (IL-634C/G) and intercellular adhesion molecule-1 (ICAM-1 469K/E) gene polymorphisms on the risk of endometriosis in Japanese women. Am J Reprod Immunal. Oct. 2006;56(4):267-274.
Kiyomizu M, et al. Association of two polymorphisms in the peroxisome proliferator-activated receptor-gamma gene with adenomyosis, endometriosis, and leiomyomata in Japanese women. J Soc Gynecol Investig. Jul 2006;13(5)372-377.
Lattuada D, et al. Analysis of the codon 72 polymorphism of the TP54 gene in patients with endometriosis. Mol Hum Reprod. Sep. 2004;10(9)651-654.
Lattuada D, et al. Genetics of endometriosis: a role for the progesterone receptor gene polymorphism PROGINS?Clin Endocrinal (Oxf). Aug. 2004;61(2):190-194.
Lee GH, et al. Association of tumor necrosis factor-{alpha} gene polymorphisms with advanced stage endometriosos. *Hum Reprod.* Apr. 2008;23(4):977-981.
Liu Q, et al. Association of polymorphisms—1154G/A and -2578C/A in the vascular endothelial growth factor gene with decreased risk of endometriosis in Chinese women. *Hum Reprod.* Jun. 16, 2009.
Shan K, et al. Association of three single nucleotide polymorphisms of the E-cadherin gene with endometriosis in a Chinese population. Reporduction. Aug. 2007;134(2):373-378.
Shan K, et al. The function of the SNP in the MMP1 and MMP3 promoter in susceptibility to endometriosis in China. Mol Hum Reprod. Jun 2005;11(6):423-427.
Teramoto M, et al. Genetic contribution of tumor necrosis factor (TNF)-alpha gene promoter (-1031, -863 and -857) and TNF receptor 2 gene polymorphisms in endometriosis susceptibility. Am J Reprod Immunol. May 2004;51(5):352-357.
Tsuchiya M, et al. Analysis of the AhR, ARNT, and AhRR gene polymorphisms: genetic contribution to endometriosis susceptibility and severity. Fertil Steril. Aug. 2005;84(2):454-458.
Tsuchiya M, et al. Association between endometriosis and genetic polymorphisms of the estradiol-synthesizing enzyme genes HSD17B1 and CYP19. Hum Reprod. Apr. 2005;20(4):974-978.
Vigano P, et al. Intercellular adhesion molecule-1 (ICAM-1) gene polymorphisms in endometriosis. Mol. Hum Reprod. Jan. 2003;9(1):47-52.
Vijaya Lakshmi K, et al. Tumor necrosis factor alpha-C850T polymorphism is significantly associated with endometriosis in Asian Indian women. *Fertil Steril.* Apr. 24, 2009.
Wang Z, et al. Polymorphisms in the estrogen receptor beta gene but not estrogen receptor alpha gene affect the risk of developing endometriosis in a Japanese population. Fertil Steril. Jun. 2004;81(6):1650-1656.
Wu YL, et al. Sensitive and specific real-time polymerase chain reaction assays to accurately determine copy number variations (CNVs) of human complement C4A, C4B, C4-long, C4-short, and RCCX modules: elucidation of C4 CNVs in 50 consanguineous subjects with defined HLA genotypes. J Immunol. Sep. 1, 2007;179(5):3012-3025.
Zervou S, et al. The Glu298—>Asp polymorphism of the endothelial nitric oxide synthase gene is associated with endometriosis. Fertil Steril. Dec. 2003;80(6):1524-1525.
Zhang X, et al. Interleukin-10 gene promoter polymorphisms and their protein production in peritoneal fluid inpatients with endometriosis. *Mol Hum Reprod.* Feb. 2007; 13(2): 135-140.
Albertsen, et al., Genome-Wide Association Study Link Novel Loci to Endometriosis. PLOS One, 8.3 (Mar. 5, 2013): e58257, 1-8.
Baranova, et al. Gluthione 5-transferase M1 gene polymorphism and susceptibility to endometriosis in a French population, MHR, 3.9 (1997): 775-780.
Benner, et al. Evolution, language and analogy in functional genomics. Trends in Genetics, 17:414-418 (2001).
Bhangale et al., Estimating coverage and power for genetic association studies using near-complete variation data. Nat Genet. 40(7):841-843 (2008).
Chettier et al., Endometriosis Is Associated with Rare Copy Number Variants, PLOS One, 9.8 (Aug. 2014), e103968, 1-11.
Colette et al, Are aromatase inhibitors effect in endometriosis treatment, Expert Opinion, 917-931 (2011).
Db SNP, SNP ss13045391, NCBI, Oct. 22, 2003, 1-8.
Dun, et al. Advances in the genetics of endometriosis, Genome Medicine, 2.75 (2010): 1-6.
Gimenes et al., The progins progesterone receptor gene polymorphism is not related to endometriosis-associated infertility or to idiopathic infertility, Clinical Science, 65.11 (2010): 1073-1076.
Govindan, et al. Association of progesterone receptor gene polymorphism (PROGINS) with endometriosis, uterine fibroids and breast cancer, Cancer Biomarkers, 3.2 (May 21, 2007): 73-78.
"HUENTELMAN, et al. Calmodulin-binding transcription activator 1 (CAMTA1)alleles predispose human episodic memory performance", Hum Mol Genet. Apr. 30, 2007, 16(12): 1469-1477.
"International Search Report and Written Opinion dated Jan. 16, 2009 for International PCT Patent Application No. PCT/US2008066061".
"International Search Report and Written Opinion dated Mar. 11, 2011 for International PCT Patent Application No. PCT/US/2010/032067".
"International Search Report and Written Opinion dated Sep. 1, 2009 for International PCT Patent Application No. PCT/US/2009043065".
Kado et al., Association of the CYP17 gene and CYP19 gene polymorphisms with risk of endometriosis in Japanese women, Human Reproduction, 17.4 (2002): 897-902.
Kennedy et al., ESHRE guideline for the diagnosis and treatment of endometriosis, Hum Repro, 20.10 (Jun. 24, 2005): 2698-2704.
Matalliotakis et al., Genetic association study in a three-generation family with seven members with endometriosis.Mol Med Rep. 16(5):6077-6080 (2017).
May, Robert M. How Many Species Are There on Earth? Science, 241: 1141-1449 (1988).
"NIU, et al. Bayesian haplotype inference for multiple linked single nucleotide polymorphism, 2002, Am. J. Hum. Genet. Vol. 70, pp. 157-169".
Noaham, et al. Developing Symptom-based Predictive Models of Endometriosis as a Clinical Screening Tool: Results from a Multicenter Study, Fertility and Sterility, 98.3 (Sep. 2012): 692-701 e5.
Office action dated Jan. 22, 2015 for U.S. Appl. No. 13/159,132.
Office action dated May 31, 2013 for U.S. Appl. No. 13/159,132.
Office action dated Jun. 11, 2015 for U.S. Appl. No. 13/159,132.
Office action dated Nov. 8, 2013 for U.S. Appl. No. 13/159,132.
Pennisi. A closer look at SNPs suggests difficulties. Science. Sep. 18, 1998; 281(5384): 1787-1789.
Petrozza, et al. A polymorphism in the biliary glycoprotein gene in women with endometriosis, FS, 78 (2002): s198-199.
Rahmioglu, et al. Genetic variants underlying risk of endometriosis: insights from meta-analysis of eight genome-wide association and replication datasets, Hum Repro, (Mar. 27, 2014): 1-15.
Schlaff W. D. et al. Subcutaneous injection of depot medroxyprogesterone acetate compared with leuprolide acetate in the treatment of endometriosis-associated pain. Fertility and Sterility, 85.2 (Feb. 2006): 314-325.

(56) References Cited

OTHER PUBLICATIONS

Shaw R.W et al. "Intranasal treatment with luteinising hormone releasing hormone agonist in women with endometriosis." British Medical Journal, 287 (Dec. 3, 1983): 1667-1669.
International Search Report and Written Opinion dated Aug. 8, 2018 for International PCT Patent Application No. PCT/US2018/022743.
Office action dated Aug. 27, 2018 for U.S. Appl. No. 13/159,132.
Terwilliger, et al. An utter refutation of the Fundamental Theorem of the HapMap, EJHG, (2006): 426-437.
Thomas E.J et al. Successful treatment of asymptomatic endometriosis: does it benefit infertile women? British Medical Journal, 294 (May 2, 1987): 1117-1119.
U.S. Appl. No. 13/159,132 Office Action dated Aug. 27, 2018.
Wieser, et al. PROGINS receptor gene polymorphism is associated with endometriosis, Fertility and Sterility, 77.2 ((Feb. 2002): 309-312.

\* cited by examiner

```
                               SEQUENCE LISTING

<160> NUMBER OF SEQ ID NOS: 898

<210> SEQ ID NO 1
<211> LENGTH: 33
<212> TYPE: DNA
<213> ORGANISM: Homo Sapiens

<400> SEQUENCE: 1
tcacgccacc caggaarcct tctgtgatct gtt                                       33

<210> SEQ ID NO 2
<211> LENGTH: 33
<212> TYPE: DNA
<213> ORGANISM: Homo Sapiens

<400> SEQUENCE: 2
aacgtcagat cctctcscct gagaatatct gaa                                       33

<210> SEQ ID NO 3
<211> LENGTH: 33
<212> TYPE: DNA
<213> ORGANISM: Homo Sapiens

<400> SEQUENCE: 3
ctaatcctat tttgcasata aagaagcagg tta                                       33

<210> SEQ ID NO 4
<211> LENGTH: 33
<212> TYPE: DNA
<213> ORGANISM: Homo Sapiens

<400> SEQUENCE: 4
ccttcctgcc ttcttcyagc ctacaatgac atc                                       33

<210> SEQ ID NO 5
<211> LENGTH: 33
<212> TYPE: DNA
<213> ORGANISM: Homo Sapiens

<400> SEQUENCE: 5
aaatccctat aagagamgac acattcgcta aac                                       33

<210> SEQ ID NO 6
<211> LENGTH: 33
<212> TYPE: DNA
<213> ORGANISM: Homo Sapiens

<400> SEQUENCE: 6
tgactcttgg aagaackgtt ctgtggagaa gag                                       33

<210> SEQ ID NO 7
<211> LENGTH: 33
```

```
<212> TYPE: DNA
<213> ORGANISM: Homo Sapiens

<400> SEQUENCE: 7
tttactggaa tcgaggyagt ggcaccaaac tgt                                      33

<210> SEQ ID NO 8
<211> LENGTH: 33
<212> TYPE: DNA
<213> ORGANISM: Homo Sapiens

<400> SEQUENCE: 8
ctttcagctc acatacsgta aacaagtgtc cct                                      33

<210> SEQ ID NO 9
<211> LENGTH: 33
<212> TYPE: DNA
<213> ORGANISM: Homo Sapiens

<400> SEQUENCE: 9
caattatcat agtaacmata ggaatgataa gat                                      33

<210> SEQ ID NO 10
<211> LENGTH: 33
<212> TYPE: DNA
<213> ORGANISM: Homo Sapiens

<400> SEQUENCE: 10
tataagtggg ggctaarcat ttaatactca tga                                      33

<210> SEQ ID NO 11
<211> LENGTH: 33
<212> TYPE: DNA
<213> ORGANISM: Homo Sapiens

<400> SEQUENCE: 11
tgacaaagca gaagaayaca gaaagaacaa cag                                      33

<210> SEQ ID NO 12
<211> LENGTH: 33
<212> TYPE: DNA
<213> ORGANISM: Homo Sapiens

<400> SEQUENCE: 12
tattctgcct atgaagkatg taaaccttttt tat                                     33

<210> SEQ ID NO 13
<211> LENGTH: 33
<212> TYPE: DNA
<213> ORGANISM: Homo Sapiens

<400> SEQUENCE: 13
agattcaatc gaatccrcat aactcccaaa ttt                                      33

<210> SEQ ID NO 14
<211> LENGTH: 33
<212> TYPE: DNA
<213> ORGANISM: Homo Sapiens

<400> SEQUENCE: 14
agaaggctat ttattaygct cttttttcttc ctc                                     33

<210> SEQ ID NO 15
```

```
<211> LENGTH: 33
<212> TYPE: DNA
<213> ORGANISM: Homo Sapiens

<400> SEQUENCE: 15
tcacgtgctg tgatccrcat gaaaaagctc cac                                  33

<210> SEQ ID NO 16
<211> LENGTH: 33
<212> TYPE: DNA
<213> ORGANISM: Homo Sapiens

<400> SEQUENCE: 16
catttcactt ctacaaytcc agagtggcat ggg                                  33

<210> SEQ ID NO 17
<211> LENGTH: 33
<212> TYPE: DNA
<213> ORGANISM: Homo Sapiens

<400> SEQUENCE: 17
agattctgca ctttgaygga aggagttaga aaa                                  33

<210> SEQ ID NO 18
<211> LENGTH: 33
<212> TYPE: DNA
<213> ORGANISM: Homo Sapiens

<400> SEQUENCE: 18
attatttagc cattcayaat aagccacgtg tgt                                  33

<210> SEQ ID NO 19
<211> LENGTH: 33
<212> TYPE: DNA
<213> ORGANISM: Homo Sapiens

<400> SEQUENCE: 19
cacaagtgct cttcaartga gtcatttta tca                                   33

<210> SEQ ID NO 20
<211> LENGTH: 33
<212> TYPE: DNA
<213> ORGANISM: Homo Sapiens

<400> SEQUENCE: 20
agtactttga tttcaartac ttccattaaa aaa                                  33

<210> SEQ ID NO 21
<211> LENGTH: 33
<212> TYPE: DNA
<213> ORGANISM: Homo Sapiens

<400> SEQUENCE: 21
ggactgagag aatggamaaa ctgatccaca gga                                  33

<210> SEQ ID NO 22
<211> LENGTH: 33
<212> TYPE: DNA
<213> ORGANISM: Homo Sapiens

<400> SEQUENCE: 22
cgtatgaaca ttcaaartgg taagtgataa ttt                                  33
```

<210> SEQ ID NO 23
<211> LENGTH: 33
<212> TYPE: DNA
<213> ORGANISM: Homo Sapiens

<400> SEQUENCE: 23
acttcctgaa gctgtakgag gaactggcac atc                                33

<210> SEQ ID NO 24
<211> LENGTH: 33
<212> TYPE: DNA
<213> ORGANISM: Homo Sapiens

<400> SEQUENCE: 24
gaaacttgtt caccatyaca ctaatgatta gtg                                33

<210> SEQ ID NO 25
<211> LENGTH: 33
<212> TYPE: DNA
<213> ORGANISM: Homo Sapiens

<400> SEQUENCE: 25
ctcagaatat agattgyatt gattagatgt ttg                                33

<210> SEQ ID NO 26
<211> LENGTH: 33
<212> TYPE: DNA
<213> ORGANISM: Homo Sapiens

<400> SEQUENCE: 26
tctgaaccta tgattckatc tttactaaga gac                                33

<210> SEQ ID NO 27
<211> LENGTH: 33
<212> TYPE: DNA
<213> ORGANISM: Homo Sapiens

<400> SEQUENCE: 27
tgacttctgg gtgctcwcag ttttctaagg gaa                                33

<210> SEQ ID NO 28
<211> LENGTH: 33
<212> TYPE: DNA
<213> ORGANISM: Homo Sapiens

<400> SEQUENCE: 28
caggacatgg agatacraaa aagctgagca cat                                33

<210> SEQ ID NO 29
<211> LENGTH: 33
<212> TYPE: DNA
<213> ORGANISM: Homo Sapiens

<400> SEQUENCE: 29
aagtctgaga cggaaakgag acttttcatt gaa                                33

<210> SEQ ID NO 30
<211> LENGTH: 33
<212> TYPE: DNA
<213> ORGANISM: Homo Sapiens

<400> SEQUENCE: 30
gtggggcttt agagaamggc ttcatgttac aca                                33

```
<210> SEQ ID NO 31
<211> LENGTH: 33
<212> TYPE: DNA
<213> ORGANISM: Homo Sapiens

<400> SEQUENCE: 31
gaatataatc ttctcayatc ctggtatgtc aat                              33

<210> SEQ ID NO 32
<211> LENGTH: 33
<212> TYPE: DNA
<213> ORGANISM: Homo Sapiens

<400> SEQUENCE: 32
caccacagaa taatgcragt ccaagtgctg aat                              33

<210> SEQ ID NO 33
<211> LENGTH: 33
<212> TYPE: DNA
<213> ORGANISM: Homo Sapiens

<400> SEQUENCE: 33
tgtcaactac tatatcyatg aggaatacta tca                              33

<210> SEQ ID NO 34
<211> LENGTH: 33
<212> TYPE: DNA
<213> ORGANISM: Homo Sapiens

<400> SEQUENCE: 34
gtatttctgt aaatgakagt ggcattaaga tct                              33

<210> SEQ ID NO 35
<211> LENGTH: 33
<212> TYPE: DNA
<213> ORGANISM: Homo Sapiens

<400> SEQUENCE: 35
atttatacag ctttcakaca ttatggtgct atg                              33

<210> SEQ ID NO 36
<211> LENGTH: 33
<212> TYPE: DNA
<213> ORGANISM: Homo Sapiens

<400> SEQUENCE: 36
ctgttatttt aaatgaraga ggctggtaac aac                              33

<210> SEQ ID NO 37
<211> LENGTH: 33
<212> TYPE: DNA
<213> ORGANISM: Homo Sapiens

<400> SEQUENCE: 37
tgtgttacaa aaagcayagc atactataaa cac                              33

<210> SEQ ID NO 38
<211> LENGTH: 33
<212> TYPE: DNA
<213> ORGANISM: Homo Sapiens

<400> SEQUENCE: 38
gatactgttc tctttcraat aggatccatt ttt                              33
```

<210> SEQ ID NO 39
<211> LENGTH: 33
<212> TYPE: DNA
<213> ORGANISM: Homo Sapiens

<400> SEQUENCE: 39
tttgtacttg taactaygac attattcggt caa                33

<210> SEQ ID NO 40
<211> LENGTH: 33
<212> TYPE: DNA
<213> ORGANISM: Homo Sapiens

<400> SEQUENCE: 40
atttcaacgt ttcttayatt tcccatggct tac                33

<210> SEQ ID NO 41
<211> LENGTH: 33
<212> TYPE: DNA
<213> ORGANISM: Homo Sapiens

<400> SEQUENCE: 41
ccaccaactg actgtgyagc cttggctggt cac                33

<210> SEQ ID NO 42
<211> LENGTH: 33
<212> TYPE: DNA
<213> ORGANISM: Homo Sapiens

<400> SEQUENCE: 42
gggtaggaag gattcargac aatgactcaa gct                33

<210> SEQ ID NO 43
<211> LENGTH: 33
<212> TYPE: DNA
<213> ORGANISM: Homo Sapiens

<400> SEQUENCE: 43
tctgccctct tataaaytat catgtgttac ctg                33

<210> SEQ ID NO 44
<211> LENGTH: 33
<212> TYPE: DNA
<213> ORGANISM: Homo Sapiens

<400> SEQUENCE: 44
atgccaggag gccccaratg agcttcacct agc                33

<210> SEQ ID NO 45
<211> LENGTH: 33
<212> TYPE: DNA
<213> ORGANISM: Homo Sapiens

<400> SEQUENCE: 45
attgaatgtt cttcccraac atcacatagg cac                33

<210> SEQ ID NO 46
<211> LENGTH: 33
<212> TYPE: DNA
<213> ORGANISM: Homo Sapiens

<400> SEQUENCE: 46
tgggaagaac attcaakagt agacaaatgg cca                                    33

<210> SEQ ID NO 47
<211> LENGTH: 33
<212> TYPE: DNA
<213> ORGANISM: Homo Sapiens

<400> SEQUENCE: 47
aactgtagca aaaggratg caatcagata tcc                                     33

<210> SEQ ID NO 48
<211> LENGTH: 33
<212> TYPE: DNA
<213> ORGANISM: Homo Sapiens

<400> SEQUENCE: 48
agttgtgaag atgaaaygcc ataaccaaca tta                                    33

<210> SEQ ID NO 49
<211> LENGTH: 33
<212> TYPE: DNA
<213> ORGANISM: Homo Sapiens

<400> SEQUENCE: 49
cacccagctg aaacacrggg tgcatccagg ctg                                    33

<210> SEQ ID NO 50
<211> LENGTH: 33
<212> TYPE: DNA
<213> ORGANISM: Homo Sapiens

<400> SEQUENCE: 50
ttcttgacct ctaacaytct aaatcccacc cac                                    33

<210> SEQ ID NO 51
<211> LENGTH: 33
<212> TYPE: DNA
<213> ORGANISM: Homo Sapiens

<400> SEQUENCE: 51
aggcttctcg tggcccyact cttgctagct tgg                                    33

<210> SEQ ID NO 52
<211> LENGTH: 33
<212> TYPE: DNA
<213> ORGANISM: Homo Sapiens

<400> SEQUENCE: 52
ttctctcttg gtagaargtg gggcctgaat aaa                                    33

<210> SEQ ID NO 53
<211> LENGTH: 33
<212> TYPE: DNA
<213> ORGANISM: Homo Sapiens

<400> SEQUENCE: 53
ttgatctttg tagccamtga taatgatttc aaa                                    33

<210> SEQ ID NO 54
<211> LENGTH: 33
<212> TYPE: DNA
<213> ORGANISM: Homo Sapiens

<400> SEQUENCE: 54
tgggcatatg aataaasaga agagcctgat ttg                                33

<210> SEQ ID NO 55
<211> LENGTH: 33
<212> TYPE: DNA
<213> ORGANISM: Homo Sapiens

<400> SEQUENCE: 55
tcagtcaccc tatggargta tcgtgtcttg cca                                33

<210> SEQ ID NO 56
<211> LENGTH: 33
<212> TYPE: DNA
<213> ORGANISM: Homo Sapiens

<400> SEQUENCE: 56
ttcactttca acagacraat atcttctatg cca                                33

<210> SEQ ID NO 57
<211> LENGTH: 33
<212> TYPE: DNA
<213> ORGANISM: Homo Sapiens

<400> SEQUENCE: 57
aaagtgattt gtcctaycgc gcagaaaaac aat                                33

<210> SEQ ID NO 58
<211> LENGTH: 33
<212> TYPE: DNA
<213> ORGANISM: Homo Sapiens

<400> SEQUENCE: 58
ggtcattccc agcatawgca tttcaccttc act                                33

<210> SEQ ID NO 59
<211> LENGTH: 33
<212> TYPE: DNA
<213> ORGANISM: Homo Sapiens

<400> SEQUENCE: 59
aatgacctgg ataatakctg ggtgaaagaa aaa                                33

<210> SEQ ID NO 60
<211> LENGTH: 33
<212> TYPE: DNA
<213> ORGANISM: Homo Sapiens

<400> SEQUENCE: 60
catcttctat gatgagract ccctttttatt atg                               33

<210> SEQ ID NO 61
<211> LENGTH: 33
<212> TYPE: DNA
<213> ORGANISM: Homo Sapiens

<400> SEQUENCE: 61
caccttctca gagaaaygag ctttggcttt ggg                                33

<210> SEQ ID NO 62
<211> LENGTH: 33
<212> TYPE: DNA
<213> ORGANISM: Homo Sapiens

```
<400> SEQUENCE: 62
gtcaaagaaa atagagkcga aagatcaaaa tga                              33

<210> SEQ ID NO 63
<211> LENGTH: 33
<212> TYPE: DNA
<213> ORGANISM: Homo Sapiens

<400> SEQUENCE: 63
cctgaagagg gttaagraag agtgatcaga ttt                              33

<210> SEQ ID NO 64
<211> LENGTH: 33
<212> TYPE: DNA
<213> ORGANISM: Homo Sapiens

<400> SEQUENCE: 64
aactggattt gagcagraac atgtaaaaaa gtg                              33

<210> SEQ ID NO 65
<211> LENGTH: 33
<212> TYPE: DNA
<213> ORGANISM: Homo Sapiens

<400> SEQUENCE: 65
caggtctgtt gtatagycca cctcaatgtg gag                              33

<210> SEQ ID NO 66
<211> LENGTH: 33
<212> TYPE: DNA
<213> ORGANISM: Homo Sapiens

<400> SEQUENCE: 66
accatagttc tgaataygct tagatcttta ttt                              33

<210> SEQ ID NO 67
<211> LENGTH: 33
<212> TYPE: DNA
<213> ORGANISM: Homo Sapiens

<400> SEQUENCE: 67
gtttttcttt ctctcayaca cagctcaaca caa                              33

<210> SEQ ID NO 68
<211> LENGTH: 33
<212> TYPE: DNA
<213> ORGANISM: Homo Sapiens

<400> SEQUENCE: 68
caatctccag aagaaaygaa gaccaaaagt gtt                              33

<210> SEQ ID NO 69
<211> LENGTH: 33
<212> TYPE: DNA
<213> ORGANISM: Homo Sapiens

<400> SEQUENCE: 69
agacagactg gcaaaarggg gtgacattcc tat                              33

<210> SEQ ID NO 70
<211> LENGTH: 33
<212> TYPE: DNA
<213> ORGANISM: Homo Sapiens
```

```
<400> SEQUENCE: 70
actaggagac tagctargaa ctctttcct ccc                                    33

<210> SEQ ID NO 71
<211> LENGTH: 33
<212> TYPE: DNA
<213> ORGANISM: Homo Sapiens

<400> SEQUENCE: 71
ttaatcatga tcattaygta gtcaagttgc ttt                                   33

<210> SEQ ID NO 72
<211> LENGTH: 33
<212> TYPE: DNA
<213> ORGANISM: Homo Sapiens

<400> SEQUENCE: 72
actgtgtttt cacttcratg ctcccagaat tct                                   33

<210> SEQ ID NO 73
<211> LENGTH: 33
<212> TYPE: DNA
<213> ORGANISM: Homo Sapiens

<400> SEQUENCE: 73
ccaaattctg atagtawaac agtccaagtt atc                                   33

<210> SEQ ID NO 74
<211> LENGTH: 33
<212> TYPE: DNA
<213> ORGANISM: Homo Sapiens

<400> SEQUENCE: 74
taatgtatat aacttayaga gcctgtctat cta                                   33

<210> SEQ ID NO 75
<211> LENGTH: 33
<212> TYPE: DNA
<213> ORGANISM: Homo Sapiens

<400> SEQUENCE: 75
aacagaaaat ggatccrcct gaggtaaggg gat                                   33

<210> SEQ ID NO 76
<211> LENGTH: 33
<212> TYPE: DNA
<213> ORGANISM: Homo Sapiens

<400> SEQUENCE: 76
aacagaaaat taagatmaga ttggctaaca aga                                   33

<210> SEQ ID NO 77
<211> LENGTH: 33
<212> TYPE: DNA
<213> ORGANISM: Homo Sapiens

<400> SEQUENCE: 77
tctaattaac tagaaarctc tctaagactc tga                                   33

<210> SEQ ID NO 78
<211> LENGTH: 33
<212> TYPE: DNA
```

<213> ORGANISM: Homo Sapiens

<400> SEQUENCE: 78
ctcttacact tccaggycac ctttctttac tgt            33

<210> SEQ ID NO 79
<211> LENGTH: 33
<212> TYPE: DNA
<213> ORGANISM: Homo Sapiens

<400> SEQUENCE: 79
cttaaaatta agatgcrgaa atatgttttt aat            33

<210> SEQ ID NO 80
<211> LENGTH: 33
<212> TYPE: DNA
<213> ORGANISM: Homo Sapiens

<400> SEQUENCE: 80
cccttcactt taatcakgca acctttata gaa            33

<210> SEQ ID NO 81
<211> LENGTH: 33
<212> TYPE: DNA
<213> ORGANISM: Homo Sapiens

<400> SEQUENCE: 81
aggcatcagg aatggargag caagatattg agg            33

<210> SEQ ID NO 82
<211> LENGTH: 33
<212> TYPE: DNA
<213> ORGANISM: Homo Sapiens

<400> SEQUENCE: 82
gattaccaag atagacrcga atggattcct agt            33

<210> SEQ ID NO 83
<211> LENGTH: 33
<212> TYPE: DNA
<213> ORGANISM: Homo Sapiens

<400> SEQUENCE: 83
gcaacctcac cctcacmgaa tcttacttca atg            33

<210> SEQ ID NO 84
<211> LENGTH: 33
<212> TYPE: DNA
<213> ORGANISM: Homo Sapiens

<400> SEQUENCE: 84
cttaatattt ggtaaakgca agatacattg tag            33

<210> SEQ ID NO 85
<211> LENGTH: 33
<212> TYPE: DNA
<213> ORGANISM: Homo Sapiens

<400> SEQUENCE: 85
tgaatggtga aaatacyaat ggcgatgaca atg            33

<210> SEQ ID NO 86
<211> LENGTH: 33

```
<212> TYPE: DNA
<213> ORGANISM: Homo Sapiens

<400> SEQUENCE: 86
tgctgatgga tcatgargga tggtaagcag aaa                                33

<210> SEQ ID NO 87
<211> LENGTH: 33
<212> TYPE: DNA
<213> ORGANISM: Homo Sapiens

<400> SEQUENCE: 87
ttgtgttaag taacaargag gtgactgtta aca                                33

<210> SEQ ID NO 88
<211> LENGTH: 33
<212> TYPE: DNA
<213> ORGANISM: Homo Sapiens

<400> SEQUENCE: 88
aaatgagaaa ttaaacyagt gataaccaac ttt                                33

<210> SEQ ID NO 89
<211> LENGTH: 33
<212> TYPE: DNA
<213> ORGANISM: Homo Sapiens

<400> SEQUENCE: 89
tttcagatct gataaarccc atgacattgt gaa                                33

<210> SEQ ID NO 90
<211> LENGTH: 33
<212> TYPE: DNA
<213> ORGANISM: Homo Sapiens

<400> SEQUENCE: 90
aaaaggtaaa caatgakctt atgtctatta ggt                                33

<210> SEQ ID NO 91
<211> LENGTH: 33
<212> TYPE: DNA
<213> ORGANISM: Homo Sapiens

<400> SEQUENCE: 91
ctcagctttg tatctckgac ttgttcaatg tta                                33

<210> SEQ ID NO 92
<211> LENGTH: 33
<212> TYPE: DNA
<213> ORGANISM: Homo Sapiens

<400> SEQUENCE: 92
ctgcttagtc ttccagrcca cctctttcaa ctg                                33

<210> SEQ ID NO 93
<211> LENGTH: 33
<212> TYPE: DNA
<213> ORGANISM: Homo Sapiens

<400> SEQUENCE: 93
cactgtttag cctaccrcag tccatcttct gat                                33

<210> SEQ ID NO 94
```

```
<211> LENGTH: 33
<212> TYPE: DNA
<213> ORGANISM: Homo Sapiens

<400> SEQUENCE: 94
agaggtcatt gaaatayaag tgattattga tag                                33

<210> SEQ ID NO 95
<211> LENGTH: 33
<212> TYPE: DNA
<213> ORGANISM: Homo Sapiens

<400> SEQUENCE: 95
tggcattatt ccagacyagt ttgctaacat taa                                33

<210> SEQ ID NO 96
<211> LENGTH: 33
<212> TYPE: DNA
<213> ORGANISM: Homo Sapiens

<400> SEQUENCE: 96
tctaatgtct cttagcwacc tatgcaatct aaa                                33

<210> SEQ ID NO 97
<211> LENGTH: 33
<212> TYPE: DNA
<213> ORGANISM: Homo Sapiens

<400> SEQUENCE: 97
gctcactgat atttaartct tgccaatcaa aat                                33

<210> SEQ ID NO 98
<211> LENGTH: 33
<212> TYPE: DNA
<213> ORGANISM: Homo Sapiens

<400> SEQUENCE: 98
tataattaag gtctaaygcc atgccacaat tga                                33

<210> SEQ ID NO 99
<211> LENGTH: 33
<212> TYPE: DNA
<213> ORGANISM: Homo Sapiens

<400> SEQUENCE: 99
aaatccaatt gacaaamtaa cacaaacaaa ata                                33

<210> SEQ ID NO 100
<211> LENGTH: 33
<212> TYPE: DNA
<213> ORGANISM: Homo Sapiens

<400> SEQUENCE: 100
tttccctaat ggttcaygtt attatgcaat tgt                                33

<210> SEQ ID NO 101
<211> LENGTH: 33
<212> TYPE: DNA
<213> ORGANISM: Homo Sapiens

<400> SEQUENCE: 101
acatgctttc agtaaaygtt acttatgatt ctt                                33
```

<210> SEQ ID NO 102
<211> LENGTH: 33
<212> TYPE: DNA
<213> ORGANISM: Homo Sapiens

<400> SEQUENCE: 102
ctccagctgg ccaaacyctt gattttgtc ttc                                    33

<210> SEQ ID NO 103
<211> LENGTH: 33
<212> TYPE: DNA
<213> ORGANISM: Homo Sapiens

<400> SEQUENCE: 103
ggttgatggt tacaaargta cagctaggac aga                                    33

<210> SEQ ID NO 104
<211> LENGTH: 33
<212> TYPE: DNA
<213> ORGANISM: Homo Sapiens

<400> SEQUENCE: 104
cctttgggta tacacaragt aatgagattg ctg                                    33

<210> SEQ ID NO 105
<211> LENGTH: 33
<212> TYPE: DNA
<213> ORGANISM: Homo Sapiens

<400> SEQUENCE: 105
cagagaggat tacaaasaag gtgcttcata tta                                    33

<210> SEQ ID NO 106
<211> LENGTH: 33
<212> TYPE: DNA
<213> ORGANISM: Homo Sapiens

<400> SEQUENCE: 106
caaagacacc actaaamatt ttcttcaggc gaa                                    33

<210> SEQ ID NO 107
<211> LENGTH: 33
<212> TYPE: DNA
<213> ORGANISM: Homo Sapiens

<400> SEQUENCE: 107
tgtcacttta ctgagarcaa ctaggtttta ctt                                    33

<210> SEQ ID NO 108
<211> LENGTH: 33
<212> TYPE: DNA
<213> ORGANISM: Homo Sapiens

<400> SEQUENCE: 108
catcaatcat cattacygca cagcctgtct gca                                    33

<210> SEQ ID NO 109
<211> LENGTH: 33
<212> TYPE: DNA
<213> ORGANISM: Homo Sapiens

<400> SEQUENCE: 109
taccaatgac tgaaaaygtg ggccacacac aca                                    33

```
<210> SEQ ID NO 110
<211> LENGTH: 33
<212> TYPE: DNA
<213> ORGANISM: Homo Sapiens

<400> SEQUENCE: 110
aaattatacg tcacctyaat actctgggga aaa                               33

<210> SEQ ID NO 111
<211> LENGTH: 33
<212> TYPE: DNA
<213> ORGANISM: Homo Sapiens

<400> SEQUENCE: 111
tatgtgccat gccaggkaga tatgttccac acc                               33

<210> SEQ ID NO 112
<211> LENGTH: 33
<212> TYPE: DNA
<213> ORGANISM: Homo Sapiens

<400> SEQUENCE: 112
cagccactcc attatcwcaa agaagggttt aca                               33

<210> SEQ ID NO 113
<211> LENGTH: 33
<212> TYPE: DNA
<213> ORGANISM: Homo Sapiens

<400> SEQUENCE: 113
acacttttta atacaakgga atagcaacca ggt                               33

<210> SEQ ID NO 114
<211> LENGTH: 33
<212> TYPE: DNA
<213> ORGANISM: Homo Sapiens

<400> SEQUENCE: 114
cagtgtttcc tgtttakgtg ggaataaagt tat                               33

<210> SEQ ID NO 115
<211> LENGTH: 33
<212> TYPE: DNA
<213> ORGANISM: Homo Sapiens

<400> SEQUENCE: 115
tagattgtaa acactaygga cccttgcctc ttg                               33

<210> SEQ ID NO 116
<211> LENGTH: 33
<212> TYPE: DNA
<213> ORGANISM: Homo Sapiens

<400> SEQUENCE: 116
tggctccgga atacaayggc agactaattt atg                               33

<210> SEQ ID NO 117
<211> LENGTH: 33
<212> TYPE: DNA
<213> ORGANISM: Homo Sapiens

<400> SEQUENCE: 117
tgacagtgaa aaatagratg ctatcatata ggt                               33
```

<210> SEQ ID NO 118
<211> LENGTH: 33
<212> TYPE: DNA
<213> ORGANISM: Homo Sapiens

<400> SEQUENCE: 118
atttaacctt caataamcct gtcagatgcc agg                33

<210> SEQ ID NO 119
<211> LENGTH: 33
<212> TYPE: DNA
<213> ORGANISM: Homo Sapiens

<400> SEQUENCE: 119
acttactcct cagtgawatt ccaagcagca ccg                33

<210> SEQ ID NO 120
<211> LENGTH: 33
<212> TYPE: DNA
<213> ORGANISM: Homo Sapiens

<400> SEQUENCE: 120
gcaacaaact atgagcrcgt ggtaaagagt gag                33

<210> SEQ ID NO 121
<211> LENGTH: 33
<212> TYPE: DNA
<213> ORGANISM: Homo Sapiens

<400> SEQUENCE: 121
agttccagaa gcattgycag tgctaagagt gaa                33

<210> SEQ ID NO 122
<211> LENGTH: 33
<212> TYPE: DNA
<213> ORGANISM: Homo Sapiens

<400> SEQUENCE: 122
tcattcattt tcttacmcca gtagttgcta aat                33

<210> SEQ ID NO 123
<211> LENGTH: 33
<212> TYPE: DNA
<213> ORGANISM: Homo Sapiens

<400> SEQUENCE: 123
taactagaag tgagaartat tggttcaagt ggt                33

<210> SEQ ID NO 124
<211> LENGTH: 33
<212> TYPE: DNA
<213> ORGANISM: Homo Sapiens

<400> SEQUENCE: 124
tgatgccttt tgggtaygta gttgatgtga aac                33

<210> SEQ ID NO 125
<211> LENGTH: 33
<212> TYPE: DNA
<213> ORGANISM: Homo Sapiens

<400> SEQUENCE: 125

```
cctgggacaa aaggacsaaa aacactcttc tgt            33

<210> SEQ ID NO 126
<211> LENGTH: 33
<212> TYPE: DNA
<213> ORGANISM: Homo Sapiens

<400> SEQUENCE: 126
gtgatcattc ttctacrctc acaacgctat atg            33

<210> SEQ ID NO 127
<211> LENGTH: 33
<212> TYPE: DNA
<213> ORGANISM: Homo Sapiens

<400> SEQUENCE: 127
ccttgctttt gctgaaygat ttaatatgcc att            33

<210> SEQ ID NO 128
<211> LENGTH: 33
<212> TYPE: DNA
<213> ORGANISM: Homo Sapiens

<400> SEQUENCE: 128
cctatctaaa gtagacycct atcctagtaa ttg            33

<210> SEQ ID NO 129
<211> LENGTH: 33
<212> TYPE: DNA
<213> ORGANISM: Homo Sapiens

<400> SEQUENCE: 129
agcagtacaa actcaarcag ttctggttgg ttg            33

<210> SEQ ID NO 130
<211> LENGTH: 33
<212> TYPE: DNA
<213> ORGANISM: Homo Sapiens

<400> SEQUENCE: 130
cccagtagag gacagayagg tacaactgaa gcc            33

<210> SEQ ID NO 131
<211> LENGTH: 33
<212> TYPE: DNA
<213> ORGANISM: Homo Sapiens

<400> SEQUENCE: 131
gtactgatga cattccraag aagattctcc cgt            33

<210> SEQ ID NO 132
<211> LENGTH: 33
<212> TYPE: DNA
<213> ORGANISM: Homo Sapiens

<400> SEQUENCE: 132
gcaactacaa gtgcacrggg cctagacatg gac            33

<210> SEQ ID NO 133
<211> LENGTH: 33
<212> TYPE: DNA
<213> ORGANISM: Homo Sapiens

<400> SEQUENCE: 133
```
acaagttgct taccacraag aatgtagtga aga                                    33

<210> SEQ ID NO 134
<211> LENGTH: 33
<212> TYPE: DNA
<213> ORGANISM: Homo Sapiens

<400> SEQUENCE: 134
agtattttgt tagttargag atccaatact tta                                    33

<210> SEQ ID NO 135
<211> LENGTH: 33
<212> TYPE: DNA
<213> ORGANISM: Homo Sapiens

<400> SEQUENCE: 135
aggtcagggt ccttcawgtg gtagctttga gtt                                    33

<210> SEQ ID NO 136
<211> LENGTH: 33
<212> TYPE: DNA
<213> ORGANISM: Homo Sapiens

<400> SEQUENCE: 136
agtgggtatg agtgaaygat ttacttagta cat                                    33

<210> SEQ ID NO 137
<211> LENGTH: 33
<212> TYPE: DNA
<213> ORGANISM: Homo Sapiens

<400> SEQUENCE: 137
gcaaaattga ggcagartca taacagacag tat                                    33

<210> SEQ ID NO 138
<211> LENGTH: 33
<212> TYPE: DNA
<213> ORGANISM: Homo Sapiens

<400> SEQUENCE: 138
tggttactta ctgacartat attgtgttgc ttt                                    33

<210> SEQ ID NO 139
<211> LENGTH: 33
<212> TYPE: DNA
<213> ORGANISM: Homo Sapiens

<400> SEQUENCE: 139
acatgtgtaa gaggccyggc aaagtgcctg tta                                    33

<210> SEQ ID NO 140
<211> LENGTH: 33
<212> TYPE: DNA
<213> ORGANISM: Homo Sapiens

<400> SEQUENCE: 140
gaggctgtta ttaaccraac ctcctggctg ggc                                    33

<210> SEQ ID NO 141
<211> LENGTH: 33
<212> TYPE: DNA
<213> ORGANISM: Homo Sapiens

```
<400> SEQUENCE: 141
accttcagta agtgacycac tctctcccca gtc                                33

<210> SEQ ID NO 142
<211> LENGTH: 33
<212> TYPE: DNA
<213> ORGANISM: Homo Sapiens

<400> SEQUENCE: 142
tctgggtaag gactggrata gcattcattc agc                                33

<210> SEQ ID NO 143
<211> LENGTH: 33
<212> TYPE: DNA
<213> ORGANISM: Homo Sapiens

<400> SEQUENCE: 143
aaaagcaaag ccaacaraac tctccagtct att                                33

<210> SEQ ID NO 144
<211> LENGTH: 33
<212> TYPE: DNA
<213> ORGANISM: Homo Sapiens

<400> SEQUENCE: 144
attctgggca gttagawcat caataggtga gta                                33

<210> SEQ ID NO 145
<211> LENGTH: 33
<212> TYPE: DNA
<213> ORGANISM: Homo Sapiens

<400> SEQUENCE: 145
atgaaggact tacgcawcta ttttggagat tca                                33

<210> SEQ ID NO 146
<211> LENGTH: 33
<212> TYPE: DNA
<213> ORGANISM: Homo Sapiens

<400> SEQUENCE: 146
tccctgtgtc acttccratg cctcctgaat aac                                33

<210> SEQ ID NO 147
<211> LENGTH: 33
<212> TYPE: DNA
<213> ORGANISM: Homo Sapiens

<400> SEQUENCE: 147
ttttgaggag aaaaaaytta gtacagagca aat                                33

<210> SEQ ID NO 148
<211> LENGTH: 33
<212> TYPE: DNA
<213> ORGANISM: Homo Sapiens

<400> SEQUENCE: 148
caacacttta cttagaygct ttgcccaggt tac                                33

<210> SEQ ID NO 149
<211> LENGTH: 33
<212> TYPE: DNA
<213> ORGANISM: Homo Sapiens
```

<400> SEQUENCE: 149
agagaattct caatgarcag cttcttattc cct                                    33

<210> SEQ ID NO 150
<211> LENGTH: 33
<212> TYPE: DNA
<213> ORGANISM: Homo Sapiens

<400> SEQUENCE: 150
caacagcaaa accttayaga ttatgtacat atg                                    33

<210> SEQ ID NO 151
<211> LENGTH: 33
<212> TYPE: DNA
<213> ORGANISM: Homo Sapiens

<400> SEQUENCE: 151
tacagtgact aaagatsagt ggttgccggg ctc                                    33

<210> SEQ ID NO 152
<211> LENGTH: 33
<212> TYPE: DNA
<213> ORGANISM: Homo Sapiens

<400> SEQUENCE: 152
aatcatgact acataaygga gtagaatgca aaa                                    33

<210> SEQ ID NO 153
<211> LENGTH: 33
<212> TYPE: DNA
<213> ORGANISM: Homo Sapiens

<400> SEQUENCE: 153
tgttcactgt tttgaayaaa gcactgatct aaa                                    33

<210> SEQ ID NO 154
<211> LENGTH: 33
<212> TYPE: DNA
<213> ORGANISM: Homo Sapiens

<400> SEQUENCE: 154
ctcttacatt ccttcaygta cactgctatt aaa                                    33

<210> SEQ ID NO 155
<211> LENGTH: 33
<212> TYPE: DNA
<213> ORGANISM: Homo Sapiens

<400> SEQUENCE: 155
gcggcagcag ctgtaakcag gcaacttggg ggt                                    33

<210> SEQ ID NO 156
<211> LENGTH: 33
<212> TYPE: DNA
<213> ORGANISM: Homo Sapiens

<400> SEQUENCE: 156
gtgatactct gtcacaraat taacaacaga ttg                                    33

<210> SEQ ID NO 157
<211> LENGTH: 33
<212> TYPE: DNA

<213> ORGANISM: Homo Sapiens

<400> SEQUENCE: 157
ctacacgttt cactcarctt ctgcatttgt gaa       33

<210> SEQ ID NO 158
<211> LENGTH: 33
<212> TYPE: DNA
<213> ORGANISM: Homo Sapiens

<400> SEQUENCE: 158
tgaatgaatg aatgcasaaa tccccatcat ttc       33

<210> SEQ ID NO 159
<211> LENGTH: 33
<212> TYPE: DNA
<213> ORGANISM: Homo Sapiens

<400> SEQUENCE: 159
aggaggctag tgtcaartag cgctgccaag tgt       33

<210> SEQ ID NO 160
<211> LENGTH: 33
<212> TYPE: DNA
<213> ORGANISM: Homo Sapiens

<400> SEQUENCE: 160
tttcctgcaa tgaagasaga ttgattcaga aat       33

<210> SEQ ID NO 161
<211> LENGTH: 33
<212> TYPE: DNA
<213> ORGANISM: Homo Sapiens

<400> SEQUENCE: 161
tgtaggagca taaaggycaa catgggccac tca       33

<210> SEQ ID NO 162
<211> LENGTH: 33
<212> TYPE: DNA
<213> ORGANISM: Homo Sapiens

<400> SEQUENCE: 162
catcatatgt aattacrgga gtataaatta aaa       33

<210> SEQ ID NO 163
<211> LENGTH: 33
<212> TYPE: DNA
<213> ORGANISM: Homo Sapiens

<400> SEQUENCE: 163
atacttcatg agaaaargta cagtaagcag ccc       33

<210> SEQ ID NO 164
<211> LENGTH: 33
<212> TYPE: DNA
<213> ORGANISM: Homo Sapiens

<400> SEQUENCE: 164
ttcattagtt aataaasagc tattggacgt tct       33

<210> SEQ ID NO 165
<211> LENGTH: 33

```
<212> TYPE: DNA
<213> ORGANISM: Homo Sapiens

<400> SEQUENCE: 165
ttttaaggag tcacaaytca agagaagttc aca                              33

<210> SEQ ID NO 166
<211> LENGTH: 33
<212> TYPE: DNA
<213> ORGANISM: Homo Sapiens

<400> SEQUENCE: 166
ggcagcatat gagttaygaa ctgcttcttt atc                              33

<210> SEQ ID NO 167
<211> LENGTH: 33
<212> TYPE: DNA
<213> ORGANISM: Homo Sapiens

<400> SEQUENCE: 167
ctctcatgaa tctgaasggc agcatatgag tta                              33

<210> SEQ ID NO 168
<211> LENGTH: 33
<212> TYPE: DNA
<213> ORGANISM: Homo Sapiens

<400> SEQUENCE: 168
aagatggcag agccaaytgg aaaccagatc acg                              33

<210> SEQ ID NO 169
<211> LENGTH: 33
<212> TYPE: DNA
<213> ORGANISM: Homo Sapiens

<400> SEQUENCE: 169
gcccatgaat acccaawgtt tatcttccac tta                              33

<210> SEQ ID NO 170
<211> LENGTH: 33
<212> TYPE: DNA
<213> ORGANISM: Homo Sapiens

<400> SEQUENCE: 170
cagagaatac aaggtaraaa aaccagctga gct                              33

<210> SEQ ID NO 171
<211> LENGTH: 33
<212> TYPE: DNA
<213> ORGANISM: Homo Sapiens

<400> SEQUENCE: 171
gtctaaaata tgtaatraga agcataggtc agt                              33

<210> SEQ ID NO 172
<211> LENGTH: 33
<212> TYPE: DNA
<213> ORGANISM: Homo Sapiens

<400> SEQUENCE: 172
gaggacacca caggccraaa gctatcccaa gac                              33

<210> SEQ ID NO 173
```

```
<211> LENGTH: 33
<212> TYPE: DNA
<213> ORGANISM: Homo Sapiens

<400> SEQUENCE: 173
tctagcaaag ctgagcyctc tgccggcaaa agc                                33

<210> SEQ ID NO 174
<211> LENGTH: 33
<212> TYPE: DNA
<213> ORGANISM: Homo Sapiens

<400> SEQUENCE: 174
ctctgacact ttatgcygag ttgctaccat ttc                                33

<210> SEQ ID NO 175
<211> LENGTH: 33
<212> TYPE: DNA
<213> ORGANISM: Homo Sapiens

<400> SEQUENCE: 175
ctgtcttttc ttatgaragt ccaaacccct ctc                                33

<210> SEQ ID NO 176
<211> LENGTH: 33
<212> TYPE: DNA
<213> ORGANISM: Homo Sapiens

<400> SEQUENCE: 176
tacactcttt aggccaytct ataatgatag ata                                33

<210> SEQ ID NO 177
<211> LENGTH: 33
<212> TYPE: DNA
<213> ORGANISM: Homo Sapiens

<400> SEQUENCE: 177
gcatatgatg atcctgyatg aaggagaatc aac                                33

<210> SEQ ID NO 178
<211> LENGTH: 33
<212> TYPE: DNA
<213> ORGANISM: Homo Sapiens

<400> SEQUENCE: 178
tgtcctagca cagaaaygga gtatgaattt tgt                                33

<210> SEQ ID NO 179
<211> LENGTH: 33
<212> TYPE: DNA
<213> ORGANISM: Homo Sapiens

<400> SEQUENCE: 179
tcaggctaca aatagayatg ggtgctgggt aga                                33

<210> SEQ ID NO 180
<211> LENGTH: 33
<212> TYPE: DNA
<213> ORGANISM: Homo Sapiens

<400> SEQUENCE: 180
aataaaatgt aggtatraaa agtagaagag tct                                33
```

```
<210> SEQ ID NO 181
<211> LENGTH: 33
<212> TYPE: DNA
<213> ORGANISM: Homo Sapiens

<400> SEQUENCE: 181
atagcaactt tacacamaaa tgggcctga ttt                                    33

<210> SEQ ID NO 182
<211> LENGTH: 33
<212> TYPE: DNA
<213> ORGANISM: Homo Sapiens

<400> SEQUENCE: 182
ttgtcttact gatggaygct ttttgatgtt ttc                                   33

<210> SEQ ID NO 183
<211> LENGTH: 33
<212> TYPE: DNA
<213> ORGANISM: Homo Sapiens

<400> SEQUENCE: 183
gtaaaaccca aagctayaca aaccttagaa gaa                                   33

<210> SEQ ID NO 184
<211> LENGTH: 33
<212> TYPE: DNA
<213> ORGANISM: Homo Sapiens

<400> SEQUENCE: 184
ttttccactc aaaataygca agagttctgt tac                                   33

<210> SEQ ID NO 185
<211> LENGTH: 33
<212> TYPE: DNA
<213> ORGANISM: Homo Sapiens

<400> SEQUENCE: 185
tgattaagaa acactgrcaa ttgaaaggga ata                                   33

<210> SEQ ID NO 186
<211> LENGTH: 33
<212> TYPE: DNA
<213> ORGANISM: Homo Sapiens

<400> SEQUENCE: 186
atctatgtga gtcatgmaag gaaatagagg aga                                   33

<210> SEQ ID NO 187
<211> LENGTH: 33
<212> TYPE: DNA
<213> ORGANISM: Homo Sapiens

<400> SEQUENCE: 187
tagagatgac tgaatgycaa aatagaaggt caa                                   33

<210> SEQ ID NO 188
<211> LENGTH: 33
<212> TYPE: DNA
<213> ORGANISM: Homo Sapiens

<400> SEQUENCE: 188
tgccaacacc atagaargta cttacacaaa cct                                   33
```

<210> SEQ ID NO 189
<211> LENGTH: 33
<212> TYPE: DNA
<213> ORGANISM: Homo Sapiens

<400> SEQUENCE: 189
gcattatccc atgaccycca aacagaacac aca          33

<210> SEQ ID NO 190
<211> LENGTH: 33
<212> TYPE: DNA
<213> ORGANISM: Homo Sapiens

<400> SEQUENCE: 190
gactcataaa acccacygta aggacaatgt taa          33

<210> SEQ ID NO 191
<211> LENGTH: 33
<212> TYPE: DNA
<213> ORGANISM: Homo Sapiens

<400> SEQUENCE: 191
gaagagtcat actaacrcat ctaaagtcta tgc          33

<210> SEQ ID NO 192
<211> LENGTH: 33
<212> TYPE: DNA
<213> ORGANISM: Homo Sapiens

<400> SEQUENCE: 192
tcctttgtaa atgaaaygac agtgtagata tat          33

<210> SEQ ID NO 193
<211> LENGTH: 33
<212> TYPE: DNA
<213> ORGANISM: Homo Sapiens

<400> SEQUENCE: 193
tttggaatta gaagacyctg cattaccatt tac          33

<210> SEQ ID NO 194
<211> LENGTH: 33
<212> TYPE: DNA
<213> ORGANISM: Homo Sapiens

<400> SEQUENCE: 194
ttttgtagca ttactaygat ctgaattcca tac          33

<210> SEQ ID NO 195
<211> LENGTH: 33
<212> TYPE: DNA
<213> ORGANISM: Homo Sapiens

<400> SEQUENCE: 195
aggcagttgt tttgtcyaat catttgggtc tca          33

<210> SEQ ID NO 196
<211> LENGTH: 33
<212> TYPE: DNA
<213> ORGANISM: Homo Sapiens

<400> SEQUENCE: 196
tactcactaa gaactayagg cagaaacagc act          33

<210> SEQ ID NO 197
<211> LENGTH: 33
<212> TYPE: DNA
<213> ORGANISM: Homo Sapiens

<400> SEQUENCE: 197
ccagatgggt ctgttaygat ttcagccacc ttg                          33

<210> SEQ ID NO 198
<211> LENGTH: 33
<212> TYPE: DNA
<213> ORGANISM: Homo Sapiens

<400> SEQUENCE: 198
gcagctcatt gcagtargac agatttaaac aac                          33

<210> SEQ ID NO 199
<211> LENGTH: 33
<212> TYPE: DNA
<213> ORGANISM: Homo Sapiens

<400> SEQUENCE: 199
tccctgcact tcacagrcta ttacgtggga cat                          33

<210> SEQ ID NO 200
<211> LENGTH: 33
<212> TYPE: DNA
<213> ORGANISM: Homo Sapiens

<400> SEQUENCE: 200
aactcagcct ccatacwcaa gtgaggcaga aaa                          33

<210> SEQ ID NO 201
<211> LENGTH: 33
<212> TYPE: DNA
<213> ORGANISM: Homo Sapiens

<400> SEQUENCE: 201
tttatattat tgatcaygta aataaaaatg cat                          33

<210> SEQ ID NO 202
<211> LENGTH: 33
<212> TYPE: DNA
<213> ORGANISM: Homo Sapiens

<400> SEQUENCE: 202
gatccaaaat tactcayata tttggcagtt gtg                          33

<210> SEQ ID NO 203
<211> LENGTH: 33
<212> TYPE: DNA
<213> ORGANISM: Homo Sapiens

<400> SEQUENCE: 203
gcttattagt caaacaycat ttttatcata gct                          33

<210> SEQ ID NO 204
<211> LENGTH: 33
<212> TYPE: DNA
<213> ORGANISM: Homo Sapiens

<400> SEQUENCE: 204

```
acataaggtg cttaggraaa aaagtgtaac cat        33

<210> SEQ ID NO 205
<211> LENGTH: 33
<212> TYPE: DNA
<213> ORGANISM: Homo Sapiens

<400> SEQUENCE: 205
aacctaggtt gtaattygta tcactgcatt ttc        33

<210> SEQ ID NO 206
<211> LENGTH: 33
<212> TYPE: DNA
<213> ORGANISM: Homo Sapiens

<400> SEQUENCE: 206
atatctctaa tatgctrtcg tgaacatctg gtc        33

<210> SEQ ID NO 207
<211> LENGTH: 33
<212> TYPE: DNA
<213> ORGANISM: Homo Sapiens

<400> SEQUENCE: 207
ttattgtgca tcgttargag cagaaccaga tag        33

<210> SEQ ID NO 208
<211> LENGTH: 33
<212> TYPE: DNA
<213> ORGANISM: Homo Sapiens

<400> SEQUENCE: 208
aatgttttta aactacygca acaggcctga gat        33

<210> SEQ ID NO 209
<211> LENGTH: 33
<212> TYPE: DNA
<213> ORGANISM: Homo Sapiens

<400> SEQUENCE: 209
ggcaccagca tctgaartta aatgtgataa cat        33

<210> SEQ ID NO 210
<211> LENGTH: 33
<212> TYPE: DNA
<213> ORGANISM: Homo Sapiens

<400> SEQUENCE: 210
actccagcct tgcacayctg gtcttttccc aca        33

<210> SEQ ID NO 211
<211> LENGTH: 33
<212> TYPE: DNA
<213> ORGANISM: Homo Sapiens

<400> SEQUENCE: 211
gtgaaagaag acagacrgaa agacttcata ttg        33

<210> SEQ ID NO 212
<211> LENGTH: 33
<212> TYPE: DNA
<213> ORGANISM: Homo Sapiens

<400> SEQUENCE: 212
```
tctcatgttg aaatccmagc tcttaaggac aaa                        33

<210> SEQ ID NO 213
<211> LENGTH: 33
<212> TYPE: DNA
<213> ORGANISM: Homo Sapiens

<400> SEQUENCE: 213
attggcaaat actacarcca aaatagccct cct                        33

<210> SEQ ID NO 214
<211> LENGTH: 33
<212> TYPE: DNA
<213> ORGANISM: Homo Sapiens

<400> SEQUENCE: 214
cagtacattt attgcargtt tattttatgc tta                        33

<210> SEQ ID NO 215
<211> LENGTH: 33
<212> TYPE: DNA
<213> ORGANISM: Homo Sapiens

<400> SEQUENCE: 215
gtagggaaga caaaaarggt atgaaagtta gag                        33

<210> SEQ ID NO 216
<211> LENGTH: 33
<212> TYPE: DNA
<213> ORGANISM: Homo Sapiens

<400> SEQUENCE: 216
atgttacttt caagtcrctt cccattctgg ttc                        33

<210> SEQ ID NO 217
<211> LENGTH: 33
<212> TYPE: DNA
<213> ORGANISM: Homo Sapiens

<400> SEQUENCE: 217
ctatttctat aaccaamtct tatggataat agc                        33

<210> SEQ ID NO 218
<211> LENGTH: 33
<212> TYPE: DNA
<213> ORGANISM: Homo Sapiens

<400> SEQUENCE: 218
acccaaggaa caagackctc atggtaccaa ctc                        33

<210> SEQ ID NO 219
<211> LENGTH: 33
<212> TYPE: DNA
<213> ORGANISM: Homo Sapiens

<400> SEQUENCE: 219
atcacaactg gcttgcrgac ttaaccacca agg                        33

<210> SEQ ID NO 220
<211> LENGTH: 33
<212> TYPE: DNA
<213> ORGANISM: Homo Sapiens

```
<400> SEQUENCE: 220
tcctagaacc ctgagayatt tatgtgaaaa agt                                    33

<210> SEQ ID NO 221
<211> LENGTH: 33
<212> TYPE: DNA
<213> ORGANISM: Homo Sapiens

<400> SEQUENCE: 221
attgtgtttg tattcayagg ctattgtagc tta                                    33

<210> SEQ ID NO 222
<211> LENGTH: 33
<212> TYPE: DNA
<213> ORGANISM: Homo Sapiens

<400> SEQUENCE: 222
ttatggacca tgtcaargga ttattttctt cat                                    33

<210> SEQ ID NO 223
<211> LENGTH: 33
<212> TYPE: DNA
<213> ORGANISM: Homo Sapiens

<400> SEQUENCE: 223
gagctgccaa tcacctraac aatcaccttc taa                                    33

<210> SEQ ID NO 224
<211> LENGTH: 33
<212> TYPE: DNA
<213> ORGANISM: Homo Sapiens

<400> SEQUENCE: 224
gaaagtgaag ggaatgraag tttgtgctga gcc                                    33

<210> SEQ ID NO 225
<211> LENGTH: 33
<212> TYPE: DNA
<213> ORGANISM: Homo Sapiens

<400> SEQUENCE: 225
tcttaaacaa ttcaackaag caagtgttat aaa                                    33

<210> SEQ ID NO 226
<211> LENGTH: 33
<212> TYPE: DNA
<213> ORGANISM: Homo Sapiens

<400> SEQUENCE: 226
caaaatacca tagctcyctt aaccattctt tac                                    33

<210> SEQ ID NO 227
<211> LENGTH: 33
<212> TYPE: DNA
<213> ORGANISM: Homo Sapiens

<400> SEQUENCE: 227
gtagccccag cccaaaaraga agagcaaact gga                                   33

<210> SEQ ID NO 228
<211> LENGTH: 33
<212> TYPE: DNA
<213> ORGANISM: Homo Sapiens
```

-continued

```
<400> SEQUENCE: 228
tgaagcttat ttgggcrcag ggtgtttgtt gtt                                    33

<210> SEQ ID NO 229
<211> LENGTH: 33
<212> TYPE: DNA
<213> ORGANISM: Homo Sapiens

<400> SEQUENCE: 229
tccaaggacc ttgttcraag gtaagactca tgc                                    33

<210> SEQ ID NO 230
<211> LENGTH: 33
<212> TYPE: DNA
<213> ORGANISM: Homo Sapiens

<400> SEQUENCE: 230
aaattgccga gtaacaygat ttcagtaaca tgt                                    33

<210> SEQ ID NO 231
<211> LENGTH: 33
<212> TYPE: DNA
<213> ORGANISM: Homo Sapiens

<400> SEQUENCE: 231
acgtggtgct aaatgasatg gagaccaatc agg                                    33

<210> SEQ ID NO 232
<211> LENGTH: 33
<212> TYPE: DNA
<213> ORGANISM: Homo Sapiens

<400> SEQUENCE: 232
atggtgacaa ttaacaytga agtgaatagg cca                                    33

<210> SEQ ID NO 233
<211> LENGTH: 33
<212> TYPE: DNA
<213> ORGANISM: Homo Sapiens

<400> SEQUENCE: 233
caataacact cttaatyaca catttccttt tag                                    33

<210> SEQ ID NO 234
<211> LENGTH: 33
<212> TYPE: DNA
<213> ORGANISM: Homo Sapiens

<400> SEQUENCE: 234
ttgaactaga cagtaaygct cagtgtgttg ttt                                    33

<210> SEQ ID NO 235
<211> LENGTH: 33
<212> TYPE: DNA
<213> ORGANISM: Homo Sapiens

<400> SEQUENCE: 235
gtcttcctcc agagaastat gtgtcatgtg tag                                    33

<210> SEQ ID NO 236
<211> LENGTH: 33
<212> TYPE: DNA
```

<213> ORGANISM: Homo Sapiens

<400> SEQUENCE: 236
aaaaggctga ataggakaga gtttccccca cta    33

<210> SEQ ID NO 237
<211> LENGTH: 33
<212> TYPE: DNA
<213> ORGANISM: Homo Sapiens

<400> SEQUENCE: 237
gtctaaataa caagaayaga tgagctcgcg aga    33

<210> SEQ ID NO 238
<211> LENGTH: 33
<212> TYPE: DNA
<213> ORGANISM: Homo Sapiens

<400> SEQUENCE: 238
gggcacaatt gatctcrcta cccagacact gag    33

<210> SEQ ID NO 239
<211> LENGTH: 33
<212> TYPE: DNA
<213> ORGANISM: Homo Sapiens

<400> SEQUENCE: 239
gctgctcctt gaccttsaac aacattcaga aca    33

<210> SEQ ID NO 240
<211> LENGTH: 33
<212> TYPE: DNA
<213> ORGANISM: Homo Sapiens

<400> SEQUENCE: 240
aaacatctct ctacgtkaag gtaatattct gca    33

<210> SEQ ID NO 241
<211> LENGTH: 33
<212> TYPE: DNA
<213> ORGANISM: Homo Sapiens

<400> SEQUENCE: 241
catgtgtaca cctatayaat aaacctgcac gtt    33

<210> SEQ ID NO 242
<211> LENGTH: 33
<212> TYPE: DNA
<213> ORGANISM: Homo Sapiens

<400> SEQUENCE: 242
tcttcaagtt ctccgargct agggccagag tag    33

<210> SEQ ID NO 243
<211> LENGTH: 33
<212> TYPE: DNA
<213> ORGANISM: Homo Sapiens

<400> SEQUENCE: 243
gaagacataa tgaacarcac aggcaaaagc cct    33

<210> SEQ ID NO 244
<211> LENGTH: 33

```
<212> TYPE: DNA
<213> ORGANISM: Homo Sapiens

<400> SEQUENCE: 244
tgacctctat gctggcsagt atctcccaga ccc                                33

<210> SEQ ID NO 245
<211> LENGTH: 33
<212> TYPE: DNA
<213> ORGANISM: Homo Sapiens

<400> SEQUENCE: 245
tggggaatcc tggacckcga ctacgctgca ctc                                33

<210> SEQ ID NO 246
<211> LENGTH: 33
<212> TYPE: DNA
<213> ORGANISM: Homo Sapiens

<400> SEQUENCE: 246
ttctcttaca cataaaktga tctcttcaag ttc                                33

<210> SEQ ID NO 247
<211> LENGTH: 33
<212> TYPE: DNA
<213> ORGANISM: Homo Sapiens

<400> SEQUENCE: 247
accaaaaata caaataragg caccctcttt cac                                33

<210> SEQ ID NO 248
<211> LENGTH: 33
<212> TYPE: DNA
<213> ORGANISM: Homo Sapiens

<400> SEQUENCE: 248
ttctctaccc cttgatyact cctctgaaga aaa                                33

<210> SEQ ID NO 249
<211> LENGTH: 33
<212> TYPE: DNA
<213> ORGANISM: Homo Sapiens

<400> SEQUENCE: 249
cagacatccc atctcgscag ccatatcttt ttc                                33

<210> SEQ ID NO 250
<211> LENGTH: 33
<212> TYPE: DNA
<213> ORGANISM: Homo Sapiens

<400> SEQUENCE: 250
agcaccaaag acattcrctg tgacttcaaa tgt                                33

<210> SEQ ID NO 251
<211> LENGTH: 33
<212> TYPE: DNA
<213> ORGANISM: Homo Sapiens

<400> SEQUENCE: 251 tctggcatt tcagtaayac accttatggt tagc                                33

<210> SEQ ID NO 252
<211> LENGTH: 33
```

<212> TYPE: DNA
<213> ORGANISM: Homo Sapiens

<400> SEQUENCE: 252
accatatgtt gggtcayaaa ataagtctta aaa                                   33

<210> SEQ ID NO 253
<211> LENGTH: 33
<212> TYPE: DNA
<213> ORGANISM: Homo Sapiens

<400> SEQUENCE: 253
agattttcat ccatggract cacttaaatt gag                                   33

<210> SEQ ID NO 254
<211> LENGTH: 33
<212> TYPE: DNA
<213> ORGANISM: Homo Sapiens

<400> SEQUENCE: 254
cagagctgct gccaccmaag tttatggatg cat                                   33

<210> SEQ ID NO 255
<211> LENGTH: 33
<212> TYPE: DNA
<213> ORGANISM: Homo Sapiens

<400> SEQUENCE: 255
gaattgaaga actaaaygga gtaagagaag gag                                   33

<210> SEQ ID NO 256
<211> LENGTH: 33
<212> TYPE: DNA
<213> ORGANISM: Homo Sapiens

<400> SEQUENCE: 256
gccaatgtgg acttcgkaac ttccagaatc cag                                   33

<210> SEQ ID NO 257
<211> LENGTH: 33
<212> TYPE: DNA
<213> ORGANISM: Homo Sapiens

<400> SEQUENCE: 257
agaagccaag actgagmagg aatcagtaac ttt                                   33

<210> SEQ ID NO 258
<211> LENGTH: 33
<212> TYPE: DNA
<213> ORGANISM: Homo Sapiens

<400> SEQUENCE: 258
ccttaccatt gtatcaygga gaccatccca tga                                   33

<210> SEQ ID NO 259
<211> LENGTH: 33
<212> TYPE: DNA
<213> ORGANISM: Homo Sapiens

<400> SEQUENCE: 259
tgaaggaatg ggtcgaygga aacatatttg ata                                   33

<210> SEQ ID NO 260

-continued

```
<211> LENGTH: 33
<212> TYPE: DNA
<213> ORGANISM: Homo Sapiens

<400> SEQUENCE: 260
tggaatattt gttaackgaa gcccagaatt gga                                33

<210> SEQ ID NO 261
<211> LENGTH: 33
<212> TYPE: DNA
<213> ORGANISM: Homo Sapiens

<400> SEQUENCE: 261
actcgttcat tcatgcrcta ttggacatca ttt                                33

<210> SEQ ID NO 262
<211> LENGTH: 33
<212> TYPE: DNA
<213> ORGANISM: Homo Sapiens

<400> SEQUENCE: 262
tttgtctttg actttcraca gtttcaatat aat                                33

<210> SEQ ID NO 263
<211> LENGTH: 33
<212> TYPE: DNA
<213> ORGANISM: Homo Sapiens

<400> SEQUENCE: 263
caaccacatt tggcgargtt aatccagctt tcc                                33

<210> SEQ ID NO 264
<211> LENGTH: 33
<212> TYPE: DNA
<213> ORGANISM: Homo Sapiens

<400> SEQUENCE: 264
actgagtccc aatgggyaac tgattgcctc ttt                                33

<210> SEQ ID NO 265
<211> LENGTH: 33
<212> TYPE: DNA
<213> ORGANISM: Homo Sapiens

<400> SEQUENCE: 265
atgatctggg gaatgayatg aaattggcct aaa                                33

<210> SEQ ID NO 266
<211> LENGTH: 33
<212> TYPE: DNA
<213> ORGANISM: Homo Sapiens

<400> SEQUENCE: 266
atgtagattt actgagrcta atcagactca caa                                33

<210> SEQ ID NO 267
<211> LENGTH: 33
<212> TYPE: DNA
<213> ORGANISM: Homo Sapiens

<400> SEQUENCE: 267
ctccattgta cagaatraga acagagaggc aca                                33
```

```
<210> SEQ ID NO 268
<211> LENGTH: 33
<212> TYPE: DNA
<213> ORGANISM: Homo Sapiens

<400> SEQUENCE: 268
cggctctaat ttctcaygtc tttcaaggag act                          33

<210> SEQ ID NO 269
<211> LENGTH: 33
<212> TYPE: DNA
<213> ORGANISM: Homo Sapiens

<400> SEQUENCE: 269
aaacgtgaat ttaaggwcag cacaacaatc cag                          33

<210> SEQ ID NO 270
<211> LENGTH: 33
<212> TYPE: DNA
<213> ORGANISM: Homo Sapiens

<400> SEQUENCE: 270
tcagggaaat tcacaargac acagggaaca ccc                          33

<210> SEQ ID NO 271
<211> LENGTH: 33
<212> TYPE: DNA
<213> ORGANISM: Homo Sapiens

<400> SEQUENCE: 271
catcagtctc gcccccsaca ggtaatcgct gtt                          33

<210> SEQ ID NO 272
<211> LENGTH: 33
<212> TYPE: DNA
<213> ORGANISM: Homo Sapiens

<400> SEQUENCE: 272
tggacagctg agttggkatg agttggagaa cag                          33

<210> SEQ ID NO 273
<211> LENGTH: 33
<212> TYPE: DNA
<213> ORGANISM: Homo Sapiens

<400> SEQUENCE: 273
ttgtatgata cctacaktga gtctctccta agc                          33

<210> SEQ ID NO 274
<211> LENGTH: 33
<212> TYPE: DNA
<213> ORGANISM: Homo Sapiens

<400> SEQUENCE: 274
gcctcaggaa ctcagaygtc caatttacat gta                          33

<210> SEQ ID NO 275
<211> LENGTH: 33
<212> TYPE: DNA
<213> ORGANISM: Homo Sapiens

<400> SEQUENCE: 275
gtaatgaggg gtaaaawtca tagacaaaca cac                          33
```

<210> SEQ ID NO 276
<211> LENGTH: 33
<212> TYPE: DNA
<213> ORGANISM: Homo Sapiens

<400> SEQUENCE: 276
aacctgagct ccttacyaaa ataaagctgt ctt                33

<210> SEQ ID NO 277
<211> LENGTH: 33
<212> TYPE: DNA
<213> ORGANISM: Homo Sapiens

<400> SEQUENCE: 277
tcttacaata gagatartaa ttcctggagt tgt                33

<210> SEQ ID NO 278
<211> LENGTH: 33
<212> TYPE: DNA
<213> ORGANISM: Homo Sapiens

<400> SEQUENCE: 278
tgcaagtcag ttagaamctt tgatattatt cta                33

<210> SEQ ID NO 279
<211> LENGTH: 33
<212> TYPE: DNA
<213> ORGANISM: Homo Sapiens

<400> SEQUENCE: 279
aaagccactg gtatcarata ttttactata aga                33

<210> SEQ ID NO 280
<211> LENGTH: 33
<212> TYPE: DNA
<213> ORGANISM: Homo Sapiens

<400> SEQUENCE: 280
aaaatgattt tgattaygac agctttcaat aga                33

<210> SEQ ID NO 281
<211> LENGTH: 33
<212> TYPE: DNA
<213> ORGANISM: Homo Sapiens

<400> SEQUENCE: 281
ttaactgagt gtaacayagt aggtgctcaa taa                33

<210> SEQ ID NO 282
<211> LENGTH: 33
<212> TYPE: DNA
<213> ORGANISM: Homo Sapiens

<400> SEQUENCE: 282
aaagcaggtc actgacsaaa atgtttacag tga                33

<210> SEQ ID NO 283
<211> LENGTH: 33
<212> TYPE: DNA
<213> ORGANISM: Homo Sapiens

<400> SEQUENCE: 283
aaatacaaat aattgawgtg atagctatcc tga                33

<210> SEQ ID NO 284
<211> LENGTH: 33
<212> TYPE: DNA
<213> ORGANISM: Homo Sapiens

<400> SEQUENCE: 284
tctttccttg gcaacastga ggatttgtta tgg                                    33

<210> SEQ ID NO 285
<211> LENGTH: 33
<212> TYPE: DNA
<213> ORGANISM: Homo Sapiens

<400> SEQUENCE: 285
tgcagaataa caaaaaygta cgcaaataaa tat                                    33

<210> SEQ ID NO 286
<211> LENGTH: 33
<212> TYPE: DNA
<213> ORGANISM: Homo Sapiens

<400> SEQUENCE: 286
ggagataaaa tggataygtg aatttagtca tca                                    33

<210> SEQ ID NO 287
<211> LENGTH: 33
<212> TYPE: DNA
<213> ORGANISM: Homo Sapiens

<400> SEQUENCE: 287
ataatttctc aattgcwatt tcaggccttt taa                                    33

<210> SEQ ID NO 288
<211> LENGTH: 33
<212> TYPE: DNA
<213> ORGANISM: Homo Sapiens

<400> SEQUENCE: 288
tgtcctctcc cccaacraag agaaatgcat tag                                    33

<210> SEQ ID NO 289
<211> LENGTH: 33
<212> TYPE: DNA
<213> ORGANISM: Homo Sapiens

<400> SEQUENCE: 289
agactgttga gtctgcrcgt ccttgttcct gcg                                    33

<210> SEQ ID NO 290
<211> LENGTH: 33
<212> TYPE: DNA
<213> ORGANISM: Homo Sapiens

<400> SEQUENCE: 290
aaaaactgga gatccaytgg aaaaacctca agc                                    33

<210> SEQ ID NO 291
<211> LENGTH: 33
<212> TYPE: DNA
<213> ORGANISM: Homo Sapiens

<400> SEQUENCE: 291
tggcacagaa gacaaaygct ggggaggaaa agg                                    33

<210> SEQ ID NO 292
<211> LENGTH: 33
<212> TYPE: DNA
<213> ORGANISM: Homo Sapiens

<400> SEQUENCE: 292
gaagtgtttg gtggcarcag atgctcaaga cag                                    33

<210> SEQ ID NO 293
<211> LENGTH: 33
<212> TYPE: DNA
<213> ORGANISM: Homo Sapiens

<400> SEQUENCE: 293
ttagtataaa aagtaargca taggccgggc gtg                                    33

<210> SEQ ID NO 294
<211> LENGTH: 33
<212> TYPE: DNA
<213> ORGANISM: Homo Sapiens

<400> SEQUENCE: 294
tttattcatg gactaamatc cttgtctgac ttt                                    33

<210> SEQ ID NO 295
<211> LENGTH: 33
<212> TYPE: DNA
<213> ORGANISM: Homo Sapiens

<400> SEQUENCE: 295
tgtctccagt gtggagrata tacttcaaca att                                    33

<210> SEQ ID NO 296
<211> LENGTH: 33
<212> TYPE: DNA
<213> ORGANISM: Homo Sapiens

<400> SEQUENCE: 296
ttctagcctt ttagtayggc aaatcatatt tta                                    33

<210> SEQ ID NO 297
<211> LENGTH: 33
<212> TYPE: DNA
<213> ORGANISM: Homo Sapiens

<400> SEQUENCE: 297
tgtgaaaatt cactgaratt tatgctcaag att                                    33

<210> SEQ ID NO 298
<211> LENGTH: 33
<212> TYPE: DNA
<213> ORGANISM: Homo Sapiens

<400> SEQUENCE: 298
aagaccaatg cagacamacg ttttcgagtg gtt                                    33

<210> SEQ ID NO 299
<211> LENGTH: 33
<212> TYPE: DNA
<213> ORGANISM: Homo Sapiens

<400> SEQUENCE: 299
attactcttt cagatgrcag tatgcttttc tct					33

<210> SEQ ID NO 300
<211> LENGTH: 33
<212> TYPE: DNA
<213> ORGANISM: Homo Sapiens

<400> SEQUENCE: 300
tttttgcatt tacatayatc aagttaaaga agt					33

<210> SEQ ID NO 301
<211> LENGTH: 33
<212> TYPE: DNA
<213> ORGANISM: Homo Sapiens

<400> SEQUENCE: 301
ttccagtctt cacagaktaa ctttgtctgg aaa					33

<210> SEQ ID NO 302
<211> LENGTH: 33
<212> TYPE: DNA
<213> ORGANISM: Homo Sapiens

<400> SEQUENCE: 302
tttcaaaaac attcctwaac ctttatctag cta					33

<210> SEQ ID NO 303
<211> LENGTH: 33
<212> TYPE: DNA
<213> ORGANISM: Homo Sapiens

<400> SEQUENCE: 303
tattatagag agcccgsaaa taaattcatg cac					33

<210> SEQ ID NO 304
<211> LENGTH: 33
<212> TYPE: DNA
<213> ORGANISM: Homo Sapiens

<400> SEQUENCE: 304
cttatcagat taatgcracc ctgatagatc ccc					33

<210> SEQ ID NO 305
<211> LENGTH: 33
<212> TYPE: DNA
<213> ORGANISM: Homo Sapiens

<400> SEQUENCE: 305
aataggtttg taagtgsatt tattaccatc tcc					33

<210> SEQ ID NO 306
<211> LENGTH: 33
<212> TYPE: DNA
<213> ORGANISM: Homo Sapiens

<400> SEQUENCE: 306
tggaaatgaa tccctcycta atgtccgtag gaa					33

<210> SEQ ID NO 307
<211> LENGTH: 33
<212> TYPE: DNA
<213> ORGANISM: Homo Sapiens

<400> SEQUENCE: 307
aggatatatt catctcratt tttatagata ggc					33

<210> SEQ ID NO 308
<211> LENGTH: 33
<212> TYPE: DNA
<213> ORGANISM: Homo Sapiens

<400> SEQUENCE: 308
ttttgttact aaagaakagc tgccctgtta ctc					33

<210> SEQ ID NO 309
<211> LENGTH: 33
<212> TYPE: DNA
<213> ORGANISM: Homo Sapiens

<400> SEQUENCE: 309
tgttaggcca ttatgayaga tgaggggtcc cgc					33

<210> SEQ ID NO 310
<211> LENGTH: 33
<212> TYPE: DNA
<213> ORGANISM: Homo Sapiens

<400> SEQUENCE: 310
tatgggcaga actggaraag tctcaagggc tgg					33

<210> SEQ ID NO 311
<211> LENGTH: 33
<212> TYPE: DNA
<213> ORGANISM: Homo Sapiens

<400> SEQUENCE: 311
tcctaatcct tggaacycag gaatttgttg ggt					33

<210> SEQ ID NO 312
<211> LENGTH: 33
<212> TYPE: DNA
<213> ORGANISM: Homo Sapiens

<400> SEQUENCE: 312
acccttcaca catttayggt gcccatctga cat					33

<210> SEQ ID NO 313
<211> LENGTH: 33
<212> TYPE: DNA
<213> ORGANISM: Homo Sapiens

<400> SEQUENCE: 313
acctgaccaa ctgtcaytct ccaaagacac tta					33

<210> SEQ ID NO 314
<211> LENGTH: 33
<212> TYPE: DNA
<213> ORGANISM: Homo Sapiens

<400> SEQUENCE: 314
gggctgagag aactgayggg actcatcagg ctg					33

<210> SEQ ID NO 315
<211> LENGTH: 33
<212> TYPE: DNA
<213> ORGANISM: Homo Sapiens

```
<400> SEQUENCE: 315
catccatgaa tcatgarctc tttttaaact tta                              33

<210> SEQ ID NO 316
<211> LENGTH: 33
<212> TYPE: DNA
<213> ORGANISM: Homo Sapiens

<400> SEQUENCE: 316
gaaaatgatg ggtgaawgta gttaagacaa gtg                              33

<210> SEQ ID NO 317
<211> LENGTH: 33
<212> TYPE: DNA
<213> ORGANISM: Homo Sapiens

<400> SEQUENCE: 317
gaagacagaa aacagayggt cataatatat tct                              33

<210> SEQ ID NO 318
<211> LENGTH: 33
<212> TYPE: DNA
<213> ORGANISM: Homo Sapiens

<400> SEQUENCE: 318
ggggtagagg agagaasaaa aagttgacat tgg                              33

<210> SEQ ID NO 319
<211> LENGTH: 33
<212> TYPE: DNA
<213> ORGANISM: Homo Sapiens

<400> SEQUENCE: 319
gtaaagattg ccaacaytct aatccctgct gta                              33

<210> SEQ ID NO 320
<211> LENGTH: 33
<212> TYPE: DNA
<213> ORGANISM: Homo Sapiens

<400> SEQUENCE: 320
gagcaaatag cagatcrgaa aaggggctca ata                              33

<210> SEQ ID NO 321
<211> LENGTH: 33
<212> TYPE: DNA
<213> ORGANISM: Homo Sapiens

<400> SEQUENCE: 321
aaggaaaatg aagatcmaca ttaataattg aac                              33

<210> SEQ ID NO 322
<211> LENGTH: 33
<212> TYPE: DNA
<213> ORGANISM: Homo Sapiens

<400> SEQUENCE: 322
tttaattgtt tcttcaygta cagaaatgta gtc                              33

<210> SEQ ID NO 323
<211> LENGTH: 33
<212> TYPE: DNA
```

<213> ORGANISM: Homo Sapiens

<400> SEQUENCE: 323
gacaagacaa tgctggrcac atttggtgtt cac        33

<210> SEQ ID NO 324
<211> LENGTH: 33
<212> TYPE: DNA
<213> ORGANISM: Homo Sapiens

<400> SEQUENCE: 324
catctctaca aatatgraaa caaaaatagc agg        33

<210> SEQ ID NO 325
<211> LENGTH: 33
<212> TYPE: DNA
<213> ORGANISM: Homo Sapiens

<400> SEQUENCE: 325
atatctgtat gcattawgga atggctaaat cag        33

<210> SEQ ID NO 326
<211> LENGTH: 33
<212> TYPE: DNA
<213> ORGANISM: Homo Sapiens

<400> SEQUENCE: 326
tccctacaca ggcacarcct cttacattat caa        33

<210> SEQ ID NO 327
<211> LENGTH: 33
<212> TYPE: DNA
<213> ORGANISM: Homo Sapiens

<400> SEQUENCE: 327
cctaccccat cactcayggc agaaactaag gcc        33

<210> SEQ ID NO 328
<211> LENGTH: 33
<212> TYPE: DNA
<213> ORGANISM: Homo Sapiens

<400> SEQUENCE: 328
gcaaaacctg aaactcyatg taggaagcta tgt        33

<210> SEQ ID NO 329
<211> LENGTH: 33
<212> TYPE: DNA
<213> ORGANISM: Homo Sapiens

<400> SEQUENCE: 329
acagtttctt tttggcrata ggagaggagg tag        33

<210> SEQ ID NO 330
<211> LENGTH: 33
<212> TYPE: DNA
<213> ORGANISM: Homo Sapiens

<400> SEQUENCE: 330
ctagttacaa atcccawact tatgaaagaa gca        33

<210> SEQ ID NO 331
<211> LENGTH: 33

```
<212> TYPE: DNA
<213> ORGANISM: Homo Sapiens

<400> SEQUENCE: 331
aatgagtgtc tcatcaytaa aaatattgaa gtc                              33

<210> SEQ ID NO 332
<211> LENGTH: 33
<212> TYPE: DNA
<213> ORGANISM: Homo Sapiens

<400> SEQUENCE: 332
tgtctacttg cggtgarata cagccccaat tac                              33

<210> SEQ ID NO 333
<211> LENGTH: 33
<212> TYPE: DNA
<213> ORGANISM: Homo Sapiens

<400> SEQUENCE: 333
aatgaataat ttatgartca agagtcttcc ttg                              33

<210> SEQ ID NO 334
<211> LENGTH: 33
<212> TYPE: DNA
<213> ORGANISM: Homo Sapiens

<400> SEQUENCE: 334
aaccactgct atagagraaa gtttccaaag ttt                              33

<210> SEQ ID NO 335
<211> LENGTH: 33
<212> TYPE: DNA
<213> ORGANISM: Homo Sapiens

<400> SEQUENCE: 335
gtctccgtgg cattaaycca gacagacaat tcc                              33

<210> SEQ ID NO 336
<211> LENGTH: 33
<212> TYPE: DNA
<213> ORGANISM: Homo Sapiens

<400> SEQUENCE: 336
tgtcctctca acacttmaac tgaattccta cac                              33

<210> SEQ ID NO 337
<211> LENGTH: 33
<212> TYPE: DNA
<213> ORGANISM: Homo Sapiens

<400> SEQUENCE: 337
aggaaggaaa acctccraac atcagcaaag gaa                              33

<210> SEQ ID NO 338
<211> LENGTH: 33
<212> TYPE: DNA
<213> ORGANISM: Homo Sapiens

<400> SEQUENCE: 338
tcgagaaatc acatagragg aggagcaggt ggc                              33

<210> SEQ ID NO 339
```

-continued

```
<211> LENGTH: 33
<212> TYPE: DNA
<213> ORGANISM: Homo Sapiens

<400> SEQUENCE: 339
ttggatggta aaatagkcat agtcctctaa ata                               33

<210> SEQ ID NO 340
<211> LENGTH: 33
<212> TYPE: DNA
<213> ORGANISM: Homo Sapiens

<400> SEQUENCE: 340
cctctctgca cggaaayggc agttagaaaa act                               33

<210> SEQ ID NO 341
<211> LENGTH: 33
<212> TYPE: DNA
<213> ORGANISM: Homo Sapiens

<400> SEQUENCE: 341
tgaaaatggt aagagcraga cttattgtta tgc                               33

<210> SEQ ID NO 342
<211> LENGTH: 33
<212> TYPE: DNA
<213> ORGANISM: Homo Sapiens

<400> SEQUENCE: 342
ttgcagcctt ctgctgwatt tctgatctga gct                               33

<210> SEQ ID NO 343
<211> LENGTH: 33
<212> TYPE: DNA
<213> ORGANISM: Homo Sapiens

<400> SEQUENCE: 343
gctaaaaggt gcttccrgag tgagaggtgg taa                               33

<210> SEQ ID NO 344
<211> LENGTH: 33
<212> TYPE: DNA
<213> ORGANISM: Homo Sapiens

<400> SEQUENCE: 344
tcaaacaaca ccattgyatt ctcttaccat ctg                               33

<210> SEQ ID NO 345
<211> LENGTH: 33
<212> TYPE: DNA
<213> ORGANISM: Homo Sapiens

<400> SEQUENCE: 345
tctatatcta aggtcascat ttttcattat cag                               33

<210> SEQ ID NO 346
<211> LENGTH: 33
<212> TYPE: DNA
<213> ORGANISM: Homo Sapiens

<400> SEQUENCE: 346
tttcagtcat cactgargtt atttttaagg ttg                               33
```

```
<210> SEQ ID NO 347
<211> LENGTH: 33
<212> TYPE: DNA
<213> ORGANISM: Homo Sapiens

<400> SEQUENCE: 347
ctcttgtctt tagtcaycta gccaaccaaa cac                                   33

<210> SEQ ID NO 348
<211> LENGTH: 33
<212> TYPE: DNA
<213> ORGANISM: Homo Sapiens

<400> SEQUENCE: 348
atgtggtctt cttacaygtc caagaaaaga aaa                                   33

<210> SEQ ID NO 349
<211> LENGTH: 33
<212> TYPE: DNA
<213> ORGANISM: Homo Sapiens

<400> SEQUENCE: 349
gtttaggaag ctgcctraaa ggtgacattc aat                                   33

<210> SEQ ID NO 350
<211> LENGTH: 33
<212> TYPE: DNA
<213> ORGANISM: Homo Sapiens

<400> SEQUENCE: 350
tctggttctt ctaagcrcag atattgtgat tat                                   33

<210> SEQ ID NO 351
<211> LENGTH: 33
<212> TYPE: DNA
<213> ORGANISM: Homo Sapiens

<400> SEQUENCE: 351
atctgatgat acaaacrgag aattgtagta caa                                   33

<210> SEQ ID NO 352
<211> LENGTH: 33
<212> TYPE: DNA
<213> ORGANISM: Homo Sapiens

<400> SEQUENCE: 352
acagcactgt tctcaaragt aaagacatgg act                                   33

<210> SEQ ID NO 353
<211> LENGTH: 33
<212> TYPE: DNA
<213> ORGANISM: Homo Sapiens

<400> SEQUENCE: 353
caaacactaa cctatamcca atctgcctgt ttc                                   33

<210> SEQ ID NO 354
<211> LENGTH: 33
<212> TYPE: DNA
<213> ORGANISM: Homo Sapiens

<400> SEQUENCE: 354
acctggagtg gactackgcc tcacagatca gaa                                   33
```

<210> SEQ ID NO 355
<211> LENGTH: 33
<212> TYPE: DNA
<213> ORGANISM: Homo Sapiens

<400> SEQUENCE: 355
accaaagata tgaagcmgct gtcaaattct gta                             33

<210> SEQ ID NO 356
<211> LENGTH: 33
<212> TYPE: DNA
<213> ORGANISM: Homo Sapiens

<400> SEQUENCE: 356
tctagcacag tagtttwaaa cgttttctca tca                             33

<210> SEQ ID NO 357
<211> LENGTH: 33
<212> TYPE: DNA
<213> ORGANISM: Homo Sapiens

<400> SEQUENCE: 357
aaaaccatga ggttaamgct tagaatgaaa tat                             33

<210> SEQ ID NO 358
<211> LENGTH: 33
<212> TYPE: DNA
<213> ORGANISM: Homo Sapiens

<400> SEQUENCE: 358
tagcccaggg aaagtcycag tttactcctg tca                             33

<210> SEQ ID NO 359
<211> LENGTH: 33
<212> TYPE: DNA
<213> ORGANISM: Homo Sapiens

<400> SEQUENCE: 359
taagcagcac taaagcyacc aaagcaacat gtt                             33

<210> SEQ ID NO 360
<211> LENGTH: 33
<212> TYPE: DNA
<213> ORGANISM: Homo Sapiens

<400> SEQUENCE: 360
ccttggactt gaggtcrcct tgaaataatg agt                             33

<210> SEQ ID NO 361
<211> LENGTH: 33
<212> TYPE: DNA
<213> ORGANISM: Homo Sapiens

<400> SEQUENCE: 361
accaagccaa gtagaargtt gtagtgctgt gtt                             33

<210> SEQ ID NO 362
<211> LENGTH: 33
<212> TYPE: DNA
<213> ORGANISM: Homo Sapiens

<400> SEQUENCE: 362
catctgattt cccaaaygga cactcctagc aga                             33

<210> SEQ ID NO 363
<211> LENGTH: 33
<212> TYPE: DNA
<213> ORGANISM: Homo Sapiens

<400> SEQUENCE: 363
tgatctgtga agaataygga agcatcttgg aag                33

<210> SEQ ID NO 364
<211> LENGTH: 33
<212> TYPE: DNA
<213> ORGANISM: Homo Sapiens

<400> SEQUENCE: 364
tgaaggaagg tttcatkaaa taaatggccc ttg                33

<210> SEQ ID NO 365
<211> LENGTH: 33
<212> TYPE: DNA
<213> ORGANISM: Homo Sapiens

<400> SEQUENCE: 365
tacattttga aaaaacmgac cttgagttat tgc                33

<210> SEQ ID NO 366
<211> LENGTH: 33
<212> TYPE: DNA
<213> ORGANISM: Homo Sapiens

<400> SEQUENCE: 366 gactttccc ttgaaaygta gtgctggcat tta                 33

<210> SEQ ID NO 367
<211> LENGTH: 33
<212> TYPE: DNA
<213> ORGANISM: Homo Sapiens

<400> SEQUENCE: 367
taaaacaaag ctggaaraca gggaggcaat tgc                33

<210> SEQ ID NO 368
<211> LENGTH: 33
<212> TYPE: DNA
<213> ORGANISM: Homo Sapiens

<400> SEQUENCE: 368
tacagtgaat tgaaccrctt cccaaacaat gaa                33

<210> SEQ ID NO 369
<211> LENGTH: 33
<212> TYPE: DNA
<213> ORGANISM: Homo Sapiens

<400> SEQUENCE: 369
tgttgcagct gtccaayctc tctggcattc tag                33

<210> SEQ ID NO 370
<211> LENGTH: 33
<212> TYPE: DNA
<213> ORGANISM: Homo Sapiens

<400> SEQUENCE: 370

```
gacataggag ccttcawaag gaaacgaaga ccc                                    33

<210> SEQ ID NO 371
<211> LENGTH: 33
<212> TYPE: DNA
<213> ORGANISM: Homo Sapiens

<400> SEQUENCE: 371
catcaggttt gcctctraat tactaagact gtg                                    33

<210> SEQ ID NO 372
<211> LENGTH: 33
<212> TYPE: DNA
<213> ORGANISM: Homo Sapiens

<400> SEQUENCE: 372
catcttttca gcaaagycaa aatccttatc ata                                    33

<210> SEQ ID NO 373
<211> LENGTH: 33
<212> TYPE: DNA
<213> ORGANISM: Homo Sapiens

<400> SEQUENCE: 373
aataatgcaa gactcamtca gtggggaaaa tta                                    33

<210> SEQ ID NO 374
<211> LENGTH: 33
<212> TYPE: DNA
<213> ORGANISM: Homo Sapiens

<400> SEQUENCE: 374
cctcctttga cttggamaag agctcaggtt gaa                                    33

<210> SEQ ID NO 375
<211> LENGTH: 33
<212> TYPE: DNA
<213> ORGANISM: Homo Sapiens

<400> SEQUENCE: 375
tccatggaat ctcataycca gactgaagta ata                                    33

<210> SEQ ID NO 376
<211> LENGTH: 33
<212> TYPE: DNA
<213> ORGANISM: Homo Sapiens

<400> SEQUENCE: 376
caatgagtga ctctgaraga gaaaaatgga ctt                                    33

<210> SEQ ID NO 377
<211> LENGTH: 33
<212> TYPE: DNA
<213> ORGANISM: Homo Sapiens

<400> SEQUENCE: 377
cttttagatt gacaggraaa ggtcagcagt gcc                                    33

<210> SEQ ID NO 378
<211> LENGTH: 33
<212> TYPE: DNA
<213> ORGANISM: Homo Sapiens

<400> SEQUENCE: 378
```
taaggaatag ctcttasaaa agttgactag tcc                                    33

<210> SEQ ID NO 379
<211> LENGTH: 33
<212> TYPE: DNA
<213> ORGANISM: Homo Sapiens

<400> SEQUENCE: 379
aaatagttaa ttagaamaag aaccaagcgt gga                                    33

<210> SEQ ID NO 380
<211> LENGTH: 33
<212> TYPE: DNA
<213> ORGANISM: Homo Sapiens

<400> SEQUENCE: 380
ataactttat cgaaaaygaa caatgcatac tgt                                    33

<210> SEQ ID NO 381
<211> LENGTH: 33
<212> TYPE: DNA
<213> ORGANISM: Homo Sapiens

<400> SEQUENCE: 381
tagattgaag gaaagayggg gcagaatctt ggc                                    33

<210> SEQ ID NO 382
<211> LENGTH: 33
<212> TYPE: DNA
<213> ORGANISM: Homo Sapiens

<400> SEQUENCE: 382
tgagaatagg cactccwatt ttcaagctca aat                                    33

<210> SEQ ID NO 383
<211> LENGTH: 33
<212> TYPE: DNA
<213> ORGANISM: Homo Sapiens

<400> SEQUENCE: 383
attcacattc gagggwccc agaaatatgt gaa                                     33

<210> SEQ ID NO 384
<211> LENGTH: 33
<212> TYPE: DNA
<213> ORGANISM: Homo Sapiens

<400> SEQUENCE: 384
ggcatattaa tgacagrctg gaagactctt tag                                    33

<210> SEQ ID NO 385
<211> LENGTH: 33
<212> TYPE: DNA
<213> ORGANISM: Homo Sapiens

<400> SEQUENCE: 385
cactgctatg gtgaaargtc atctgagacc cat                                    33

<210> SEQ ID NO 386
<211> LENGTH: 33
<212> TYPE: DNA
<213> ORGANISM: Homo Sapiens

<400> SEQUENCE: 386
gtccgggcag attggaygca cagactgtcc aga              33

<210> SEQ ID NO 387
<211> LENGTH: 33
<212> TYPE: DNA
<213> ORGANISM: Homo Sapiens

<400> SEQUENCE: 387
gaacatagaa tgattarcag aaaagctttg aac              33

<210> SEQ ID NO 388
<211> LENGTH: 33
<212> TYPE: DNA
<213> ORGANISM: Homo Sapiens

<400> SEQUENCE: 388
attgtgttca gttgttyaaa tgttcaggcc cgt              33

<210> SEQ ID NO 389
<211> LENGTH: 33
<212> TYPE: DNA
<213> ORGANISM: Homo Sapiens

<400> SEQUENCE: 389
ttacttcctt ctaggascaa gctgtgattt cag              33

<210> SEQ ID NO 390
<211> LENGTH: 33
<212> TYPE: DNA
<213> ORGANISM: Homo Sapiens

<400> SEQUENCE: 390
gtttttgcta atgtcargct tggagaatga tta              33

<210> SEQ ID NO 391
<211> LENGTH: 33
<212> TYPE: DNA
<213> ORGANISM: Homo Sapiens

<400> SEQUENCE: 391
aattcagggc agagtcycag aagcattttg ctg              33

<210> SEQ ID NO 392
<211> LENGTH: 33
<212> TYPE: DNA
<213> ORGANISM: Homo Sapiens

<400> SEQUENCE: 392
aatctaaaat gccatgratt ataagacaac cca              33

<210> SEQ ID NO 393
<211> LENGTH: 33
<212> TYPE: DNA
<213> ORGANISM: Homo Sapiens

<400> SEQUENCE: 393
caagtgcaag acgcagsctg ccaaaaggcc att              33

<210> SEQ ID NO 394
<211> LENGTH: 33
<212> TYPE: DNA
<213> ORGANISM: Homo Sapiens

```
<400> SEQUENCE: 394 gccttttgt ttaagcycac gttatattaa tat                                    33

<210> SEQ ID NO 395
<211> LENGTH: 33
<212> TYPE: DNA
<213> ORGANISM: Homo Sapiens

<400> SEQUENCE: 395
ttcccgcaca acattcyact gtgatcaccc cat                                    33

<210> SEQ ID NO 396
<211> LENGTH: 33
<212> TYPE: DNA
<213> ORGANISM: Homo Sapiens

<400> SEQUENCE: 396
cagcatttga tgataawggt tagcataaat ctg                                    33

<210> SEQ ID NO 397
<211> LENGTH: 33
<212> TYPE: DNA
<213> ORGANISM: Homo Sapiens

<400> SEQUENCE: 397
ggcctaaata tgtgtcsaga ctcatccaat ctt                                    33

<210> SEQ ID NO 398
<211> LENGTH: 33
<212> TYPE: DNA
<213> ORGANISM: Homo Sapiens

<400> SEQUENCE: 398
cccctgctgt tgccacygga aaaacatagc ata                                    33

<210> SEQ ID NO 399
<211> LENGTH: 33
<212> TYPE: DNA
<213> ORGANISM: Homo Sapiens

<400> SEQUENCE: 399
aatggccatt atataayagt taccgcatgt gag                                    33

<210> SEQ ID NO 400
<211> LENGTH: 33
<212> TYPE: DNA
<213> ORGANISM: Homo Sapiens

<400> SEQUENCE: 400
tgtaagaaac cacgaawgaa caattctagc tat                                    33

<210> SEQ ID NO 401
<211> LENGTH: 33
<212> TYPE: DNA
<213> ORGANISM: Homo Sapiens

<400> SEQUENCE: 401
gagtataggt tattcaytga aaaaattatg tgc                                    33

<210> SEQ ID NO 402
<211> LENGTH: 33
<212> TYPE: DNA
```

<213> ORGANISM: Homo Sapiens

<400> SEQUENCE: 402
caagcttttc cttcaaygaa cctttgtagg cat         33

<210> SEQ ID NO 403
<211> LENGTH: 33
<212> TYPE: DNA
<213> ORGANISM: Homo Sapiens

<400> SEQUENCE: 403
tgagaacaga ggaaacratt atgaacttga tca         33

<210> SEQ ID NO 404
<211> LENGTH: 33
<212> TYPE: DNA
<213> ORGANISM: Homo Sapiens

<400> SEQUENCE: 404
aagcagtcag aggccakgaa acagggcaaa agc         33

<210> SEQ ID NO 405
<211> LENGTH: 33
<212> TYPE: DNA
<213> ORGANISM: Homo Sapiens

<400> SEQUENCE: 405
cagggagttt aaaccawctt tgagcctctc tct         33

<210> SEQ ID NO 406
<211> LENGTH: 33
<212> TYPE: DNA
<213> ORGANISM: Homo Sapiens

<400> SEQUENCE: 406
agaaaggtac acgccayaaa tgccgacatt caa         33

<210> SEQ ID NO 407
<211> LENGTH: 33
<212> TYPE: DNA
<213> ORGANISM: Homo Sapiens

<400> SEQUENCE: 407
accccagcta tggtgayaga gaagttgaag aga         33

<210> SEQ ID NO 408
<211> LENGTH: 33
<212> TYPE: DNA
<213> ORGANISM: Homo Sapiens

<400> SEQUENCE: 408
ctgcataggt cactgaygct gaatggagtt tgt         33

<210> SEQ ID NO 409
<211> LENGTH: 33
<212> TYPE: DNA
<213> ORGANISM: Homo Sapiens

<400> SEQUENCE: 409
gatgcttaat gaagaartga caatagcctg tga         33

<210> SEQ ID NO 410
<211> LENGTH: 33

<212> TYPE: DNA
<213> ORGANISM: Homo Sapiens

<400> SEQUENCE: 410
tcaatcagga gaaccayatc tttgagaagg cag       33

<210> SEQ ID NO 411
<211> LENGTH: 33
<212> TYPE: DNA
<213> ORGANISM: Homo Sapiens

<400> SEQUENCE: 411
atgaaatccc ccccaaygct ggaatctgac agg       33

<210> SEQ ID NO 412
<211> LENGTH: 33
<212> TYPE: DNA
<213> ORGANISM: Homo Sapiens

<400> SEQUENCE: 412
agaggtagat gaaagayagg aataacatct tca       33

<210> SEQ ID NO 413
<211> LENGTH: 33
<212> TYPE: DNA
<213> ORGANISM: Homo Sapiens

<400> SEQUENCE: 413
gcagtcactg gtgatarctc ataattgtga ttt       33

<210> SEQ ID NO 414
<211> LENGTH: 33
<212> TYPE: DNA
<213> ORGANISM: Homo Sapiens

<400> SEQUENCE: 414
caaaacaagg cccatargta tatatcatat ttc       33

<210> SEQ ID NO 415
<211> LENGTH: 33
<212> TYPE: DNA
<213> ORGANISM: Homo Sapiens

<400> SEQUENCE: 415
caggttacat atccacygat gggttaatgc ata       33

<210> SEQ ID NO 416
<211> LENGTH: 33
<212> TYPE: DNA
<213> ORGANISM: Homo Sapiens

<400> SEQUENCE: 416
tcctttgacc aaggagyaac aaaaagggag tgg       33

<210> SEQ ID NO 417
<211> LENGTH: 33
<212> TYPE: DNA
<213> ORGANISM: Homo Sapiens

<400> SEQUENCE: 417
atcgagtgta ggaaaaygaa agacaggtgc agg       33

<210> SEQ ID NO 418

```
<211> LENGTH: 33
<212> TYPE: DNA
<213> ORGANISM: Homo Sapiens

<400> SEQUENCE: 418
acaccaagga agttcargca tctgggttga ttt                                    33

<210> SEQ ID NO 419
<211> LENGTH: 33
<212> TYPE: DNA
<213> ORGANISM: Homo Sapiens

<400> SEQUENCE: 419
agcagtgctt gctgaargtg tgtggagcag caa                                    33

<210> SEQ ID NO 420
<211> LENGTH: 33
<212> TYPE: DNA
<213> ORGANISM: Homo Sapiens

<400> SEQUENCE: 420
ggataatcct cacccartga atgaggaatc gtt                                    33

<210> SEQ ID NO 421
<211> LENGTH: 33
<212> TYPE: DNA
<213> ORGANISM: Homo Sapiens

<400> SEQUENCE: 421
tttataacta gtttgaytat tgggtgcttc gtt                                    33

<210> SEQ ID NO 422
<211> LENGTH: 33
<212> TYPE: DNA
<213> ORGANISM: Homo Sapiens

<400> SEQUENCE: 422
ggagtaagac tgagagrcca gaaaatctag tta                                    33

<210> SEQ ID NO 423
<211> LENGTH: 33
<212> TYPE: DNA
<213> ORGANISM: Homo Sapiens

<400> SEQUENCE: 423
gctcagaaag gttggaygcc ttgtttagag ctg                                    33

<210> SEQ ID NO 424
<211> LENGTH: 33
<212> TYPE: DNA
<213> ORGANISM: Homo Sapiens

<400> SEQUENCE: 424
cctcccaaag tgctggwaat ccgggaatga acc                                    33

<210> SEQ ID NO 425
<211> LENGTH: 33
<212> TYPE: DNA
<213> ORGANISM: Homo Sapiens

<400> SEQUENCE: 425
ccaagagagg tcagaakaat tcaatctgat gtg                                    33
```

```
<210> SEQ ID NO 426
<211> LENGTH: 33
<212> TYPE: DNA
<213> ORGANISM: Homo Sapiens

<400> SEQUENCE: 426
ttgtataaag ccaaaasaat ttggtaacac ccc                           33

<210> SEQ ID NO 427
<211> LENGTH: 33
<212> TYPE: DNA
<213> ORGANISM: Homo Sapiens

<400> SEQUENCE: 427
gggtgacaga gcataartct ggagtgtggg cag                           33

<210> SEQ ID NO 428
<211> LENGTH: 33
<212> TYPE: DNA
<213> ORGANISM: Homo Sapiens

<400> SEQUENCE: 428
gccttatact ttcacartga tggctaaaac tgg                           33

<210> SEQ ID NO 429
<211> LENGTH: 33
<212> TYPE: DNA
<213> ORGANISM: Homo Sapiens

<400> SEQUENCE: 429
ttctttcaat caacaaktat ttatgaatta cct                           33

<210> SEQ ID NO 430
<211> LENGTH: 33
<212> TYPE: DNA
<213> ORGANISM: Homo Sapiens

<400> SEQUENCE: 430
ccatgctacc taattaycaa aatctttatt gag                           33

<210> SEQ ID NO 431
<211> LENGTH: 33
<212> TYPE: DNA
<213> ORGANISM: Homo Sapiens

<400> SEQUENCE: 431
attcctagcc tctgtawctg tgagaaataa att                           33

<210> SEQ ID NO 432
<211> LENGTH: 33
<212> TYPE: DNA
<213> ORGANISM: Homo Sapiens

<400> SEQUENCE: 432
cttagtcttc taaacartcc cataaggtag ata                           33

<210> SEQ ID NO 433
<211> LENGTH: 33
<212> TYPE: DNA
<213> ORGANISM: Homo Sapiens

<400> SEQUENCE: 433
atggcttgcc caatatmata gagctgccaa gta                           33
```

<210> SEQ ID NO 434
<211> LENGTH: 33
<212> TYPE: DNA
<213> ORGANISM: Homo Sapiens

<400> SEQUENCE: 434
catctttatt gcctcamgga cagaattgga gat                               33

<210> SEQ ID NO 435
<211> LENGTH: 33
<212> TYPE: DNA
<213> ORGANISM: Homo Sapiens

<400> SEQUENCE: 435
cagaagtata agtagawcga tgatgtatta ggc                               33

<210> SEQ ID NO 436
<211> LENGTH: 33
<212> TYPE: DNA
<213> ORGANISM: Homo Sapiens

<400> SEQUENCE: 436
agtttcaaag tctggayagc tgtagaacta ttt                               33

<210> SEQ ID NO 437
<211> LENGTH: 33
<212> TYPE: DNA
<213> ORGANISM: Homo Sapiens

<400> SEQUENCE: 437
ttgcctattg ctaatakagt aaaagccaca ata                               33

<210> SEQ ID NO 438
<211> LENGTH: 33
<212> TYPE: DNA
<213> ORGANISM: Homo Sapiens

<400> SEQUENCE: 438
gcttgtattt aagtaaytga tccagagcag gct                               33

<210> SEQ ID NO 439
<211> LENGTH: 33
<212> TYPE: DNA
<213> ORGANISM: Homo Sapiens

<400> SEQUENCE: 439
ttttaacaca ggtggartat cagaaaaatg tag                               33

<210> SEQ ID NO 440
<211> LENGTH: 33
<212> TYPE: DNA
<213> ORGANISM: Homo Sapiens

<400> SEQUENCE: 440
ttcccccatt tgccaawtca gttctctcca gtt                               33

<210> SEQ ID NO 441
<211> LENGTH: 33
<212> TYPE: DNA
<213> ORGANISM: Homo Sapiens

<400> SEQUENCE: 441
taagtgtgat tactagrcgg ctttaatgat taa                               33

<210> SEQ ID NO 442
<211> LENGTH: 33
<212> TYPE: DNA
<213> ORGANISM: Homo Sapiens

<400> SEQUENCE: 442
ggctctctgt ggggaaygca ccaagtgcct gga                                    33

<210> SEQ ID NO 443
<211> LENGTH: 33
<212> TYPE: DNA
<213> ORGANISM: Homo Sapiens

<400> SEQUENCE: 443
atgcatacta cataaaygtg acagtttaac aag                                    33

<210> SEQ ID NO 444
<211> LENGTH: 33
<212> TYPE: DNA
<213> ORGANISM: Homo Sapiens

<400> SEQUENCE: 444
tggcatttaa gctgaaygat ggagtcaaca gag                                    33

<210> SEQ ID NO 445
<211> LENGTH: 33
<212> TYPE: DNA
<213> ORGANISM: Homo Sapiens

<400> SEQUENCE: 445
ggtttctata ctgaatmagt taactgtcac tac                                    33

<210> SEQ ID NO 446
<211> LENGTH: 33
<212> TYPE: DNA
<213> ORGANISM: Homo Sapiens

<400> SEQUENCE: 446
attttcccgg tgtcaaygta gctctccctt gtt                                    33

<210> SEQ ID NO 447
<211> LENGTH: 33
<212> TYPE: DNA
<213> ORGANISM: Homo Sapiens

<400> SEQUENCE: 447
atatcctagg ggccaaygcc attctcaaac ttt                                    33

<210> SEQ ID NO 448
<211> LENGTH: 33
<212> TYPE: DNA
<213> ORGANISM: Homo Sapiens

<400> SEQUENCE: 448
tccattctat ggagcgwcca cattttgctt att                                    33

<210> SEQ ID NO 449
<211> LENGTH: 33
<212> TYPE: DNA
<213> ORGANISM: Homo Sapiens

<400> SEQUENCE: 449
agaaattaga tgcacaragt aaaaaacgtt aag                        33

<210> SEQ ID NO 450
<211> LENGTH: 33
<212> TYPE: DNA
<213> ORGANISM: Homo Sapiens

<400> SEQUENCE: 450
ccaatcattt gaattcyatt cttgaggtaa gtg                        33

<210> SEQ ID NO 451
<211> LENGTH: 33
<212> TYPE: DNA
<213> ORGANISM: Homo Sapiens

<400> SEQUENCE: 451
gtgccgtgga gatacayaga tgattgccat att                        33

<210> SEQ ID NO 452
<211> LENGTH: 33
<212> TYPE: DNA
<213> ORGANISM: Homo Sapiens

<400> SEQUENCE: 452
taactgacag gactagsatt cttgcctgag tca                        33

<210> SEQ ID NO 453
<211> LENGTH: 33
<212> TYPE: DNA
<213> ORGANISM: Homo Sapiens

<400> SEQUENCE: 453
aacagtgata ctcaggyact acatcagggt ctt                        33

<210> SEQ ID NO 454
<211> LENGTH: 33
<212> TYPE: DNA
<213> ORGANISM: Homo Sapiens

<400> SEQUENCE: 454
gtggacagga gggaaasagt gaaaccaggt ctc                        33

<210> SEQ ID NO 455
<211> LENGTH: 33
<212> TYPE: DNA
<213> ORGANISM: Homo Sapiens

<400> SEQUENCE: 455
tcttgctctg ggctccrcaa tgtcaggggt ggc                        33

<210> SEQ ID NO 456
<211> LENGTH: 33
<212> TYPE: DNA
<213> ORGANISM: Homo Sapiens

<400> SEQUENCE: 456
ttatggtgtt gccggarctc atggagcaga gaa                        33

<210> SEQ ID NO 457
<211> LENGTH: 33
<212> TYPE: DNA
<213> ORGANISM: Homo Sapiens

<400> SEQUENCE: 457
gcccgtaggg agtatcrctt gacggagagt gag					33

<210> SEQ ID NO 458
<211> LENGTH: 33
<212> TYPE: DNA
<213> ORGANISM: Homo Sapiens

<400> SEQUENCE: 458
gacagatggc cgtggcrccc tcagattcag ccc					33

<210> SEQ ID NO 459
<211> LENGTH: 33
<212> TYPE: DNA
<213> ORGANISM: Homo Sapiens

<400> SEQUENCE: 459
tgtgagggcc aaacackgta actgaaacac aga					33

<210> SEQ ID NO 460
<211> LENGTH: 33
<212> TYPE: DNA
<213> ORGANISM: Homo Sapiens

<400> SEQUENCE: 460
cttcccagca ttgatgrcag ccaattacgg aaa					33

<210> SEQ ID NO 461
<211> LENGTH: 33
<212> TYPE: DNA
<213> ORGANISM: Homo Sapiens

<400> SEQUENCE: 461
cacaggcgtc cacaccrgat tcttcattgc tgc					33

<210> SEQ ID NO 462
<211> LENGTH: 33
<212> TYPE: DNA
<213> ORGANISM: Homo Sapiens

<400> SEQUENCE: 462
tgagcctttg ccagcaytga gtattaagtt tta					33

<210> SEQ ID NO 463
<211> LENGTH: 33
<212> TYPE: DNA
<213> ORGANISM: Homo Sapiens

<400> SEQUENCE: 463
tgccatgtac tcactgwgat tttgggcagg tca					33

<210> SEQ ID NO 464
<211> LENGTH: 33
<212> TYPE: DNA
<213> ORGANISM: Homo Sapiens

<400> SEQUENCE: 464
tgttggaact cctcaawctg ccattctgta cat					33

<210> SEQ ID NO 465
<211> LENGTH: 33
<212> TYPE: DNA
<213> ORGANISM: Homo Sapiens

<400> SEQUENCE: 465
ttttgccagc ataaaasggg aaaaaaatac cac        33

<210> SEQ ID NO 466
<211> LENGTH: 33
<212> TYPE: DNA
<213> ORGANISM: Homo Sapiens

<400> SEQUENCE: 466
cttgtgctaa accccaygag aggtgttgta tgc        33

<210> SEQ ID NO 467
<211> LENGTH: 33
<212> TYPE: DNA
<213> ORGANISM: Homo Sapiens

<400> SEQUENCE: 467
tgtccaaatc tgtgaarctc tgcacactgc att        33

<210> SEQ ID NO 468
<211> LENGTH: 33
<212> TYPE: DNA
<213> ORGANISM: Homo Sapiens

<400> SEQUENCE: 468
atctattata aggaaakatg agtcagagta ggc        33

<210> SEQ ID NO 469
<211> LENGTH: 33
<212> TYPE: DNA
<213> ORGANISM: Homo Sapiens

<400> SEQUENCE: 469
agtcaattaa gcccacyggc aggaatgcat ttc        33

<210> SEQ ID NO 470
<211> LENGTH: 33
<212> TYPE: DNA
<213> ORGANISM: Homo Sapiens

<400> SEQUENCE: 470
gcaggccacg tcaaaartgt gtctgctaca taa        33

<210> SEQ ID NO 471
<211> LENGTH: 33
<212> TYPE: DNA
<213> ORGANISM: Homo Sapiens

<400> SEQUENCE: 471
agagcattct gtttgtraaa cctaacctgg gga        33

<210> SEQ ID NO 472
<211> LENGTH: 33
<212> TYPE: DNA
<213> ORGANISM: Homo Sapiens

<400> SEQUENCE: 472
aaaattgtga agacccmcta agttacccac cca        33

<210> SEQ ID NO 473
<211> LENGTH: 33
<212> TYPE: DNA
<213> ORGANISM: Homo Sapiens

<400> SEQUENCE: 473
ttattttgtc tcaccartcc tactttcctc gtc                              33

<210> SEQ ID NO 474
<211> LENGTH: 33
<212> TYPE: DNA
<213> ORGANISM: Homo Sapiens

<400> SEQUENCE: 474
agaaaagtta caatgcwagg cagtatttaa gaa                              33

<210> SEQ ID NO 475
<211> LENGTH: 33
<212> TYPE: DNA
<213> ORGANISM: Homo Sapiens

<400> SEQUENCE: 475 gcaaaaggt gaaaacragg gcaagactat gta                               33

<210> SEQ ID NO 476
<211> LENGTH: 33
<212> TYPE: DNA
<213> ORGANISM: Homo Sapiens

<400> SEQUENCE: 476
ttcagtgttc ttgttgwaat ttagcaatca aaa                              33

<210> SEQ ID NO 477
<211> LENGTH: 33
<212> TYPE: DNA
<213> ORGANISM: Homo Sapiens

<400> SEQUENCE: 477
cattacaata ttacccmgac gattacccaa gac                              33

<210> SEQ ID NO 478
<211> LENGTH: 33
<212> TYPE: DNA
<213> ORGANISM: Homo Sapiens

<400> SEQUENCE: 478
ccagcccaag agagaaygtg gattttatgc tca                              33

<210> SEQ ID NO 479
<211> LENGTH: 33
<212> TYPE: DNA
<213> ORGANISM: Homo Sapiens

<400> SEQUENCE: 479
aatctgatct tggatamctg agctgattgt gac                              33

<210> SEQ ID NO 480
<211> LENGTH: 33
<212> TYPE: DNA
<213> ORGANISM: Homo Sapiens

<400> SEQUENCE: 480
tccctgctgt gaacacratt tctacaatcc tag                              33

<210> SEQ ID NO 481
<211> LENGTH: 33
<212> TYPE: DNA

<213> ORGANISM: Homo Sapiens

<400> SEQUENCE: 481
tgtttatgat gacagtyact gaacaaaatt tcc 33

<210> SEQ ID NO 482
<211> LENGTH: 33
<212> TYPE: DNA
<213> ORGANISM: Homo Sapiens

<400> SEQUENCE: 482
tcaagtttaa tataccyaag ttgtggagaa ata 33

<210> SEQ ID NO 483
<211> LENGTH: 33
<212> TYPE: DNA
<213> ORGANISM: Homo Sapiens

<400> SEQUENCE: 483
tatatatcat agcaggwact ggacgttttt tga 33

<210> SEQ ID NO 484
<211> LENGTH: 33
<212> TYPE: DNA
<213> ORGANISM: Homo Sapiens

<400> SEQUENCE: 484
ataaatcaaa ccagaayagc tataaagata agc 33

<210> SEQ ID NO 485
<211> LENGTH: 33
<212> TYPE: DNA
<213> ORGANISM: Homo Sapiens

<400> SEQUENCE: 485
ttatagatca gaaaacmagt ctagagaggt taa 33

<210> SEQ ID NO 486
<211> LENGTH: 33
<212> TYPE: DNA
<213> ORGANISM: Homo Sapiens

<400> SEQUENCE: 486 atcactttg gaatgargtc agtataaatc att 33

<210> SEQ ID NO 487
<211> LENGTH: 33
<212> TYPE: DNA
<213> ORGANISM: Homo Sapiens

<400> SEQUENCE: 487
tggtgcctca cgcccaygaa agaaggctgc cac 33

<210> SEQ ID NO 488
<211> LENGTH: 33
<212> TYPE: DNA
<213> ORGANISM: Homo Sapiens

<400> SEQUENCE: 488
ttcaaactga aatgtasagc tttgttttga aaa 33

<210> SEQ ID NO 489
<211> LENGTH: 33

<212> TYPE: DNA
<213> ORGANISM: Homo Sapiens

<400> SEQUENCE: 489
agctggaagt attcacrgaa cataggagga aac    33

<210> SEQ ID NO 490
<211> LENGTH: 33
<212> TYPE: DNA
<213> ORGANISM: Homo Sapiens

<400> SEQUENCE: 490
atgggaggag gaaatcraag gtttagaaaa gga    33

<210> SEQ ID NO 491
<211> LENGTH: 33
<212> TYPE: DNA
<213> ORGANISM: Homo Sapiens

<400> SEQUENCE: 491
tccccatgcc aagcttyaaa ggaaaatact ctc    33

<210> SEQ ID NO 492
<211> LENGTH: 33
<212> TYPE: DNA
<213> ORGANISM: Homo Sapiens

<400> SEQUENCE: 492
agtagaggca agccagycag tctatgcaga tat    33

<210> SEQ ID NO 493
<211> LENGTH: 33
<212> TYPE: DNA
<213> ORGANISM: Homo Sapiens

<400> SEQUENCE: 493
acccccttat atgctcrcta cagattccaa aac    33

<210> SEQ ID NO 494
<211> LENGTH: 33
<212> TYPE: DNA
<213> ORGANISM: Homo Sapiens

<400> SEQUENCE: 494
atttggctta agttgcratt ctgtcacttg caa    33

<210> SEQ ID NO 495
<211> LENGTH: 33
<212> TYPE: DNA
<213> ORGANISM: Homo Sapiens

<400> SEQUENCE: 495
cgtttcagga aaataaytgg caacatgcac caa    33

<210> SEQ ID NO 496
<211> LENGTH: 33
<212> TYPE: DNA
<213> ORGANISM: Homo Sapiens

<400> SEQUENCE: 496
cgttcctaga agagacrgag agcgctgact gaa    33

<210> SEQ ID NO 497

```
<211> LENGTH: 33
<212> TYPE: DNA
<213> ORGANISM: Homo Sapiens

<400> SEQUENCE: 497
ggaagaggcc tccaccratt tgttttcagt gcc                                33

<210> SEQ ID NO 498
<211> LENGTH: 33
<212> TYPE: DNA
<213> ORGANISM: Homo Sapiens

<400> SEQUENCE: 498
attgtttctc tgctgascac attaggacta cat                                33

<210> SEQ ID NO 499
<211> LENGTH: 33
<212> TYPE: DNA
<213> ORGANISM: Homo Sapiens

<400> SEQUENCE: 499
cctgtattcc agttcaytca ttctaatatt ctc                                33

<210> SEQ ID NO 500
<211> LENGTH: 33
<212> TYPE: DNA
<213> ORGANISM: Homo Sapiens

<400> SEQUENCE: 500
acgggaaact tggccaygca aagatgaaac atg                                33

<210> SEQ ID NO 501
<211> LENGTH: 33
<212> TYPE: DNA
<213> ORGANISM: Homo Sapiens

<400> SEQUENCE: 501
atactgtgca atgaccyatt ggcagaacgg tta                                33

<210> SEQ ID NO 502
<211> LENGTH: 33
<212> TYPE: DNA
<213> ORGANISM: Homo Sapiens

<400> SEQUENCE: 502
aatcctctct aaatggsact caggatagca cca                                33

<210> SEQ ID NO 503
<211> LENGTH: 33
<212> TYPE: DNA
<213> ORGANISM: Homo Sapiens

<400> SEQUENCE: 503
agcaggcaca atgtacygat accaattttc tgg                                33

<210> SEQ ID NO 504
<211> LENGTH: 33
<212> TYPE: DNA
<213> ORGANISM: Homo Sapiens

<400> SEQUENCE: 504
cttcatgttc tcttctwaac agggtgagtt gct                                33
```

```
<210> SEQ ID NO 505
<211> LENGTH: 33
<212> TYPE: DNA
<213> ORGANISM: Homo Sapiens

<400> SEQUENCE: 505
caagaggact gatgaargag aagccagccg ttg                                  33

<210> SEQ ID NO 506
<211> LENGTH: 33
<212> TYPE: DNA
<213> ORGANISM: Homo Sapiens

<400> SEQUENCE: 506
aacaaatgta aggtgamaac aaaaagcagt aat                                  33

<210> SEQ ID NO 507
<211> LENGTH: 33
<212> TYPE: DNA
<213> ORGANISM: Homo Sapiens

<400> SEQUENCE: 507
ctttcagagt cctacarcat acaagcttct cgt                                  33

<210> SEQ ID NO 508
<211> LENGTH: 33
<212> TYPE: DNA
<213> ORGANISM: Homo Sapiens

<400> SEQUENCE: 508
atcaccaaca taaaaayatg cgactaagaa caa                                  33

<210> SEQ ID NO 509
<211> LENGTH: 33
<212> TYPE: DNA
<213> ORGANISM: Homo Sapiens

<400> SEQUENCE: 509
cacagtattc ataaaaygtt tgcattatgt aga                                  33

<210> SEQ ID NO 510
<211> LENGTH: 33
<212> TYPE: DNA
<213> ORGANISM: Homo Sapiens

<400> SEQUENCE: 510
tttggcagca gcacgaygta gtctacccgc cac                                  33

<210> SEQ ID NO 511
<211> LENGTH: 33
<212> TYPE: DNA
<213> ORGANISM: Homo Sapiens

<400> SEQUENCE: 511
caaggcaagc tgtctayggc tgctgctgga agg                                  33

<210> SEQ ID NO 512
<211> LENGTH: 33
<212> TYPE: DNA
<213> ORGANISM: Homo Sapiens

<400> SEQUENCE: 512
ttcggtattg ccacatrata tctgttcatt atc                                  33
```

<210> SEQ ID NO 513
<211> LENGTH: 33
<212> TYPE: DNA
<213> ORGANISM: Homo Sapiens

<400> SEQUENCE: 513
gaaatagtaa acggcaragt aggaaagtga aac                                    33

<210> SEQ ID NO 514
<211> LENGTH: 33
<212> TYPE: DNA
<213> ORGANISM: Homo Sapiens

<400> SEQUENCE: 514
agcatcttca atatgascaa aacttgctca gca                                    33

<210> SEQ ID NO 515
<211> LENGTH: 33
<212> TYPE: DNA
<213> ORGANISM: Homo Sapiens

<400> SEQUENCE: 515
ttacatgtgt gatgagwata tgtaaagcac tcg                                    33

<210> SEQ ID NO 516
<211> LENGTH: 33
<212> TYPE: DNA
<213> ORGANISM: Homo Sapiens

<400> SEQUENCE: 516
ccaacatatg atagaakggg aaaaagcaac aaa                                    33

<210> SEQ ID NO 517
<211> LENGTH: 33
<212> TYPE: DNA
<213> ORGANISM: Homo Sapiens

<400> SEQUENCE: 517
aagtaaaagt accacasaga tctttctaca aca                                    33

<210> SEQ ID NO 518
<211> LENGTH: 33
<212> TYPE: DNA
<213> ORGANISM: Homo Sapiens

<400> SEQUENCE: 518
ttatggagaa tgtctaragt gagtacagta tgt                                    33

<210> SEQ ID NO 519
<211> LENGTH: 33
<212> TYPE: DNA
<213> ORGANISM: Homo Sapiens

<400> SEQUENCE: 519
ctgcttgcag aaaaacrcat acttttgttt ata                                    33

<210> SEQ ID NO 520
<211> LENGTH: 33
<212> TYPE: DNA
<213> ORGANISM: Homo Sapiens

<400> SEQUENCE: 520
tctctcttca gactcaygag gtactctggt gac                                    33

<210> SEQ ID NO 521
<211> LENGTH: 33
<212> TYPE: DNA
<213> ORGANISM: Homo Sapiens

<400> SEQUENCE: 521
tttgtgatag gttttaratt ccaggatgcg tgt                           33

<210> SEQ ID NO 522
<211> LENGTH: 33
<212> TYPE: DNA
<213> ORGANISM: Homo Sapiens

<400> SEQUENCE: 522
atgttttcat tctccamgag tgaattgaat gat                           33

<210> SEQ ID NO 523
<211> LENGTH: 33
<212> TYPE: DNA
<213> ORGANISM: Homo Sapiens

<400> SEQUENCE: 523
tgactgttag tgctaaygca gtacatgtct aga                           33

<210> SEQ ID NO 524
<211> LENGTH: 33
<212> TYPE: DNA
<213> ORGANISM: Homo Sapiens

<400> SEQUENCE: 524
gtcacagacc aaatgaygga taattaagca ttc                           33

<210> SEQ ID NO 525
<211> LENGTH: 33
<212> TYPE: DNA
<213> ORGANISM: Homo Sapiens

<400> SEQUENCE: 525
gttacttaat caaacaygga tctagttgtt ttg                           33

<210> SEQ ID NO 526
<211> LENGTH: 33
<212> TYPE: DNA
<213> ORGANISM: Homo Sapiens

<400> SEQUENCE: 526
actttcatac agaggasatg gtaatcttaa aaa                           33

<210> SEQ ID NO 527
<211> LENGTH: 33
<212> TYPE: DNA
<213> ORGANISM: Homo Sapiens

<400> SEQUENCE: 527
ttcttaacat tgagcaygtt aacggctagc aat                           33

<210> SEQ ID NO 528
<211> LENGTH: 33
<212> TYPE: DNA
<213> ORGANISM: Homo Sapiens

<400> SEQUENCE: 528

```
cagcatgggg tcacgcrgat gcagaaaagc aga                                    33

<210> SEQ ID NO 529
<211> LENGTH: 33
<212> TYPE: DNA
<213> ORGANISM: Homo Sapiens

<400> SEQUENCE: 529
tggagaaaca acactcygag gaagtctcca tag                                    33

<210> SEQ ID NO 530
<211> LENGTH: 33
<212> TYPE: DNA
<213> ORGANISM: Homo Sapiens

<400> SEQUENCE: 530
tgtcacatgt cagagartat cattaaaaga aga                                    33

<210> SEQ ID NO 531
<211> LENGTH: 33
<212> TYPE: DNA
<213> ORGANISM: Homo Sapiens

<400> SEQUENCE: 531
ttgaaaacag ctaaacwagt aagttcttca gtt                                    33

<210> SEQ ID NO 532
<211> LENGTH: 33
<212> TYPE: DNA
<213> ORGANISM: Homo Sapiens

<400> SEQUENCE: 532
gctgccatga gggttgyagc cctgtctcat atg                                    33

<210> SEQ ID NO 533
<211> LENGTH: 33
<212> TYPE: DNA
<213> ORGANISM: Homo Sapiens

<400> SEQUENCE: 533
aagaaggctg atgttakcct gatggggttc act                                    33

<210> SEQ ID NO 534
<211> LENGTH: 33
<212> TYPE: DNA
<213> ORGANISM: Homo Sapiens

<400> SEQUENCE: 534
aaacattgtc taatagmatt ttctgcacta aca                                    33

<210> SEQ ID NO 535
<211> LENGTH: 33
<212> TYPE: DNA
<213> ORGANISM: Homo Sapiens

<400> SEQUENCE: 535
aatggctgaa tgagatraga ttaggaggag tga                                    33

<210> SEQ ID NO 536
<211> LENGTH: 33
<212> TYPE: DNA
<213> ORGANISM: Homo Sapiens

<400> SEQUENCE: 536
```
ggttgcacaa taatgcrcta aaaagttgtt tcc                                    33

<210> SEQ ID NO 537
<211> LENGTH: 33
<212> TYPE: DNA
<213> ORGANISM: Homo Sapiens

<400> SEQUENCE: 537
actctgcata ccctcayagc ctggctgaaa gta                                    33

<210> SEQ ID NO 538
<211> LENGTH: 33
<212> TYPE: DNA
<213> ORGANISM: Homo Sapiens

<400> SEQUENCE: 538
gggagacact gtgtggycat ctttgaaaac aaa                                    33

<210> SEQ ID NO 539
<211> LENGTH: 33
<212> TYPE: DNA
<213> ORGANISM: Homo Sapiens

<400> SEQUENCE: 539
tacagccaac taaggargcg aaaaatctct aca                                    33

<210> SEQ ID NO 540
<211> LENGTH: 33
<212> TYPE: DNA
<213> ORGANISM: Homo Sapiens

<400> SEQUENCE: 540
aagagacaat atacccraat ctcacgccta agg                                    33

<210> SEQ ID NO 541
<211> LENGTH: 33
<212> TYPE: DNA
<213> ORGANISM: Homo Sapiens

<400> SEQUENCE: 541
ctaaaatgtg tacgctragc catagaaatg cac                                    33

<210> SEQ ID NO 542
<211> LENGTH: 33
<212> TYPE: DNA
<213> ORGANISM: Homo Sapiens

<400> SEQUENCE: 542
tcagttcatg gaaatcyatt cagtggtagc ctt                                    33

<210> SEQ ID NO 543
<211> LENGTH: 33
<212> TYPE: DNA
<213> ORGANISM: Homo Sapiens

<400> SEQUENCE: 543
ccacacatag cacaatraag tgaatttcac agg                                    33

<210> SEQ ID NO 544
<211> LENGTH: 33
<212> TYPE: DNA
<213> ORGANISM: Homo Sapiens

```
<400> SEQUENCE: 544
taagacaagt agggtcrcta gaaaatgcag aga                              33

<210> SEQ ID NO 545
<211> LENGTH: 33
<212> TYPE: DNA
<213> ORGANISM: Homo Sapiens

<400> SEQUENCE: 545
tttcccagca acctgargat aaggcacctc tgg                              33

<210> SEQ ID NO 546
<211> LENGTH: 33
<212> TYPE: DNA
<213> ORGANISM: Homo Sapiens

<400> SEQUENCE: 546
tacatgtgac ttagaastgt tttttgtttt tgt                              33

<210> SEQ ID NO 547
<211> LENGTH: 33
<212> TYPE: DNA
<213> ORGANISM: Homo Sapiens

<400> SEQUENCE: 547
gtagattccc ttgacargtt gaggaacttc ctt                              33

<210> SEQ ID NO 548
<211> LENGTH: 33
<212> TYPE: DNA
<213> ORGANISM: Homo Sapiens

<400> SEQUENCE: 548
tcctctatct ctatccyact accaccagtc tgt                              33

<210> SEQ ID NO 549
<211> LENGTH: 33
<212> TYPE: DNA
<213> ORGANISM: Homo Sapiens

<400> SEQUENCE: 549
ttggaaggcc tcacacmggc aactgggccc aac                              33

<210> SEQ ID NO 550
<211> LENGTH: 33
<212> TYPE: DNA
<213> ORGANISM: Homo Sapiens

<400> SEQUENCE: 550
acaatgactc caagaartaa gtgtggtccc att                              33

<210> SEQ ID NO 551
<211> LENGTH: 33
<212> TYPE: DNA
<213> ORGANISM: Homo Sapiens

<400> SEQUENCE: 551
caattcctgg ccccgcwctt gcgtcaatat ggt                              33

<210> SEQ ID NO 552
<211> LENGTH: 33
<212> TYPE: DNA
<213> ORGANISM: Homo Sapiens
```

<400> SEQUENCE: 552
agcaagcaac ccgagcraat cgcagttgga gag                                33

<210> SEQ ID NO 553
<211> LENGTH: 33
<212> TYPE: DNA
<213> ORGANISM: Homo Sapiens

<400> SEQUENCE: 553
tgcttatctg actatayaga agtcaacata gca                                33

<210> SEQ ID NO 554
<211> LENGTH: 33
<212> TYPE: DNA
<213> ORGANISM: Homo Sapiens

<400> SEQUENCE: 554
ttttaggaat gtttcayagt ctgaggcgcc agg                                33

<210> SEQ ID NO 555
<211> LENGTH: 33
<212> TYPE: DNA
<213> ORGANISM: Homo Sapiens

<400> SEQUENCE: 555
aggtgatctc agtatcyccc agtttccctt tgg                                33

<210> SEQ ID NO 556
<211> LENGTH: 33
<212> TYPE: DNA
<213> ORGANISM: Homo Sapiens

<400> SEQUENCE: 556
gtgtgtcacc ttacccsccg tagtcattct cct                                33

<210> SEQ ID NO 557
<211> LENGTH: 33
<212> TYPE: DNA
<213> ORGANISM: Homo Sapiens

<400> SEQUENCE: 557
tggcatcatg gaaaagyacc agcttggttt tgg                                33

<210> SEQ ID NO 558
<211> LENGTH: 33
<212> TYPE: DNA
<213> ORGANISM: Homo Sapiens

<400> SEQUENCE: 558
ttgatcacac aggccakcat ggaaggtgta gca                                33

<210> SEQ ID NO 559
<211> LENGTH: 33
<212> TYPE: DNA
<213> ORGANISM: Homo Sapiens

<400> SEQUENCE: 559
tttggaaata tggtcaygct agatgtaact agt                                33

<210> SEQ ID NO 560
<211> LENGTH: 33
<212> TYPE: DNA

<213> ORGANISM: Homo Sapiens

<400> SEQUENCE: 560
aagctgagaa gggccaygag cctcgtaatc cag                33

<210> SEQ ID NO 561
<211> LENGTH: 33
<212> TYPE: DNA
<213> ORGANISM: Homo Sapiens

<400> SEQUENCE: 561
gaacccagac atactaygca aaaaattcag aac                33

<210> SEQ ID NO 562
<211> LENGTH: 33
<212> TYPE: DNA
<213> ORGANISM: Homo Sapiens

<400> SEQUENCE: 562
caatttgtct gcaaacratg ctccatcagt ctc                33

<210> SEQ ID NO 563
<211> LENGTH: 33
<212> TYPE: DNA
<213> ORGANISM: Homo Sapiens

<400> SEQUENCE: 563
agtggaattt gggagaytca cagttaagga gtg                33

<210> SEQ ID NO 564
<211> LENGTH: 33
<212> TYPE: DNA
<213> ORGANISM: Homo Sapiens

<400> SEQUENCE: 564
ccttttggaa tgctatragt gacataaaca ctc                33

<210> SEQ ID NO 565
<211> LENGTH: 33
<212> TYPE: DNA
<213> ORGANISM: Homo Sapiens

<400> SEQUENCE: 565
gagaagaaat tgatggyata tcagctgggt aca                33

<210> SEQ ID NO 566
<211> LENGTH: 33
<212> TYPE: DNA
<213> ORGANISM: Homo Sapiens

<400> SEQUENCE: 566
aaggaaccat ttcattmaaa taagccaaca ttt                33

<210> SEQ ID NO 567
<211> LENGTH: 33
<212> TYPE: DNA
<213> ORGANISM: Homo Sapiens

<400> SEQUENCE: 567
cacattcaat ctttggyact ccaggatttt gag                33

<210> SEQ ID NO 568
<211> LENGTH: 33

```
<212> TYPE: DNA
<213> ORGANISM: Homo Sapiens

<400> SEQUENCE: 568
gtaaatgtgt gttagtsaat ggagaaaccc ctt                          33

<210> SEQ ID NO 569
<211> LENGTH: 33
<212> TYPE: DNA
<213> ORGANISM: Homo Sapiens

<400> SEQUENCE: 569
agtcccttga tcttaawtgt agccttattg tct                          33

<210> SEQ ID NO 570
<211> LENGTH: 33
<212> TYPE: DNA
<213> ORGANISM: Homo Sapiens

<400> SEQUENCE: 570
caaaccatat cactggrcat tgggaaattt aaa                          33

<210> SEQ ID NO 571
<211> LENGTH: 33
<212> TYPE: DNA
<213> ORGANISM: Homo Sapiens

<400> SEQUENCE: 571
cagaactgtg agacgayaca ttcctgttgc tct                          33

<210> SEQ ID NO 572
<211> LENGTH: 33
<212> TYPE: DNA
<213> ORGANISM: Homo Sapiens

<400> SEQUENCE: 572
ttgcccagca ctatcascaa tctgcaaaaa gat                          33

<210> SEQ ID NO 573
<211> LENGTH: 33
<212> TYPE: DNA
<213> ORGANISM: Homo Sapiens

<400> SEQUENCE: 573
tattgaccca aggtgcyatc agagtcatga ggt                          33

<210> SEQ ID NO 574
<211> LENGTH: 33
<212> TYPE: DNA
<213> ORGANISM: Homo Sapiens

<400> SEQUENCE: 574
ccaggaaagg ctatgcraac agtcaagaac ata                          33

<210> SEQ ID NO 575
<211> LENGTH: 33
<212> TYPE: DNA
<213> ORGANISM: Homo Sapiens

<400> SEQUENCE: 575
tgaatactta aaatayacc attcactttc ata                           33

<210> SEQ ID NO 576
```

```
<211> LENGTH: 33
<212> TYPE: DNA
<213> ORGANISM: Homo Sapiens

<400> SEQUENCE: 576
ctcagactcg aagggaragc aatcagattc caa                                    33

<210> SEQ ID NO 577
<211> LENGTH: 33
<212> TYPE: DNA
<213> ORGANISM: Homo Sapiens

<400> SEQUENCE: 577
aggcagaagt ctgctgyaaa gtcaaagccc tca                                    33

<210> SEQ ID NO 578
<211> LENGTH: 33
<212> TYPE: DNA
<213> ORGANISM: Homo Sapiens

<400> SEQUENCE: 578
aaatgaagaa aatacayagg cttggcaggt tac                                    33

<210> SEQ ID NO 579
<211> LENGTH: 33
<212> TYPE: DNA
<213> ORGANISM: Homo Sapiens

<400> SEQUENCE: 579
agagttcatt ctggacsatg agaataccte agc                                    33

<210> SEQ ID NO 580
<211> LENGTH: 33
<212> TYPE: DNA
<213> ORGANISM: Homo Sapiens

<400> SEQUENCE: 580
agatagggcc aagtacracg caccttgacg gat                                    33

<210> SEQ ID NO 581
<211> LENGTH: 33
<212> TYPE: DNA
<213> ORGANISM: Homo Sapiens

<400> SEQUENCE: 581
tgtgattggt tgctgckccc ttgcaatctt agt                                    33

<210> SEQ ID NO 582
<211> LENGTH: 33
<212> TYPE: DNA
<213> ORGANISM: Homo Sapiens

<400> SEQUENCE: 582
aatccagagg gagaaaytgg taggactgga cgg                                    33

<210> SEQ ID NO 583
<211> LENGTH: 33
<212> TYPE: DNA
<213> ORGANISM: Homo Sapiens

<400> SEQUENCE: 583
aactgcagtg tggacayctc agaacaacac tgt                                    33
```

```
<210> SEQ ID NO 584
<211> LENGTH: 33
<212> TYPE: DNA
<213> ORGANISM: Homo Sapiens

<400> SEQUENCE: 584
gaaaagacac caaaaawgtc cttgattttt ctc                                   33

<210> SEQ ID NO 585
<211> LENGTH: 33
<212> TYPE: DNA
<213> ORGANISM: Homo Sapiens

<400> SEQUENCE: 585
tttctctaat caataarcag caatttaaaa tca                                   33

<210> SEQ ID NO 586
<211> LENGTH: 33
<212> TYPE: DNA
<213> ORGANISM: Homo Sapiens

<400> SEQUENCE: 586
tgccctaatc tatacargag ctaagtatgg act                                   33

<210> SEQ ID NO 587
<211> LENGTH: 33
<212> TYPE: DNA
<213> ORGANISM: Homo Sapiens

<400> SEQUENCE: 587
tccttcttag ctgatgraag agatactgct tga                                   33

<210> SEQ ID NO 588
<211> LENGTH: 33
<212> TYPE: DNA
<213> ORGANISM: Homo Sapiens

<400> SEQUENCE: 588
acagaatggg acaagcratt ccatacatag ttt                                   33

<210> SEQ ID NO 589
<211> LENGTH: 33
<212> TYPE: DNA
<213> ORGANISM: Homo Sapiens

<400> SEQUENCE: 589
ggcaaatcat agtagaragg aagcaactcc aca                                   33

<210> SEQ ID NO 590
<211> LENGTH: 33
<212> TYPE: DNA
<213> ORGANISM: Homo Sapiens

<400> SEQUENCE: 590
aggcagaatg cattgaycca ggaagcaggg ggt                                   33

<210> SEQ ID NO 591
<211> LENGTH: 33
<212> TYPE: DNA
<213> ORGANISM: Homo Sapiens

<400> SEQUENCE: 591
taaaaatttt ctcaacmagt tgaccgatat tct                                   33
```

<210> SEQ ID NO 592
<211> LENGTH: 33
<212> TYPE: DNA
<213> ORGANISM: Homo Sapiens

<400> SEQUENCE: 592
gatgatacca ttgaagwcca gagaggttaa tta                33

<210> SEQ ID NO 593
<211> LENGTH: 33
<212> TYPE: DNA
<213> ORGANISM: Homo Sapiens

<400> SEQUENCE: 593
ctgaaggaag aacaaasagg cctccagtcc tgc                33

<210> SEQ ID NO 594
<211> LENGTH: 33
<212> TYPE: DNA
<213> ORGANISM: Homo Sapiens

<400> SEQUENCE: 594
catccccttc agaaatract gcttccttct ccg                33

<210> SEQ ID NO 595
<211> LENGTH: 33
<212> TYPE: DNA
<213> ORGANISM: Homo Sapiens

<400> SEQUENCE: 595
aagtgcccag actccartac tctcgacctt ggc                33

<210> SEQ ID NO 596
<211> LENGTH: 33
<212> TYPE: DNA
<213> ORGANISM: Homo Sapiens

<400> SEQUENCE: 596
cctgcattta tataggmaag aagcaggtga aaa                33

<210> SEQ ID NO 597
<211> LENGTH: 33
<212> TYPE: DNA
<213> ORGANISM: Homo Sapiens

<400> SEQUENCE: 597
aaaactttca gcatccsata tagtaaaatt ctc                33

<210> SEQ ID NO 598
<211> LENGTH: 33
<212> TYPE: DNA
<213> ORGANISM: Homo Sapiens

<400> SEQUENCE: 598
tcaggagatg gtcgcaraga ttttccaata cct                33

<210> SEQ ID NO 599
<211> LENGTH: 33
<212> TYPE: DNA
<213> ORGANISM: Homo Sapiens

<400> SEQUENCE: 599
gtgagggcat cagtacmcat gcttctgtcc tgg                33

```
<210> SEQ ID NO 600
<211> LENGTH: 33
<212> TYPE: DNA
<213> ORGANISM: Homo Sapiens

<400> SEQUENCE: 600
atattttcag tgatgcraca ttattgagta tag                                33

<210> SEQ ID NO 601
<211> LENGTH: 33
<212> TYPE: DNA
<213> ORGANISM: Homo Sapiens

<400> SEQUENCE: 601
ggctgcctac cacatayact aatttcatta agg                                33

<210> SEQ ID NO 602
<211> LENGTH: 33
<212> TYPE: DNA
<213> ORGANISM: Homo Sapiens

<400> SEQUENCE: 602
aaaatagcca tgtgagwaaa acaattttgt aga                                33

<210> SEQ ID NO 603
<211> LENGTH: 33
<212> TYPE: DNA
<213> ORGANISM: Homo Sapiens

<400> SEQUENCE: 603
tttcctggtt ttatgaygcc attttctagt tct                                33

<210> SEQ ID NO 604
<211> LENGTH: 33
<212> TYPE: DNA
<213> ORGANISM: Homo Sapiens

<400> SEQUENCE: 604
aacacatctt ttccatyatc tggattctgc cta                                33

<210> SEQ ID NO 605
<211> LENGTH: 33
<212> TYPE: DNA
<213> ORGANISM: Homo Sapiens

<400> SEQUENCE: 605
cctgcaaagt catagaygtg tttattttc ctt                                 33

<210> SEQ ID NO 606
<211> LENGTH: 33
<212> TYPE: DNA
<213> ORGANISM: Homo Sapiens

<400> SEQUENCE: 606
aactgtctca gccaaaraga aggcactaac atg                                33

<210> SEQ ID NO 607
<211> LENGTH: 33
<212> TYPE: DNA
<213> ORGANISM: Homo Sapiens

<400> SEQUENCE: 607
```

-continued acacttcctt tgatgcmcaa atcacataag act         33

<210> SEQ ID NO 608
<211> LENGTH: 33
<212> TYPE: DNA
<213> ORGANISM: Homo Sapiens

<400> SEQUENCE: 608
cccagtggta atctcaygtc ttaaaaagtt ttc         33

<210> SEQ ID NO 609
<211> LENGTH: 33
<212> TYPE: DNA
<213> ORGANISM: Homo Sapiens

<400> SEQUENCE: 609
ttttggtcag atgttawctt ttgctacttg cag         33

<210> SEQ ID NO 610
<211> LENGTH: 33
<212> TYPE: DNA
<213> ORGANISM: Homo Sapiens

<400> SEQUENCE: 610
aatgtttagt caataaraaa agtccagggt tgt         33

<210> SEQ ID NO 611
<211> LENGTH: 33
<212> TYPE: DNA
<213> ORGANISM: Homo Sapiens

<400> SEQUENCE: 611
atgtcctcta atagaayaca catccctgac tct         33

<210> SEQ ID NO 612
<211> LENGTH: 33
<212> TYPE: DNA
<213> ORGANISM: Homo Sapiens

<400> SEQUENCE: 612
aggaatggcg gccatcraca ttgccaacat gag         33

<210> SEQ ID NO 613
<211> LENGTH: 33
<212> TYPE: DNA
<213> ORGANISM: Homo Sapiens

<400> SEQUENCE: 613
ggaactgcat cgggcasgcg ttcgccatgg cga         33

<210> SEQ ID NO 614
<211> LENGTH: 33
<212> TYPE: DNA
<213> ORGANISM: Homo Sapiens

<400> SEQUENCE: 614
ctcctctcag tttctcrgaa cccagtctct gcc         33

<210> SEQ ID NO 615
<211> LENGTH: 33
<212> TYPE: DNA
<213> ORGANISM: Homo Sapiens

<400> SEQUENCE: 615
tgaatgaact ggaccargat cagcaaagct gcc                                    33

<210> SEQ ID NO 616
<211> LENGTH: 33
<212> TYPE: DNA
<213> ORGANISM: Homo Sapiens

<400> SEQUENCE: 616
ggagggccag tccctgyacc ttgtctgtgc tgt                                    33

<210> SEQ ID NO 617
<211> LENGTH: 33
<212> TYPE: DNA
<213> ORGANISM: Homo Sapiens

<400> SEQUENCE: 617
aaccttttca tatttcrcat ttcaaatagg aca                                    33

<210> SEQ ID NO 618
<211> LENGTH: 33
<212> TYPE: DNA
<213> ORGANISM: Homo Sapiens

<400> SEQUENCE: 618
cctcccccat tccagawatt tggaccgacc ctg                                    33

<210> SEQ ID NO 619
<211> LENGTH: 33
<212> TYPE: DNA
<213> ORGANISM: Homo Sapiens

<400> SEQUENCE: 619
ggctgaggcc ggcggarctc ttgaagtcag gag                                    33

<210> SEQ ID NO 620
<211> LENGTH: 33
<212> TYPE: DNA
<213> ORGANISM: Homo Sapiens

<400> SEQUENCE: 620
aactctctga gcagcarattt aagtggagaa tga                                   33

<210> SEQ ID NO 621
<211> LENGTH: 33
<212> TYPE: DNA
<213> ORGANISM: Homo Sapiens

<400> SEQUENCE: 621
tctgtatggg atgagayaag gtagaagcca atg                                    33

<210> SEQ ID NO 622
<211> LENGTH: 33
<212> TYPE: DNA
<213> ORGANISM: Homo Sapiens

<400> SEQUENCE: 622
gctagattcc tcctcakgtc tactgatttg gaa                                    33

<210> SEQ ID NO 623
<211> LENGTH: 33
<212> TYPE: DNA
<213> ORGANISM: Homo Sapiens

<400> SEQUENCE: 623
tatgagaggt cctcgayaaa tatttgtgga aag                33

<210> SEQ ID NO 624
<211> LENGTH: 33
<212> TYPE: DNA
<213> ORGANISM: Homo Sapiens

<400> SEQUENCE: 624
tttgtgtaag gggcacsaga tttccactga ata                33

<210> SEQ ID NO 625
<211> LENGTH: 33
<212> TYPE: DNA
<213> ORGANISM: Homo Sapiens

<400> SEQUENCE: 625
ttgaacaaag aaaagtmaat ccaatccagg tgt                33

<210> SEQ ID NO 626
<211> LENGTH: 33
<212> TYPE: DNA
<213> ORGANISM: Homo Sapiens

<400> SEQUENCE: 626
caacagagtg aaggacyggc tacataactt gta                33

<210> SEQ ID NO 627
<211> LENGTH: 33
<212> TYPE: DNA
<213> ORGANISM: Homo Sapiens

<400> SEQUENCE: 627
tttatgtcag cactggrata ctttctcctt atg                33

<210> SEQ ID NO 628
<211> LENGTH: 33
<212> TYPE: DNA
<213> ORGANISM: Homo Sapiens

<400> SEQUENCE: 628
agtcaacaca tcagcawtga agatcacaca atg                33

<210> SEQ ID NO 629
<211> LENGTH: 33
<212> TYPE: DNA
<213> ORGANISM: Homo Sapiens

<400> SEQUENCE: 629
agttctgaat tctaacygta gcttttttggg ctt                33

<210> SEQ ID NO 630
<211> LENGTH: 33
<212> TYPE: DNA
<213> ORGANISM: Homo Sapiens

<400> SEQUENCE: 630
gccacagtcc atctcaygtt aacaaatgcc ttt                33

<210> SEQ ID NO 631
<211> LENGTH: 33
<212> TYPE: DNA
<213> ORGANISM: Homo Sapiens

```
<400> SEQUENCE: 631
gactgctcca ctgtcaraac agaaactaga ttc                              33

<210> SEQ ID NO 632
<211> LENGTH: 33
<212> TYPE: DNA
<213> ORGANISM: Homo Sapiens

<400> SEQUENCE: 632
atatttattt ttcagartag tgactgagtt cag                              33

<210> SEQ ID NO 633
<211> LENGTH: 33
<212> TYPE: DNA
<213> ORGANISM: Homo Sapiens

<400> SEQUENCE: 633
aacaaaaaaa gttaaasctg tctgaaggtg aaa                              33

<210> SEQ ID NO 634
<211> LENGTH: 33
<212> TYPE: DNA
<213> ORGANISM: Homo Sapiens

<400> SEQUENCE: 634
attataagat tgagagrcca ttgccccagg cag                              33

<210> SEQ ID NO 635
<211> LENGTH: 33
<212> TYPE: DNA
<213> ORGANISM: Homo Sapiens

<400> SEQUENCE: 635
ttcagagatg aacgcgsaga cacctgtgac ctc                              33

<210> SEQ ID NO 636
<211> LENGTH: 33
<212> TYPE: DNA
<213> ORGANISM: Homo Sapiens

<400> SEQUENCE: 636
ctgtactttg ctgtcawcta tgaaaagaaa aag                              33

<210> SEQ ID NO 637
<211> LENGTH: 33
<212> TYPE: DNA
<213> ORGANISM: Homo Sapiens

<400> SEQUENCE: 637
caaaaaagtc aagctgsaga cagggcgttg gag                              33

<210> SEQ ID NO 638
<211> LENGTH: 33
<212> TYPE: DNA
<213> ORGANISM: Homo Sapiens

<400> SEQUENCE: 638
actgactaag agttcawctt ggcacttact gtc                              33

<210> SEQ ID NO 639
<211> LENGTH: 33
<212> TYPE: DNA
```

<213> ORGANISM: Homo Sapiens

<400> SEQUENCE: 639
gctgggctgg agaaagratt acaatttaca gac                33

<210> SEQ ID NO 640
<211> LENGTH: 33
<212> TYPE: DNA
<213> ORGANISM: Homo Sapiens

<400> SEQUENCE: 640
ctcacagctc cactccratc ctggagtcat cgc                33

<210> SEQ ID NO 641
<211> LENGTH: 33
<212> TYPE: DNA
<213> ORGANISM: Homo Sapiens

<400> SEQUENCE: 641
ttccacttct gattggyagg gcacgctgat tgg                33

<210> SEQ ID NO 642
<211> LENGTH: 33
<212> TYPE: DNA
<213> ORGANISM: Homo Sapiens

<400> SEQUENCE: 642
agtgagagct aaactayggt tcgcaaaggc aga                33

<210> SEQ ID NO 643
<211> LENGTH: 33
<212> TYPE: DNA
<213> ORGANISM: Homo Sapiens

<400> SEQUENCE: 643
aggctgcact ttggtcrcat taattccctg aca                33

<210> SEQ ID NO 644
<211> LENGTH: 33
<212> TYPE: DNA
<213> ORGANISM: Homo Sapiens

<400> SEQUENCE: 644
acttgaaagg ctagackatt cactcaacac ata                33

<210> SEQ ID NO 645
<211> LENGTH: 33
<212> TYPE: DNA
<213> ORGANISM: Homo Sapiens

<400> SEQUENCE: 645
gtcaccactc taaacayagg gctttgtgca tgc                33

<210> SEQ ID NO 646
<211> LENGTH: 33
<212> TYPE: DNA
<213> ORGANISM: Homo Sapiens

<400> SEQUENCE: 646
gaaggtttgg aaggtcraaa tcaaggactc ttt                33

<210> SEQ ID NO 647
<211> LENGTH: 33

```
<212> TYPE: DNA
<213> ORGANISM: Homo Sapiens

<400> SEQUENCE: 647
actataattc tttcacrcta tttctgcatt ctc                              33

<210> SEQ ID NO 648
<211> LENGTH: 33
<212> TYPE: DNA
<213> ORGANISM: Homo Sapiens

<400> SEQUENCE: 648
tgtgtttaac cacatcsagt tttagcagag cac                              33

<210> SEQ ID NO 649
<211> LENGTH: 33
<212> TYPE: DNA
<213> ORGANISM: Homo Sapiens

<400> SEQUENCE: 649
gtctctgccc aaaagcrcct agaacttata aat                              33

<210> SEQ ID NO 650
<211> LENGTH: 33
<212> TYPE: DNA
<213> ORGANISM: Homo Sapiens

<400> SEQUENCE: 650
tttctcaagc ctggaayata gtgcatagct ctt                              33

<210> SEQ ID NO 651
<211> LENGTH: 33
<212> TYPE: DNA
<213> ORGANISM: Homo Sapiens

<400> SEQUENCE: 651
agagagagct tgtgccraga aattcctgtt ttt                              33

<210> SEQ ID NO 652
<211> LENGTH: 33
<212> TYPE: DNA
<213> ORGANISM: Homo Sapiens

<400> SEQUENCE: 652
tatgctgtct tcaaaaraac aatctcacat gca                              33

<210> SEQ ID NO 653
<211> LENGTH: 33
<212> TYPE: DNA
<213> ORGANISM: Homo Sapiens

<400> SEQUENCE: 653
tcatatcagc caaaacraat ctttcattt ctt                               33

<210> SEQ ID NO 654
<211> LENGTH: 33
<212> TYPE: DNA
<213> ORGANISM: Homo Sapiens

<400> SEQUENCE: 654
caataaattc tgaaaartca aaatcacatc gag                              33

<210> SEQ ID NO 655
```

```
<211> LENGTH: 33
<212> TYPE: DNA
<213> ORGANISM: Homo Sapiens

<400> SEQUENCE: 655
atctgataca agcctaraca gtacatttaa cgt                                   33

<210> SEQ ID NO 656
<211> LENGTH: 33
<212> TYPE: DNA
<213> ORGANISM: Homo Sapiens

<400> SEQUENCE: 656
caggtaagtc ttcatamcca tcctacacac cct                                   33

<210> SEQ ID NO 657
<211> LENGTH: 33
<212> TYPE: DNA
<213> ORGANISM: Homo Sapiens

<400> SEQUENCE: 657
tttgcagttt agcacartaa tacaaacttt gta                                   33

<210> SEQ ID NO 658
<211> LENGTH: 33
<212> TYPE: DNA
<213> ORGANISM: Homo Sapiens

<400> SEQUENCE: 658
tctgctttgc aaacaamgga aatgatagca aag                                   33

<210> SEQ ID NO 659
<211> LENGTH: 33
<212> TYPE: DNA
<213> ORGANISM: Homo Sapiens

<400> SEQUENCE: 659
ctggctagcc acgtgcmgag gaattaaagt gga                                   33

<210> SEQ ID NO 660
<211> LENGTH: 33
<212> TYPE: DNA
<213> ORGANISM: Homo Sapiens

<400> SEQUENCE: 660
taggcagaga gctaccsagt aaggttcacc ttt                                   33

<210> SEQ ID NO 661
<211> LENGTH: 33
<212> TYPE: DNA
<213> ORGANISM: Homo Sapiens

<400> SEQUENCE: 661
tatgatgtta ggtatcrctt ttcatatatg gcc                                   33

<210> SEQ ID NO 662
<211> LENGTH: 33
<212> TYPE: DNA
<213> ORGANISM: Homo Sapiens

<400> SEQUENCE: 662
ttcactgaac ttcccamagc tttttgtcac tct                                   33
```

<210> SEQ ID NO 663
<211> LENGTH: 33
<212> TYPE: DNA
<213> ORGANISM: Homo Sapiens

<400> SEQUENCE: 663
tgtggcttac ccttgcraaa cagattcact aag                           33

<210> SEQ ID NO 664
<211> LENGTH: 33
<212> TYPE: DNA
<213> ORGANISM: Homo Sapiens

<400> SEQUENCE: 664
attctaggat ccggtaygtt tcatagccac ttt                           33

<210> SEQ ID NO 665
<211> LENGTH: 33
<212> TYPE: DNA
<213> ORGANISM: Homo Sapiens

<400> SEQUENCE: 665
tttggaaagc aagaaartac atatccctca gta                           33

<210> SEQ ID NO 666
<211> LENGTH: 33
<212> TYPE: DNA
<213> ORGANISM: Homo Sapiens

<400> SEQUENCE: 666
caagtgtaga cccaaartaa ctgaaaacag gtg                           33

<210> SEQ ID NO 667
<211> LENGTH: 33
<212> TYPE: DNA
<213> ORGANISM: Homo Sapiens

<400> SEQUENCE: 667
ccttgtgaat gcgccayctg ggaagaggac cct                           33

<210> SEQ ID NO 668
<211> LENGTH: 33
<212> TYPE: DNA
<213> ORGANISM: Homo Sapiens

<400> SEQUENCE: 668
agagaagaag tgtgacrgcc cagatcacaa gca                           33

<210> SEQ ID NO 669
<211> LENGTH: 33
<212> TYPE: DNA
<213> ORGANISM: Homo Sapiens

<400> SEQUENCE: 669
aaatttttat atggtcragt ctaccaaacc ttg                           33

<210> SEQ ID NO 670
<211> LENGTH: 33
<212> TYPE: DNA
<213> ORGANISM: Homo Sapiens

<400> SEQUENCE: 670
tgatggtggc tggatawaaa gactggagaa ggc                           33

```
<210> SEQ ID NO 671
<211> LENGTH: 33
<212> TYPE: DNA
<213> ORGANISM: Homo Sapiens

<400> SEQUENCE: 671
agaaggacag cagaggragt aaccaacact atc                                33

<210> SEQ ID NO 672
<211> LENGTH: 33
<212> TYPE: DNA
<213> ORGANISM: Homo Sapiens

<400> SEQUENCE: 672
atgtctcctc tagctaygaa tattgatggt gat                                33

<210> SEQ ID NO 673
<211> LENGTH: 33
<212> TYPE: DNA
<213> ORGANISM: Homo Sapiens

<400> SEQUENCE: 673
gtgtaaccaa ccgtaayggc ctgtcctgtt act                                33

<210> SEQ ID NO 674
<211> LENGTH: 33
<212> TYPE: DNA
<213> ORGANISM: Homo Sapiens

<400> SEQUENCE: 674
tgtggaatag caacaarcta agtaaactaa aca                                33

<210> SEQ ID NO 675
<211> LENGTH: 33
<212> TYPE: DNA
<213> ORGANISM: Homo Sapiens

<400> SEQUENCE: 675
aggtagtcta gccacaraaa ctgcagttgc tgg                                33

<210> SEQ ID NO 676
<211> LENGTH: 33
<212> TYPE: DNA
<213> ORGANISM: Homo Sapiens

<400> SEQUENCE: 676
tcctgcatga ttacaastga gtgagaactg ccc                                33

<210> SEQ ID NO 677
<211> LENGTH: 33
<212> TYPE: DNA
<213> ORGANISM: Homo Sapiens

<400> SEQUENCE: 677
atttaaataa agaaaamgca tggagcctga ggg                                33

<210> SEQ ID NO 678
<211> LENGTH: 33
<212> TYPE: DNA
<213> ORGANISM: Homo Sapiens

<400> SEQUENCE: 678
gcgtagagaa taatcayatt gttgttgagt aac                                33
```

<210> SEQ ID NO 679
<211> LENGTH: 33
<212> TYPE: DNA
<213> ORGANISM: Homo Sapiens

<400> SEQUENCE: 679
tagacgtaaa taacagrcaa tctaaatcaa act         33

<210> SEQ ID NO 680
<211> LENGTH: 33
<212> TYPE: DNA
<213> ORGANISM: Homo Sapiens

<400> SEQUENCE: 680
caggtaagga gttcaaytgg ataaggccac tta         33

<210> SEQ ID NO 681
<211> LENGTH: 33
<212> TYPE: DNA
<213> ORGANISM: Homo Sapiens

<400> SEQUENCE: 681
tgagctttat gaaggartat gcttccatag tgt         33

<210> SEQ ID NO 682
<211> LENGTH: 33
<212> TYPE: DNA
<213> ORGANISM: Homo Sapiens

<400> SEQUENCE: 682
attagaacaa gggctayaga tgagtattgt ctg         33

<210> SEQ ID NO 683
<211> LENGTH: 33
<212> TYPE: DNA
<213> ORGANISM: Homo Sapiens

<400> SEQUENCE: 683
ggtgccctgg actaaayatc cctggaggaa acc         33

<210> SEQ ID NO 684
<211> LENGTH: 33
<212> TYPE: DNA
<213> ORGANISM: Homo Sapiens

<400> SEQUENCE: 684
ggcaaaataa acattcyaga tcgactgaga tgt         33

<210> SEQ ID NO 685
<211> LENGTH: 33
<212> TYPE: DNA
<213> ORGANISM: Homo Sapiens

<400> SEQUENCE: 685
gtaggcttcc gttcccrcac acggatctct cca         33

<210> SEQ ID NO 686
<211> LENGTH: 33
<212> TYPE: DNA
<213> ORGANISM: Homo Sapiens

<400> SEQUENCE: 686
ctcagatgag acttcgraca tggactttg agt                    33

<210> SEQ ID NO 687
<211> LENGTH: 33
<212> TYPE: DNA
<213> ORGANISM: Homo Sapiens

<400> SEQUENCE: 687
agtaattcaa ataacartga tggctgggca cag                    33

<210> SEQ ID NO 688
<211> LENGTH: 33
<212> TYPE: DNA
<213> ORGANISM: Homo Sapiens

<400> SEQUENCE: 688
ctgcctgtga gtcaaaytgg cgcctctgac caa                    33

<210> SEQ ID NO 689
<211> LENGTH: 33
<212> TYPE: DNA
<213> ORGANISM: Homo Sapiens

<400> SEQUENCE: 689
cctcaaggag taaaacrgca atcccacata agt                    33

<210> SEQ ID NO 690
<211> LENGTH: 33
<212> TYPE: DNA
<213> ORGANISM: Homo Sapiens

<400> SEQUENCE: 690
ggaaatcagc aatccartct tctccttttt tgt                    33

<210> SEQ ID NO 691
<211> LENGTH: 33
<212> TYPE: DNA
<213> ORGANISM: Homo Sapiens

<400> SEQUENCE: 691
gccttcagat gttatawgtg atgttttatc aac                    33

<210> SEQ ID NO 692
<211> LENGTH: 33
<212> TYPE: DNA
<213> ORGANISM: Homo Sapiens

<400> SEQUENCE: 692
acaggtatat ctcaagmctg gcacatagta att                    33

<210> SEQ ID NO 693
<211> LENGTH: 33
<212> TYPE: DNA
<213> ORGANISM: Homo Sapiens

<400> SEQUENCE: 693
ttgtttgcag aagacawcta gtatcaatgc aca                    33

<210> SEQ ID NO 694
<211> LENGTH: 33
<212> TYPE: DNA
<213> ORGANISM: Homo Sapiens

<400> SEQUENCE: 694
ttttttttag cttgcawgga agaacacact cca                                        33

<210> SEQ ID NO 695
<211> LENGTH: 33
<212> TYPE: DNA
<213> ORGANISM: Homo Sapiens

<400> SEQUENCE: 695
cctgaccaga gcattayatt tcatgcattc cca                                        33

<210> SEQ ID NO 696
<211> LENGTH: 33
<212> TYPE: DNA
<213> ORGANISM: Homo Sapiens

<400> SEQUENCE: 696
gattcagaga ggtaaastta ctcttccaag gct                                        33

<210> SEQ ID NO 697
<211> LENGTH: 33
<212> TYPE: DNA
<213> ORGANISM: Homo Sapiens

<400> SEQUENCE: 697
accatgacag ttacaaycat atgttgatat gaa                                        33

<210> SEQ ID NO 698
<211> LENGTH: 33
<212> TYPE: DNA
<213> ORGANISM: Homo Sapiens

<400> SEQUENCE: 698
tacctgtatt atagcartga ctatcatcca gca                                        33

<210> SEQ ID NO 699
<211> LENGTH: 33
<212> TYPE: DNA
<213> ORGANISM: Homo Sapiens

<400> SEQUENCE: 699
gtgtcttgtg acttggyatg atatgcaggg aat                                        33

<210> SEQ ID NO 700
<211> LENGTH: 33
<212> TYPE: DNA
<213> ORGANISM: Homo Sapiens

<400> SEQUENCE: 700
attatctaat gcagaartaa tagattatcc cca                                        33

<210> SEQ ID NO 701
<211> LENGTH: 33
<212> TYPE: DNA
<213> ORGANISM: Homo Sapiens

<400> SEQUENCE: 701
gatgactcca aagcaaytcc ttgcaaaaca aat                                        33

<210> SEQ ID NO 702
<211> LENGTH: 33
<212> TYPE: DNA
<213> ORGANISM: Homo Sapiens

<400> SEQUENCE: 702
tctctggctt ccaagaytag aaaaaataaa gat          33

<210> SEQ ID NO 703
<211> LENGTH: 33
<212> TYPE: DNA
<213> ORGANISM: Homo Sapiens

<400> SEQUENCE: 703
caactctacc actggaragt gaacacagct gaa          33

<210> SEQ ID NO 704
<211> LENGTH: 33
<212> TYPE: DNA
<213> ORGANISM: Homo Sapiens

<400> SEQUENCE: 704
aacccttctt agacaasaaa gcagaatttg gtt          33

<210> SEQ ID NO 705
<211> LENGTH: 33
<212> TYPE: DNA
<213> ORGANISM: Homo Sapiens

<400> SEQUENCE: 705
tttctgctga ggtttcmctt ggctcctaac atg          33

<210> SEQ ID NO 706
<211> LENGTH: 33
<212> TYPE: DNA
<213> ORGANISM: Homo Sapiens

<400> SEQUENCE: 706
cacatatggt tcagcawgac atcaacttgt cct          33

<210> SEQ ID NO 707
<211> LENGTH: 33
<212> TYPE: DNA
<213> ORGANISM: Homo Sapiens

<400> SEQUENCE: 707
atcaatgttt gataaaytgg acaaagggaa agg          33

<210> SEQ ID NO 708
<211> LENGTH: 33
<212> TYPE: DNA
<213> ORGANISM: Homo Sapiens

<400> SEQUENCE: 708
ttgaggtaaa tttgagsatt ctatgtattg cat          33

<210> SEQ ID NO 709
<211> LENGTH: 33
<212> TYPE: DNA
<213> ORGANISM: Homo Sapiens

<400> SEQUENCE: 709
cctctgatga agtgaamgta tctactgctg atg          33

<210> SEQ ID NO 710
<211> LENGTH: 33
<212> TYPE: DNA
<213> ORGANISM: Homo Sapiens

<400> SEQUENCE: 710
atcagtacgg ctttcartaa tggtgatgaa caa          33

<210> SEQ ID NO 711
<211> LENGTH: 33
<212> TYPE: DNA
<213> ORGANISM: Homo Sapiens

<400> SEQUENCE: 711
agtgtatgag tttctcrctg tgcctggccc att          33

<210> SEQ ID NO 712
<211> LENGTH: 33
<212> TYPE: DNA
<213> ORGANISM: Homo Sapiens

<400> SEQUENCE: 712
gaattagagt cacacaygca atgagtgtat gag          33

<210> SEQ ID NO 713
<211> LENGTH: 33
<212> TYPE: DNA
<213> ORGANISM: Homo Sapiens

<400> SEQUENCE: 713
agaacccaaa ctaagasatc gattttggta gaa          33

<210> SEQ ID NO 714
<211> LENGTH: 33
<212> TYPE: DNA
<213> ORGANISM: Homo Sapiens

<400> SEQUENCE: 714
cacgagtaaa ttagaargag tctatgttat gtt          33

<210> SEQ ID NO 715
<211> LENGTH: 33
<212> TYPE: DNA
<213> ORGANISM: Homo Sapiens

<400> SEQUENCE: 715
ttatcatacg ctgaaarccg tacacgtaac aat          33

<210> SEQ ID NO 716
<211> LENGTH: 33
<212> TYPE: DNA
<213> ORGANISM: Homo Sapiens

<400> SEQUENCE: 716
gcagaccccc taaaagrcca ttcaatgcca ttc          33

<210> SEQ ID NO 717
<211> LENGTH: 33
<212> TYPE: DNA
<213> ORGANISM: Homo Sapiens

<400> SEQUENCE: 717
tctctttgaa aaagtckctt gaaggctgga gat          33

<210> SEQ ID NO 718
<211> LENGTH: 33
<212> TYPE: DNA

<213> ORGANISM: Homo Sapiens

<400> SEQUENCE: 718
gcatccatga aaatgwagc tttctagaac tca                33

<210> SEQ ID NO 719
<211> LENGTH: 33
<212> TYPE: DNA
<213> ORGANISM: Homo Sapiens

<400> SEQUENCE: 719
tcgttgcaat tatcccraac ttctttccac ttc                33

<210> SEQ ID NO 720
<211> LENGTH: 33
<212> TYPE: DNA
<213> ORGANISM: Homo Sapiens

<400> SEQUENCE: 720
gctctgcaaa cagctcyaca aagaccataa atg                33

<210> SEQ ID NO 721
<211> LENGTH: 33
<212> TYPE: DNA
<213> ORGANISM: Homo Sapiens

<400> SEQUENCE: 721
ttgaccctag acatacwcat attagcaggt tgt                33

<210> SEQ ID NO 722
<211> LENGTH: 33
<212> TYPE: DNA
<213> ORGANISM: Homo Sapiens

<400> SEQUENCE: 722
aaatatatgg aaacaarcta tatgatttga tat                33

<210> SEQ ID NO 723
<211> LENGTH: 33
<212> TYPE: DNA
<213> ORGANISM: Homo Sapiens

<400> SEQUENCE: 723
aggccaactt ctcaacygtt cctgttgctc ctc                33

<210> SEQ ID NO 724
<211> LENGTH: 33
<212> TYPE: DNA
<213> ORGANISM: Homo Sapiens

<400> SEQUENCE: 724
tctcagtaga catcgayaag gcagtaaata aat                33

<210> SEQ ID NO 725
<211> LENGTH: 33
<212> TYPE: DNA
<213> ORGANISM: Homo Sapiens

<400> SEQUENCE: 725
atgcaatgga gtgttayaag gccctggaac agc                33

<210> SEQ ID NO 726
<211> LENGTH: 33

<212> TYPE: DNA
<213> ORGANISM: Homo Sapiens

<400> SEQUENCE: 726
ctgtaaaact agtacargtg aagttgggat tca                                    33

<210> SEQ ID NO 727
<211> LENGTH: 33
<212> TYPE: DNA
<213> ORGANISM: Homo Sapiens

<400> SEQUENCE: 727
agtccaaagc tctaacygaa gctagtgcca aaa                                    33

<210> SEQ ID NO 728
<211> LENGTH: 33
<212> TYPE: DNA
<213> ORGANISM: Homo Sapiens

<400> SEQUENCE: 728
gggactgaat tcctcakcct ttgtagcaca cga                                    33

<210> SEQ ID NO 729
<211> LENGTH: 33
<212> TYPE: DNA
<213> ORGANISM: Homo Sapiens

<400> SEQUENCE: 729
gaactcagta ctgaaasgtg atccccggag tgc                                    33

<210> SEQ ID NO 730
<211> LENGTH: 33
<212> TYPE: DNA
<213> ORGANISM: Homo Sapiens

<400> SEQUENCE: 730
cagttgaaca cagatcraac tccttgttct aca                                    33

<210> SEQ ID NO 731
<211> LENGTH: 33
<212> TYPE: DNA
<213> ORGANISM: Homo Sapiens

<400> SEQUENCE: 731
tgtatctgtt gaaaacratt agcaccaaga agc                                    33

<210> SEQ ID NO 732
<211> LENGTH: 33
<212> TYPE: DNA
<213> ORGANISM: Homo Sapiens

<400> SEQUENCE: 732
cctaattgtt gtaagaytcc attgctgtct ctt                                    33

<210> SEQ ID NO 733
<211> LENGTH: 33
<212> TYPE: DNA
<213> ORGANISM: Homo Sapiens

<400> SEQUENCE: 733
ttttctagac caaaaakgca gttgtgttct aat                                    33

<210> SEQ ID NO 734

```
<211> LENGTH: 33
<212> TYPE: DNA
<213> ORGANISM: Homo Sapiens

<400> SEQUENCE: 734
tcttgatgac tgtcccyaaa tgataatgaa gca                                  33

<210> SEQ ID NO 735
<211> LENGTH: 33
<212> TYPE: DNA
<213> ORGANISM: Homo Sapiens

<400> SEQUENCE: 735
ccttatccat gtgaacrgga gagcttcctc gtt                                  33

<210> SEQ ID NO 736
<211> LENGTH: 33
<212> TYPE: DNA
<213> ORGANISM: Homo Sapiens

<400> SEQUENCE: 736
tttcttaccc ttgttcyctg tatatcaatg gtt                                  33

<210> SEQ ID NO 737
<211> LENGTH: 33
<212> TYPE: DNA
<213> ORGANISM: Homo Sapiens

<400> SEQUENCE: 737
ttgagttctc aagataygtg tacaaattgc ggt                                  33

<210> SEQ ID NO 738
<211> LENGTH: 33
<212> TYPE: DNA
<213> ORGANISM: Homo Sapiens

<400> SEQUENCE: 738
agacagctgt gtctackgcc gattggctgt acg                                  33

<210> SEQ ID NO 739
<211> LENGTH: 33
<212> TYPE: DNA
<213> ORGANISM: Homo Sapiens

<400> SEQUENCE: 739
agaaaagttg agttaawtga acttcagaag gac                                  33

<210> SEQ ID NO 740
<211> LENGTH: 33
<212> TYPE: DNA
<213> ORGANISM: Homo Sapiens

<400> SEQUENCE: 740
agtaacaagg taaaaarttt tgctccaaga tcg                                  33

<210> SEQ ID NO 741
<211> LENGTH: 33
<212> TYPE: DNA
<213> ORGANISM: Homo Sapiens

<400> SEQUENCE: 741
atctcccctc tcattcratc agatagataa aga                                  33
```

```
<210> SEQ ID NO 742
<211> LENGTH: 33
<212> TYPE: DNA
<213> ORGANISM: Homo Sapiens

<400> SEQUENCE: 742
atatgcaaac ttatcartca gaactcaccc ctc                                    33

<210> SEQ ID NO 743
<211> LENGTH: 33
<212> TYPE: DNA
<213> ORGANISM: Homo Sapiens

<400> SEQUENCE: 743
atatatttgg attttayact taaataggtc ggt                                    33

<210> SEQ ID NO 744
<211> LENGTH: 33
<212> TYPE: DNA
<213> ORGANISM: Homo Sapiens

<400> SEQUENCE: 744
ttcacttcac cttatcmacc tactactgag ata                                    33

<210> SEQ ID NO 745
<211> LENGTH: 33
<212> TYPE: DNA
<213> ORGANISM: Homo Sapiens

<400> SEQUENCE: 745
aatatacatt caatggrcat gaaaaaatgc agc                                    33

<210> SEQ ID NO 746
<211> LENGTH: 33
<212> TYPE: DNA
<213> ORGANISM: Homo Sapiens

<400> SEQUENCE: 746
tcagggtgac tattagraga ggaaaaatct aaa                                    33

<210> SEQ ID NO 747
<211> LENGTH: 33
<212> TYPE: DNA
<213> ORGANISM: Homo Sapiens

<400> SEQUENCE: 747
ttccaaattc tccaacmgaa gagtctccta ttc                                    33

<210> SEQ ID NO 748
<211> LENGTH: 33
<212> TYPE: DNA
<213> ORGANISM: Homo Sapiens

<400> SEQUENCE: 748
gaccacatca aagaaasgac catagacata aga                                    33

<210> SEQ ID NO 749
<211> LENGTH: 33
<212> TYPE: DNA
<213> ORGANISM: Homo Sapiens

<400> SEQUENCE: 749
tactgaggtt tgtaaaragt tgcgaactgc tga                                    33
```

<210> SEQ ID NO 750
<211> LENGTH: 33
<212> TYPE: DNA
<213> ORGANISM: Homo Sapiens

<400> SEQUENCE: 750
ttctgcgtgt ccggartaa ctttctccac tcc                33

<210> SEQ ID NO 751
<211> LENGTH: 33
<212> TYPE: DNA
<213> ORGANISM: Homo Sapiens

<400> SEQUENCE: 751
cagccatgtt ggaggcrctg tgtgggacac cca                33

<210> SEQ ID NO 752
<211> LENGTH: 33
<212> TYPE: DNA
<213> ORGANISM: Homo Sapiens

<400> SEQUENCE: 752
taatgggaaa tctccastga aatagaaagc aaa                33

<210> SEQ ID NO 753
<211> LENGTH: 33
<212> TYPE: DNA
<213> ORGANISM: Homo Sapiens

<400> SEQUENCE: 753
ggctggcttc tgtcacrgga gaacctgtct aaa                33

<210> SEQ ID NO 754
<211> LENGTH: 33
<212> TYPE: DNA
<213> ORGANISM: Homo Sapiens

<400> SEQUENCE: 754
aggcaagaga gagtccwgag agaatgtact cac                33

<210> SEQ ID NO 755
<211> LENGTH: 33
<212> TYPE: DNA
<213> ORGANISM: Homo Sapiens

<400> SEQUENCE: 755
gaggatcaag tagacaytct ctagatcaag agc                33

<210> SEQ ID NO 756
<211> LENGTH: 33
<212> TYPE: DNA
<213> ORGANISM: Homo Sapiens

<400> SEQUENCE: 756
tctctacggt ctgtcckaga aattcatcaa aga                33

<210> SEQ ID NO 757
<211> LENGTH: 33
<212> TYPE: DNA
<213> ORGANISM: Homo Sapiens

<400> SEQUENCE: 757
tctgccatgt tccagtsaag gggggcaaag gca                33

<210> SEQ ID NO 758
<211> LENGTH: 33
<212> TYPE: DNA
<213> ORGANISM: Homo Sapiens

<400> SEQUENCE: 758
tgcctcctgg agtttarggt aggatcaaat gag                33

<210> SEQ ID NO 759
<211> LENGTH: 33
<212> TYPE: DNA
<213> ORGANISM: Homo Sapiens

<400> SEQUENCE: 759
agaaagtcat ataagaygaa tcacaactct gat                33

<210> SEQ ID NO 760
<211> LENGTH: 33
<212> TYPE: DNA
<213> ORGANISM: Homo Sapiens

<400> SEQUENCE: 760
gaggtctgca agggaaycct gctatggaaa ctt                33

<210> SEQ ID NO 761
<211> LENGTH: 33
<212> TYPE: DNA
<213> ORGANISM: Homo Sapiens

<400> SEQUENCE: 761
gagagcctgc ttacaakcta gggatagagc cca                33

<210> SEQ ID NO 762
<211> LENGTH: 33
<212> TYPE: DNA
<213> ORGANISM: Homo Sapiens

<400> SEQUENCE: 762
ccgacactgt tcatgaygtc aaaggccacg gtg                33

<210> SEQ ID NO 763
<211> LENGTH: 33
<212> TYPE: DNA
<213> ORGANISM: Homo Sapiens

<400> SEQUENCE: 763
ccaagtaatt gggattraag tgtgagaaag tga                33

<210> SEQ ID NO 764
<211> LENGTH: 33
<212> TYPE: DNA
<213> ORGANISM: Homo Sapiens

<400> SEQUENCE: 764
agtgacaagt agacccrgag ataaacaact cga                33

<210> SEQ ID NO 765
<211> LENGTH: 33
<212> TYPE: DNA
<213> ORGANISM: Homo Sapiens

<400> SEQUENCE: 765

```
gacaatccgg tgattgmagg tttgctgtac agt                           33

<210> SEQ ID NO 766
<211> LENGTH: 33
<212> TYPE: DNA
<213> ORGANISM: Homo Sapiens

<400> SEQUENCE: 766
caataaaatt ttattcrcaa taagtgctat aga                           33

<210> SEQ ID NO 767
<211> LENGTH: 33
<212> TYPE: DNA
<213> ORGANISM: Homo Sapiens

<400> SEQUENCE: 767
aaattcacct cagagtmaaa tatgttacag tag                           33

<210> SEQ ID NO 768
<211> LENGTH: 33
<212> TYPE: DNA
<213> ORGANISM: Homo Sapiens

<400> SEQUENCE: 768
attttgggct tttgtargag ggtaacaatt att                           33

<210> SEQ ID NO 769
<211> LENGTH: 33
<212> TYPE: DNA
<213> ORGANISM: Homo Sapiens

<400> SEQUENCE: 769
tactcaagtc attccawctt tcctgtcata agg                           33

<210> SEQ ID NO 770
<211> LENGTH: 33
<212> TYPE: DNA
<213> ORGANISM: Homo Sapiens

<400> SEQUENCE: 770
ccagaggaat actgtgyaat cgttaaaatg cat                           33

<210> SEQ ID NO 771
<211> LENGTH: 33
<212> TYPE: DNA
<213> ORGANISM: Homo Sapiens

<400> SEQUENCE: 771
tcttctcaac acaggaytac cctggaggaa aag                           33

<210> SEQ ID NO 772
<211> LENGTH: 33
<212> TYPE: DNA
<213> ORGANISM: Homo Sapiens

<400> SEQUENCE: 772
gcttttaaaa tcgaaawttg tactcctcat cct                           33

<210> SEQ ID NO 773
<211> LENGTH: 33
<212> TYPE: DNA
<213> ORGANISM: Homo Sapiens

<400> SEQUENCE: 773
```
aggctggtct tgagcarcta ggttcaagga atc                                33

<210> SEQ ID NO 774
<211> LENGTH: 33
<212> TYPE: DNA
<213> ORGANISM: Homo Sapiens

<400> SEQUENCE: 774
cctccaggga caagtgrcaa agccatcagc atg                                33

<210> SEQ ID NO 775
<211> LENGTH: 33
<212> TYPE: DNA
<213> ORGANISM: Homo Sapiens

<400> SEQUENCE: 775
tagagaactt ggtgaaygta aaaatgtatt ttc                                33

<210> SEQ ID NO 776
<211> LENGTH: 33
<212> TYPE: DNA
<213> ORGANISM: Homo Sapiens

<400> SEQUENCE: 776
gtaaaactat gtggctkaat tttcttccat ctc                                33

<210> SEQ ID NO 777
<211> LENGTH: 33
<212> TYPE: DNA
<213> ORGANISM: Homo Sapiens

<400> SEQUENCE: 777
acttctttta cagctckaat ggttcttaca aaa                                33

<210> SEQ ID NO 778
<211> LENGTH: 33
<212> TYPE: DNA
<213> ORGANISM: Homo Sapiens

<400> SEQUENCE: 778
tacattcttc tcagtargcc caccttcagg agt                                33

<210> SEQ ID NO 779
<211> LENGTH: 33
<212> TYPE: DNA
<213> ORGANISM: Homo Sapiens

<400> SEQUENCE: 779
atttccagga gggtcaygtt gggaagtcaa gaa                                33

<210> SEQ ID NO 780
<211> LENGTH: 33
<212> TYPE: DNA
<213> ORGANISM: Homo Sapiens

<400> SEQUENCE: 780
tggcctataa gactatkagt gacttggcaa tgg                                33

<210> SEQ ID NO 781
<211> LENGTH: 33
<212> TYPE: DNA
<213> ORGANISM: Homo Sapiens

<400> SEQUENCE: 781
atatagtgtg tgcaaaygaa ataaggtaag aac  33

<210> SEQ ID NO 782
<211> LENGTH: 33
<212> TYPE: DNA
<213> ORGANISM: Homo Sapiens

<400> SEQUENCE: 782
aatgctgaaa gataatkaac atgaaagatg cca  33

<210> SEQ ID NO 783
<211> LENGTH: 33
<212> TYPE: DNA
<213> ORGANISM: Homo Sapiens

<400> SEQUENCE: 783
ttattgagga gtaaatraca caggtaaatt tgg  33

<210> SEQ ID NO 784
<211> LENGTH: 33
<212> TYPE: DNA
<213> ORGANISM: Homo Sapiens

<400> SEQUENCE: 784
gagtttataa gttgtaygta aacattcttg aac  33

<210> SEQ ID NO 785
<211> LENGTH: 33
<212> TYPE: DNA
<213> ORGANISM: Homo Sapiens

<400> SEQUENCE: 785
taataaccaa ttttccyatg tagcaaaccc gca  33

<210> SEQ ID NO 786
<211> LENGTH: 33
<212> TYPE: DNA
<213> ORGANISM: Homo Sapiens

<400> SEQUENCE: 786
tattttgcct gagagakgta acttacctct gtt  33

<210> SEQ ID NO 787
<211> LENGTH: 33
<212> TYPE: DNA
<213> ORGANISM: Homo Sapiens

<400> SEQUENCE: 787
cttttcttgg acccatraga gaattgatgt tgc  33

<210> SEQ ID NO 788
<211> LENGTH: 33
<212> TYPE: DNA
<213> ORGANISM: Homo Sapiens

<400> SEQUENCE: 788
catgctgtgt gaagtgkata tttaattggg gct  33

<210> SEQ ID NO 789
<211> LENGTH: 33
<212> TYPE: DNA
<213> ORGANISM: Homo Sapiens

<400> SEQUENCE: 789
ctctagagga tcagcaygga atttggccaa aac        33

<210> SEQ ID NO 790
<211> LENGTH: 33
<212> TYPE: DNA
<213> ORGANISM: Homo Sapiens

<400> SEQUENCE: 790
aaaaggccaa cagatcmgaa gatgtttgcc att        33

<210> SEQ ID NO 791
<211> LENGTH: 33
<212> TYPE: DNA
<213> ORGANISM: Homo Sapiens

<400> SEQUENCE: 791
aatgaacaga agcaaasagg ctatgatggg gac        33

<210> SEQ ID NO 792
<211> LENGTH: 33
<212> TYPE: DNA
<213> ORGANISM: Homo Sapiens

<400> SEQUENCE: 792
ccaagtaaat ccagaawgtt tgcaacagga ttt        33

<210> SEQ ID NO 793
<211> LENGTH: 33
<212> TYPE: DNA
<213> ORGANISM: Homo Sapiens

<400> SEQUENCE: 793
gaatttacag acaaaayatc atctttcctg ttc        33

<210> SEQ ID NO 794
<211> LENGTH: 33
<212> TYPE: DNA
<213> ORGANISM: Homo Sapiens

<400> SEQUENCE: 794
agagatgtta aacaccygca aaggaagta tgt         33

<210> SEQ ID NO 795
<211> LENGTH: 33
<212> TYPE: DNA
<213> ORGANISM: Homo Sapiens

<400> SEQUENCE: 795
ctgaacctct agagaayaca gtcaggtaga tga        33

<210> SEQ ID NO 796
<211> LENGTH: 33
<212> TYPE: DNA
<213> ORGANISM: Homo Sapiens

<400> SEQUENCE: 796
accttgctgt aaaaccrcat gaaattcata ttt        33

<210> SEQ ID NO 797
<211> LENGTH: 33
<212> TYPE: DNA

```
<213> ORGANISM: Homo Sapiens

<400> SEQUENCE: 797
acctaatgct atctaaygta ttctgttctt aga                          33

<210> SEQ ID NO 798
<211> LENGTH: 33
<212> TYPE: DNA
<213> ORGANISM: Homo Sapiens

<400> SEQUENCE: 798
ctgggcaatc tgcttcyaaa ggtaagaggt ggt                          33

<210> SEQ ID NO 799
<211> LENGTH: 33
<212> TYPE: DNA
<213> ORGANISM: Homo Sapiens

<400> SEQUENCE: 799
catggtgtct agaacgyatt atgtacttaa taa                          33

<210> SEQ ID NO 800
<211> LENGTH: 33
<212> TYPE: DNA
<213> ORGANISM: Homo Sapiens

<400> SEQUENCE: 800
aatgtttcat gtgaagragc actgctctaa aac                          33

<210> SEQ ID NO 801
<211> LENGTH: 33
<212> TYPE: DNA
<213> ORGANISM: Homo Sapiens

<400> SEQUENCE: 801
tatatgcaca cacatgragg tacccacaca cat                          33

<210> SEQ ID NO 802
<211> LENGTH: 33
<212> TYPE: DNA
<213> ORGANISM: Homo Sapiens

<400> SEQUENCE: 802
ttacttctga ataagcmaag ttaagctaca gtc                          33

<210> SEQ ID NO 803
<211> LENGTH: 33
<212> TYPE: DNA
<213> ORGANISM: Homo Sapiens

<400> SEQUENCE: 803
agaatattag agaagcsgac tagttgactg tag                          33

<210> SEQ ID NO 804
<211> LENGTH: 33
<212> TYPE: DNA
<213> ORGANISM: Homo Sapiens

<400> SEQUENCE: 804
aaaacaggaa ctacaayatt ctcacacagt cct                          33

<210> SEQ ID NO 805
<211> LENGTH: 33
```

<212> TYPE: DNA
<213> ORGANISM: Homo Sapiens

<400> SEQUENCE: 805
acttttgtgg attcaastga cataataaca tgc                              33

<210> SEQ ID NO 806
<211> LENGTH: 33
<212> TYPE: DNA
<213> ORGANISM: Homo Sapiens

<400> SEQUENCE: 806
tttggagcag gtcttamgtg aacattagaa aag                              33

<210> SEQ ID NO 807
<211> LENGTH: 33
<212> TYPE: DNA
<213> ORGANISM: Homo Sapiens

<400> SEQUENCE: 807
gaaatgaaag gatgacrctc accaacataa aag                              33

<210> SEQ ID NO 808
<211> LENGTH: 33
<212> TYPE: DNA
<213> ORGANISM: Homo Sapiens

<400> SEQUENCE: 808
atggaataca tttttcraag ttctaatccc tta                              33

<210> SEQ ID NO 809
<211> LENGTH: 33
<212> TYPE: DNA
<213> ORGANISM: Homo Sapiens

<400> SEQUENCE: 809
tatccccttc ctgccgmatg actaaaacta aat                              33

<210> SEQ ID NO 810
<211> LENGTH: 33
<212> TYPE: DNA
<213> ORGANISM: Homo Sapiens

<400> SEQUENCE: 810
tggaagtgac agaaccrgaa gggattggtg aga                              33

<210> SEQ ID NO 811
<211> LENGTH: 33
<212> TYPE: DNA
<213> ORGANISM: Homo Sapiens

<400> SEQUENCE: 811
attaattgag tagaacrcag tcaaagcatt gca                              33

<210> SEQ ID NO 812
<211> LENGTH: 33
<212> TYPE: DNA
<213> ORGANISM: Homo Sapiens

<400> SEQUENCE: 812
ggttactgat aataaaytga gactgggttt atg                              33

<210> SEQ ID NO 813

-continued

<210> SEQ ID NO 813
<211> LENGTH: 33
<212> TYPE: DNA
<213> ORGANISM: Homo Sapiens

<400> SEQUENCE: 813
tattgagtga tcattarcat ctcacatcct gcc                33

<210> SEQ ID NO 814
<211> LENGTH: 33
<212> TYPE: DNA
<213> ORGANISM: Homo Sapiens

<400> SEQUENCE: 814
caccagtttg cccccaytga atgtcggttt agc                33

<210> SEQ ID NO 815
<211> LENGTH: 33
<212> TYPE: DNA
<213> ORGANISM: Homo Sapiens

<400> SEQUENCE: 815
tgacatttgc attatcygag gggcacactg gtc                33

<210> SEQ ID NO 816
<211> LENGTH: 33
<212> TYPE: DNA
<213> ORGANISM: Homo Sapiens

<400> SEQUENCE: 816
atcaaaatgt gacataraga aacaaagtga gca                33

<210> SEQ ID NO 817
<211> LENGTH: 33
<212> TYPE: DNA
<213> ORGANISM: Homo Sapiens

<400> SEQUENCE: 817
gttttgttgg acatagratt ctcagtttag agt                33

<210> SEQ ID NO 818
<211> LENGTH: 33
<212> TYPE: DNA
<213> ORGANISM: Homo Sapiens

<400> SEQUENCE: 818
taagcaaaga gaaaaaytgt atttccagtc aca                33

<210> SEQ ID NO 819
<211> LENGTH: 33
<212> TYPE: DNA
<213> ORGANISM: Homo Sapiens

<400> SEQUENCE: 819
ctctgcgtcc acggaawttc caccaagtag ctg                33

<210> SEQ ID NO 820
<211> LENGTH: 33
<212> TYPE: DNA
<213> ORGANISM: Homo Sapiens

<400> SEQUENCE: 820
tggcagttat taaaccwgaa agtgaggtag tta                33

<210> SEQ ID NO 821
<211> LENGTH: 33
<212> TYPE: DNA
<213> ORGANISM: Homo Sapiens

<400> SEQUENCE: 821
cctggggcac cttgtcsagc aggaaggtga tca        33

<210> SEQ ID NO 822
<211> LENGTH: 33
<212> TYPE: DNA
<213> ORGANISM: Homo Sapiens

<400> SEQUENCE: 822
ttagatggat gccgaartgt ttaagggtaa aaa        33

<210> SEQ ID NO 823
<211> LENGTH: 33
<212> TYPE: DNA
<213> ORGANISM: Homo Sapiens

<400> SEQUENCE: 823
gactctgtga ctgcaawact tctaggctct ctg        33

<210> SEQ ID NO 824
<211> LENGTH: 33
<212> TYPE: DNA
<213> ORGANISM: Homo Sapiens

<400> SEQUENCE: 824
acaagactag aaatcargca gcctgggttc aag        33

<210> SEQ ID NO 825
<211> LENGTH: 33
<212> TYPE: DNA
<213> ORGANISM: Homo Sapiens

<400> SEQUENCE: 825
gctgtccatt gcttaaygca ggttatttca tta        33

<210> SEQ ID NO 826
<211> LENGTH: 33
<212> TYPE: DNA
<213> ORGANISM: Homo Sapiens

<400> SEQUENCE: 826
cttcacagag aatagaygtt cagcaaacaa cag        33

<210> SEQ ID NO 827
<211> LENGTH: 33
<212> TYPE: DNA
<213> ORGANISM: Homo Sapiens

<400> SEQUENCE: 827
ctttactcta tgtccayatt ggaaatgcac aaa        33

<210> SEQ ID NO 828
<211> LENGTH: 33
<212> TYPE: DNA
<213> ORGANISM: Homo Sapiens

<400> SEQUENCE: 828
ttcatgttga catttaraag acagaaagcc cat        33

<210> SEQ ID NO 829
<211> LENGTH: 33
<212> TYPE: DNA
<213> ORGANISM: Homo Sapiens

<400> SEQUENCE: 829
tcaagactct gtgccamcat tgggtttgtg ctc                33

<210> SEQ ID NO 830
<211> LENGTH: 33
<212> TYPE: DNA
<213> ORGANISM: Homo Sapiens

<400> SEQUENCE: 830
actctgacag tcatcaygtc tggttctaag atc                33

<210> SEQ ID NO 831
<211> LENGTH: 33
<212> TYPE: DNA
<213> ORGANISM: Homo Sapiens

<400> SEQUENCE: 831
catatcataa agacaamcct gctaattctt ctc                33

<210> SEQ ID NO 832
<211> LENGTH: 33
<212> TYPE: DNA
<213> ORGANISM: Homo Sapiens

<400> SEQUENCE: 832
attattttta agcaaaytgt attcctcata tcc                33

<210> SEQ ID NO 833
<211> LENGTH: 33
<212> TYPE: DNA
<213> ORGANISM: Homo Sapiens

<400> SEQUENCE: 833
ttcttccatt gaaatcraac agccaaattc cac                33

<210> SEQ ID NO 834
<211> LENGTH: 33
<212> TYPE: DNA
<213> ORGANISM: Homo Sapiens

<400> SEQUENCE: 834
gagacataga aataatraaa gcattgtgaa att                33

<210> SEQ ID NO 835
<211> LENGTH: 33
<212> TYPE: DNA
<213> ORGANISM: Homo Sapiens

<400> SEQUENCE: 835
catagaatat ggcaaaytgg acaagtgctt cac                33

<210> SEQ ID NO 836
<211> LENGTH: 33
<212> TYPE: DNA
<213> ORGANISM: Homo Sapiens

<400> SEQUENCE: 836
cattagtgag gcgtcayact gattctggag gcg                33

<210> SEQ ID NO 837
<211> LENGTH: 33
<212> TYPE: DNA
<213> ORGANISM: Homo Sapiens

<400> SEQUENCE: 837
ctatttaaga cagcaarcgt acattaagac taa                        33

<210> SEQ ID NO 838
<211> LENGTH: 33
<212> TYPE: DNA
<213> ORGANISM: Homo Sapiens

<400> SEQUENCE: 838
tcaatttcta gaactgyaat agtgtccatg gaa                        33

<210> SEQ ID NO 839
<211> LENGTH: 33
<212> TYPE: DNA
<213> ORGANISM: Homo Sapiens

<400> SEQUENCE: 839
ctccccaaag ccaccamtat caatacatgc acc                        33

<210> SEQ ID NO 840
<211> LENGTH: 33
<212> TYPE: DNA
<213> ORGANISM: Homo Sapiens

<400> SEQUENCE: 840
tctagcatcc atttcasaaa ccatacaaga ctc                        33

<210> SEQ ID NO 841
<211> LENGTH: 33
<212> TYPE: DNA
<213> ORGANISM: Homo Sapiens

<400> SEQUENCE: 841
actcattcaa gttatckctt ctagcatcca ttt                        33

<210> SEQ ID NO 842
<211> LENGTH: 33
<212> TYPE: DNA
<213> ORGANISM: Homo Sapiens

<400> SEQUENCE: 842
aaggggcagt tccatayagt aggtgacaca ggt                        33

<210> SEQ ID NO 843
<211> LENGTH: 33
<212> TYPE: DNA
<213> ORGANISM: Homo Sapiens

<400> SEQUENCE: 843
gcagactcca gacaaayaca gctggttatg cac                        33

<210> SEQ ID NO 844
<211> LENGTH: 33
<212> TYPE: DNA
<213> ORGANISM: Homo Sapiens

<400> SEQUENCE: 844

-continued

```
gttatgtgaa aaagcasaac cctctaattt gtt                               33

<210> SEQ ID NO 845
<211> LENGTH: 33
<212> TYPE: DNA
<213> ORGANISM: Homo Sapiens

<400> SEQUENCE: 845
aggcaatgac ttccacsagg aatacacgtc att                               33

<210> SEQ ID NO 846
<211> LENGTH: 33
<212> TYPE: DNA
<213> ORGANISM: Homo Sapiens

<400> SEQUENCE: 846
cgcacagctg aaatgayggg tttcactgca ggg                               33

<210> SEQ ID NO 847
<211> LENGTH: 33
<212> TYPE: DNA
<213> ORGANISM: Homo Sapiens

<400> SEQUENCE: 847
acaaaaaggc taagcayaat gacggactaa gat                               33

<210> SEQ ID NO 848
<211> LENGTH: 33
<212> TYPE: DNA
<213> ORGANISM: Homo Sapiens

<400> SEQUENCE: 848
cagcagatta aacacaytga gcccactgga agc                               33

<210> SEQ ID NO 849
<211> LENGTH: 33
<212> TYPE: DNA
<213> ORGANISM: Homo Sapiens

<400> SEQUENCE: 849
ctttgggact tgccawaga gactagaaga tgt                                33

<210> SEQ ID NO 850
<211> LENGTH: 33
<212> TYPE: DNA
<213> ORGANISM: Homo Sapiens

<400> SEQUENCE: 850
gttaaatgac tcaccarggg caaaggtaca gat                               33

<210> SEQ ID NO 851
<211> LENGTH: 33
<212> TYPE: DNA
<213> ORGANISM: Homo Sapiens

<400> SEQUENCE: 851
ggctaagggt tggtgcrcag aaagcactta gca                               33

<210> SEQ ID NO 852
<211> LENGTH: 33
<212> TYPE: DNA
<213> ORGANISM: Homo Sapiens

<400> SEQUENCE: 852
```
tcaatctgca aatgagyatc ttcagcccct agc                33

<210> SEQ ID NO 853
<211> LENGTH: 33
<212> TYPE: DNA
<213> ORGANISM: Homo Sapiens

<400> SEQUENCE: 853
tctgtaaaag cacttaygat tttgcaccct gct                33

<210> SEQ ID NO 854
<211> LENGTH: 33
<212> TYPE: DNA
<213> ORGANISM: Homo Sapiens

<400> SEQUENCE: 854
gcaccctgct tcatgaygga tctgcactgg ttt                33

<210> SEQ ID NO 855
<211> LENGTH: 33
<212> TYPE: DNA
<213> ORGANISM: Homo Sapiens

<400> SEQUENCE: 855
catccaaaag cagtgasatg accattcaag agc                33

<210> SEQ ID NO 856
<211> LENGTH: 33
<212> TYPE: DNA
<213> ORGANISM: Homo Sapiens

<400> SEQUENCE: 856
aaggaggttg gtaggartag ctttcagctg ttg                33

<210> SEQ ID NO 857
<211> LENGTH: 33
<212> TYPE: DNA
<213> ORGANISM: Homo Sapiens

<400> SEQUENCE: 857
tctttcttca agcacayata gatacttcct aga                33

<210> SEQ ID NO 858
<211> LENGTH: 33
<212> TYPE: DNA
<213> ORGANISM: Homo Sapiens

<400> SEQUENCE: 858
ttggtttact gagaaaygca aaagcctggg aaa                33

<210> SEQ ID NO 859
<211> LENGTH: 33
<212> TYPE: DNA
<213> ORGANISM: Homo Sapiens

<400> SEQUENCE: 859
ccccatatct tgacagwctg atgtattttt ctt                33

<210> SEQ ID NO 860
<211> LENGTH: 33
<212> TYPE: DNA
<213> ORGANISM: Homo Sapiens

```
<400> SEQUENCE: 860
gcccacttac ttacagmaac atagacagct ttc                                33

<210> SEQ ID NO 861
<211> LENGTH: 33
<212> TYPE: DNA
<213> ORGANISM: Homo Sapiens

<400> SEQUENCE: 861
gttaaccatc tgccacyaaa ctgttgctgc att                                33

<210> SEQ ID NO 862
<211> LENGTH: 33
<212> TYPE: DNA
<213> ORGANISM: Homo Sapiens

<400> SEQUENCE: 862
cccagtccca ccttagragt gtagaacagc gtc                                33

<210> SEQ ID NO 863
<211> LENGTH: 33
<212> TYPE: DNA
<213> ORGANISM: Homo Sapiens

<400> SEQUENCE: 863
ttatctgctc actgcaygag ttttgccact cac                                33

<210> SEQ ID NO 864
<211> LENGTH: 33
<212> TYPE: DNA
<213> ORGANISM: Homo Sapiens

<400> SEQUENCE: 864
caatgctcaa gctttcycag tgcttctcaa act                                33

<210> SEQ ID NO 865
<211> LENGTH: 33
<212> TYPE: DNA
<213> ORGANISM: Homo Sapiens

<400> SEQUENCE: 865
ctgaacccgg atcaackgaa gcttcagtga gtt                                33

<210> SEQ ID NO 866
<211> LENGTH: 33
<212> TYPE: DNA
<213> ORGANISM: Homo Sapiens

<400> SEQUENCE: 866
atgccttggt tcgggckctt cctgagactc tca                                33

<210> SEQ ID NO 867
<211> LENGTH: 33
<212> TYPE: DNA
<213> ORGANISM: Homo Sapiens

<400> SEQUENCE: 867
gacctacagc agaaacrctt actttgttca aca                                33

<210> SEQ ID NO 868
<211> LENGTH: 33
<212> TYPE: DNA
<213> ORGANISM: Homo Sapiens
```

```
<400> SEQUENCE: 868
gctgatccct gatagcrcag cttcacagag cac                              33

<210> SEQ ID NO 869
<211> LENGTH: 33
<212> TYPE: DNA
<213> ORGANISM: Homo Sapiens

<400> SEQUENCE: 869
cataactgtt tcagccratt cacatctata cat                              33

<210> SEQ ID NO 870
<211> LENGTH: 33
<212> TYPE: DNA
<213> ORGANISM: Homo Sapiens

<400> SEQUENCE: 870
gaataggcag cgtgaayggt attaaattta tga                              33

<210> SEQ ID NO 871
<211> LENGTH: 33
<212> TYPE: DNA
<213> ORGANISM: Homo Sapiens

<400> SEQUENCE: 871
gtagggcccc tcaggamgtg tagctgccct gcc                              33

<210> SEQ ID NO 872
<211> LENGTH: 33
<212> TYPE: DNA
<213> ORGANISM: Homo Sapiens

<400> SEQUENCE: 872
tgtatgttga gtctgartac acaagtcaca atc                              33

<210> SEQ ID NO 873
<211> LENGTH: 33
<212> TYPE: DNA
<213> ORGANISM: Homo Sapiens

<400> SEQUENCE: 873
acctgaccat cacagaygac tgtgacacaa tca                              33

<210> SEQ ID NO 874
<211> LENGTH: 33
<212> TYPE: DNA
<213> ORGANISM: Homo Sapiens

<400> SEQUENCE: 874
ctataattaa gacggawatc tttaataggc cat                              33

<210> SEQ ID NO 875
<211> LENGTH: 33
<212> TYPE: DNA
<213> ORGANISM: Homo Sapiens

<400> SEQUENCE: 875
gcctttctgc ctgtacract ccagtgtgta cct                              33

<210> SEQ ID NO 876
<211> LENGTH: 33
<212> TYPE: DNA
```

<213> ORGANISM: Homo Sapiens

<400> SEQUENCE: 876
gggaatgtga ggtagcyatc cagtgatgtt taa        33

<210> SEQ ID NO 877
<211> LENGTH: 33
<212> TYPE: DNA
<213> ORGANISM: Homo Sapiens

<400> SEQUENCE: 877
ctgatgctgc cagttckgaa actacatttt gag        33

<210> SEQ ID NO 878
<211> LENGTH: 33
<212> TYPE: DNA
<213> ORGANISM: Homo Sapiens

<400> SEQUENCE: 878
actctcatta tgacgargag taaatttcca tca        33

<210> SEQ ID NO 879
<211> LENGTH: 33
<212> TYPE: DNA
<213> ORGANISM: Homo Sapiens

<400> SEQUENCE: 879
ctctgccgaa gacacasaaa aaagaaattc aac        33

<210> SEQ ID NO 880
<211> LENGTH: 33
<212> TYPE: DNA
<213> ORGANISM: Homo Sapiens

<400> SEQUENCE: 880
catcattgaa ataaacyggg gatccatttc agc        33

<210> SEQ ID NO 881
<211> LENGTH: 33
<212> TYPE: DNA
<213> ORGANISM: Homo Sapiens

<400> SEQUENCE: 881
ggccaggcca agcaagsagc gtggactcca gac        33

<210> SEQ ID NO 882
<211> LENGTH: 33
<212> TYPE: DNA
<213> ORGANISM: Homo Sapiens

<400> SEQUENCE: 882
gcgggcaggg gcttgcrgaa tcgctacctt ctt        33

<210> SEQ ID NO 883
<211> LENGTH: 33
<212> TYPE: DNA
<213> ORGANISM: Homo Sapiens

<400> SEQUENCE: 883
ggcttcttaa caccggmcat tcctgagtct ctg        33

<210> SEQ ID NO 884
<211> LENGTH: 33

```
<212> TYPE: DNA
<213> ORGANISM: Homo Sapiens

<400> SEQUENCE: 884
gtgggaaaat cttgagsatc ttctcctggg ctc                                   33

<210> SEQ ID NO 885
<211> LENGTH: 33
<212> TYPE: DNA
<213> ORGANISM: Homo Sapiens

<400> SEQUENCE: 885
ccgcagcttc cgtcccrcca agcgcccatg gag                                   33

<210> SEQ ID NO 886
<211> LENGTH: 33
<212> TYPE: DNA
<213> ORGANISM: Homo Sapiens

<400> SEQUENCE: 886
gccacatggc ctcaacrgtc caagtcagga tgg                                   33

<210> SEQ ID NO 887
<211> LENGTH: 33
<212> TYPE: DNA
<213> ORGANISM: Homo Sapiens

<400> SEQUENCE: 887
actaaaatat gcaacaraac atgaaaaagg tac                                   33

<210> SEQ ID NO 888
<211> LENGTH: 33
<212> TYPE: DNA
<213> ORGANISM: Homo Sapiens

<400> SEQUENCE: 888
ttactgttgg tcaaaayttt gtacagtatc tca                                   33

<210> SEQ ID NO 889
<211> LENGTH: 33
<212> TYPE: DNA
<213> ORGANISM: Homo Sapiens

<400> SEQUENCE: 889
tcaggcttct ttctccscat gtcatgtttg tga                                   33

<210> SEQ ID NO 890
<211> LENGTH: 33
<212> TYPE: DNA
<213> ORGANISM: Homo Sapiens

<400> SEQUENCE: 890
aacccaagtt aatgacrcac cttttcttgt gtg                                   33

<210> SEQ ID NO 891
<211> LENGTH: 33
<212> TYPE: DNA
<213> ORGANISM: Homo Sapiens

<400> SEQUENCE: 891
tgctgcatga gggaacyaat acagtttcta ata                                   33

<210> SEQ ID NO 892
```

```
<211> LENGTH: 33
<212> TYPE: DNA
<213> ORGANISM: Homo Sapiens

<400> SEQUENCE: 892
gcttgcttct gagaaawtcc agtctaagag agc                                 33

<210> SEQ ID NO 893
<211> LENGTH: 33
<212> TYPE: DNA
<213> ORGANISM: Homo Sapiens

<400> SEQUENCE: 893
ttggcaaaaa ggcctasaga gtgatacact tga                                 33

<210> SEQ ID NO 894
<211> LENGTH: 33
<212> TYPE: DNA
<213> ORGANISM: Homo Sapiens

<400> SEQUENCE: 894
gtctattgcc ctcaaartgt tctcaacagg aaa                                 33

<210> SEQ ID NO 895
<211> LENGTH: 33
<212> TYPE: DNA
<213> ORGANISM: Homo Sapiens

<400> SEQUENCE: 895
gagcagaggg tagaacrgtg agagataaag aag                                 33

<210> SEQ ID NO 896
<211> LENGTH: 33
<212> TYPE: DNA
<213> ORGANISM: Homo Sapiens

<400> SEQUENCE: 896
ccctgaggca cctctamaga aactcaagaa cag                                 33

<210> SEQ ID NO 897
<211> LENGTH: 33
<212> TYPE: DNA
<213> ORGANISM: Homo Sapiens

<400> SEQUENCE: 897
tgctgttccc ttatgcrcca cagcttctac atc                                 33

<210> SEQ ID NO 898
<211> LENGTH: 33
<212> TYPE: DNA
<213> ORGANISM: Homo Sapiens

<400> SEQUENCE: 898
ttgtcatagg tattcarggg tacattcacc aga                                 33
```

GENETIC MARKERS ASSOCIATED WITH ENDOMETRIOSIS AND USE THEREOF

CROSS REFERENCE TO RELATED APPLICATIONS

This nonprovisional utility patent application claims the benefit under 35 U.S.C. § 119(e) of U.S. provisional application No. 61/171,717, filed Apr. 22, 2009 and U.S. provisional application No. 61/245,808, filed Sep. 25, 2009, all of which are incorporated herein in their entirety by this reference.

FIELD OF THE INVENTION

The present invention relates to endometriosis diagnosis and therapy. In particular, the present invention relates to specific single nucleotide polymorphisms (SNPs) in the human genome, and their association with endometriosis and related pathologies.

BACKGROUND OF THE INVENTION

Endometriosis in one instance refers to autoimmune endometriosis, mild endometriosis, moderate endometriosis or severe endometriosis. For the purpose of this invention the term endometriosis is used to describe any of these conditions.

Endometriosis is most generally defined as the presence of endometrium (glands and stroma) at sites outside of the uterus (ectopic endometrial tissues rather than eutopic or within the uterus). The most common sites are the ovaries, pelvic peritoneum, uterosacral ligaments, pouch of Douglas, and rectovaginal septum although implants have been identified on the peritoneal surfaces of the abdomen (these may grow into the intestines, ureters or bladder), in the thorax, at the umbilicus, and at incision sites of prior surgeries (Child T J, Tan S L (2001) Endometriosis: aetiology, pathogenesis and treatment. Drugs 61:1735-1750; Giudice et al. (1998) Status of current research on endometriosis. The Journal of reproductive medicine 43:252-262).

Endometriosis is a common gynecologic disorder. The prevalence is difficult to know. It has been estimated that it affects approximately 14% of all women (range 1-43%), 40-60% of women with pelvic pain and 30%-50% of infertile women (Di Blasio et al. (2005) Genetics of endometriosis. Minerva ginecologica 57:225-236; Schindler A E (2004) Pathophysiology, diagnosis and treatment of endometriosis. Minerva ginecologica 56:419-435).

Studies of the inheritance of endometriosis have been hampered by methodological problems related to disease definition and control selection. General population incidence during the 1970s in this country has been suggested to be 1.6 per 1000 white females aged 15-49, while a more current study based upon hospital discharges finds endometriosis as a first listed diagnosis in 1.3 per 1000 discharges in women aged 15-44. There is a clinical impression that blacks have lower rates of endometriosis and Orientals have higher rates than whites. Separate work has suggested a polygenic/multifactorial inheritance (Vigano P, Somigliana E, Vignali M, Busacca M, Blasio A M (2007) Genetics of endometriosis: current status and prospects. Front Biosci 12:3247-3255). Affected sib-pair studies have also performed (Kennedy et al. (2001) Affected sib-pair analysis in endometriosis. Human reproduction update 7:411-418; Treloar et al. (2005) Genomewide linkage study in 1,176 affected sister pair families identifies a significant susceptibility locus for endometriosis on chromosome 10q26. Am J Hum Genet 77:365-376).

Specific genes with polymorphisms have been investigated for an association with endometriosis. Some association studies implicated GALT (a gene involved in galactose metabolism), and GSTM1 and NAT2 (genes encoding for the detoxification enzymes) as possible disease susceptibility genes. Recent findings have added to the evidence for the involvement of GSTM1 and NAT2, but have cast doubt on the role of GALT. The CDKN1A gene codon 31 arginine/serine polymorphism is not associated with endometriosis.

Polymorphisms of the arylhydrocarbon receptor (AHR) gene and related genes were examined, and in at least one study, no association was found. However, the design of many genetic and epidemiological studies has been inadequate with respect to sample size, consistency in phenotype definition, and the choice of control populations. To identify genomic changes involved in the development of endometriosis (Gogusev et al. (1999). "Detection of DNA copy number changes in human endometriosis by comparative genomic hybridization." Hum Genet 105(5): 444-51) examined endometriotic tissues by comparative genomic hybridization and detected losses of 1p and 22q in 50% of the cases. Additional common losses included 7p (22%). Dual-color FISH using probes for the deleted regions on chromosomes 1, 7, and 22 supported the CGH data. Treloar et al. (Treloar et al. (2005). "Genomewide linkage study in 1,176 affected sister pair families identifies a significant susceptibility locus for endometriosis on chromosome 10q26." Am J Hum Genet 77(3): 365-76) conducted a linkage study of 1,176 families (931 Australian and 245 from the U.K.), each with at least 2 affected family members, usually affected sister pairs, with surgically diagnosed disease. They identified a region of significant linkage on 10q26 (maximum lod score=3.09; genomewide P=0.047) and another region of suggestive linkage on 20p13; minor peaks were found on 8 other chromosomes.

Endometriosis is a genetically inherited disease. Genetic variation in DNA sequences is often associated with heritable phenotypes, such as an individual's propensity towards complex disorders. Single nucleotide polymorphisms are the most common form of genetic sequence variations. Detection and analysis of specific genetic mutations, such as single nucleotide polymorphisms (SNPs), which are associated with endometriosis risk, may therefore be used to determine risk of endometriosis, the presence of endometriosis or the progression of endometriosis. Genetic markers that are prognostic for endometriosis can be genotyped early in life and could predict individual response to various risk factors and treatment. Genetic predisposition revealed by genetic analysis of susceptibility genes can provide an integrated assessment of the interaction between genotypes and environmental factors, resulting in synergistically increased prognostic value of diagnostic tests. Thus, presymptomatic and early symptomatic genetic testing is expected to be the cornerstone of the paradigmatic shift from late surgical interventions to earlier preventative therapies.

Thus, there is an urgent need for novel genetic markers that are predictive of endometriosis and endometriosis progression, particularly in treatment decisions for individuals who are recognized as having endometriosis. Such genetic markers may enable prognosis of endometriosis in much larger populations compared with the populations which can currently be evaluated by using existing risk factors and biomarkers. The availability of a genetic test may allow, for example, early diagnosis and prognosis of endometriosis, as well as early clinical intervention to mitigate progression of the disease. The use of these genetic markers will also allow selection of subjects for clinical trials involving novel treatment methods. The discovery of genetic markers associated with endometriosis will further provide novel targets for therapeutic intervention or preventive treatments of endometriosis and enable the development of new therapeutic agents for treating endometriosis.

SUMMARY OF THE INVENTION

The present invention relates to the identification of novel SNPs, unique combinations of such SNPs, and haplotypes of SNPs that are associated with endometriosis and related pathologies. The polymorphisms disclosed herein are directly useful as targets for the design of diagnostic reagents and the development of therapeutic agents for use in the diagnosis and treatment of endometriosis and related pathologies.

Based on the identification of SNPs associated with endometriosis, the present invention also provides methods of detecting these variants as well as the design and preparation of detection reagents needed to accomplish this task. The invention specifically provides novel SNPs in genetic sequences involved in endometriosis, methods of detecting these SNPs in a test sample, methods of identifying individuals who have an altered risk of developing endometriosis and for suggesting treatment options for endometriosis based on the presence of a SNP(s) disclosed herein or its encoded product and methods of identifying individuals who are more or less likely to respond to a treatment.

In one embodiment of the invention, the present invention provides SNPs, as set forth in Table 1 having significant allelic association with endometriosis or by being co-located within the same LD blocks as the SNPs listed in Tables 1, and such as set forth in Tables 2-528. Tables 2-528 provide information identifying SNPs of the present invention, including SNP "rs" identification numbers (a reference SNP or RefSNP accession ID number) or "SNP-A" identification numbers (a reference SNP or RefSNP accession ID number), chromosome number, and base position number of the SNP.

In a specific embodiment of the present invention, naturally-occurring SNPs in the human genome are provided that are associated with endometriosis. Such SNPs can have a variety of uses in the diagnosis and/or treatment of endometriosis. One aspect of the present invention relates to an isolated nucleic acid molecule comprising a nucleotide sequence in which at least one nucleotide is a SNP disclosed in Table 1. In an alternative embodiment, a nucleic acid of the invention is an amplified polynucleotide, which is produced by amplification of a SNP-containing nucleic acid template.

In yet another embodiment of the invention, a reagent for detecting a SNP in the context of its naturally-occurring flanking nucleotide sequences (which can be, e.g., either DNA or mRNA) is provided. In particular, such a reagent may be in the form of, for example, a hybridization probe or an amplification primer that is useful in the specific detection of a SNP of interest.

Also provided in the invention are kits comprising SNP detection reagents and methods for detecting the SNPs disclosed herein by employing detection reagents. In a specific embodiment, the present invention provides for a method of identifying an individual having an increased or decreased risk of developing endometriosis by detecting the presence or absence of a SNP allele disclosed herein. In another embodiment, a method for diagnosis of endometriosis by detecting the presence or absence of a SNP allele disclosed herein is provided. In yet another embodiment a method for predicting endometriosis sub-classification by detecting the presence or absence of a SNP allele disclosed herein is provided.

In yet another embodiment, the invention also provides a kit comprising SNP detection reagents, and methods for detecting the SNPs disclosed herein by employing detection reagents and a questionnaire of non-genetic clinical factors. In one embodiment, the questionnaire would be completed by a medical professional based on medical history physical exam or other clinical findings. In yet another embodiment, the questionnaire would include any other non-genetic clinical factors known to be associated with the risk of developing endometriosis.

Many other uses and advantages of the present invention will be apparent to those skilled in the art upon review of the detailed description of the preferred embodiments herein. Solely for clarity of discussion, the invention is described in the sections below by way of non-limiting examples.

DETAILED DESCRIPTION OF THE INVENTION

Definitions

The term "haplotype" means a combination of genotypes on the same chromosome occurring in a linkage disequilibrium block. Haplotypes serve as markers for linkage disequilibrium blocks, and at the same time provide information about the arrangement of genotypes within the blocks. Typing of only certain SNPs which serve as tags can, therefore, with a high level of precision reveal all genotypes for SNPs located within a block. Thus, the use of haplotypes greatly facilitates identification of candidate genes associated with diseases and drug sensitivity.

The term "linkage disequilibrium" or "LD" means that a particular combination of alleles (alternative nucleotides) or genetic markers at two or more different SNP sites within a given chromosomal region are non-randomly co-inherited, meaning that the combination of alleles at the different SNP sites occurs more or less frequently in a population than the separate frequencies of occurrence of each allele or the frequency of a random formation of haplotypes from alleles in a given population. "LD" differs from "linkage," which describes the association of two or more loci on a chromosome with limited recombination between them. LD is also used to refer to any non-random genetic association between allele(s) at two or more different SNP sites. Therefore, when a SNP is in LD with other SNPs, the particular allele of the first SNP often predicts which alleles will be present in those SNPs in LD. LD is generally due to the physical proximity of the two loci along a chromosome. Hence, genotyping one of the SNP sites will give almost the same information as genotyping the other SNP site that is in LD. LD is caused by fitness interactions between genes or by such non-adaptive processes as population structure, inbreeding, and stochastic effects.

Various degrees of LD can be encountered between two or more SNPs with the result being that some SNPs are more closely associated (i.e., in stronger LD) than others. Furthermore, the physical distance over which LD extends along a chromosome differs between different regions of the genome, and therefore the degree of physical separation between two or more SNP sites necessary for LD to occur can differ between different regions of the genome. The average LD block size in Caucasians has been estimated to 16.3 kb occasionally extending across several hundred kb. LD blocks may also vary in size between ethnic groups (The International HapMap Consortium. A haplotype map of the human genome. Nature. Oct. 27 2005; 437(7063):1299-1320). Conservatively, LD can be defined as SNPs that have a D prime value of 1 and a LOD score greater than 2.0 or an r-squared value greater than 0.8.

"Linkage disequilibrium block" or "LD block" means a region of the genome that contains multiple SNPs located in proximity to each other and that are transmitted as a block.

"D prime" or "D'" (also referred to as the "linkage disequilibrium measure" or "linkage disequilibrium parameter") means the deviation of the observed allele frequencies from the expected, and is a statistical measure of how well a biometric system can discriminate between different individuals. The larger the D' value, the better a biometric system is at discriminating between individuals.

"LOD score" is the "logarithm of the odd" score, which is a statistical estimate of whether two genetic loci are physically near enough to each other (or "linked") on a particular chromosome that they are likely to be inherited together. A LOD score of three or more is generally considered statistically significant evidence of linkage.

"R-squared" or "$r^2$" (also referred to as the "correlation coefficient") is a statistical measure of the degree to which two markers are related. The nearer to 1.0 the $r^2$ value is, the more closely the markers are related to each other. $R^2$ cannot exceed 1.0. D prime and LOD scores generally follow the above definition for SNPs in LD. $R^2$, however, displays a more complex pattern and can vary between about 0.0003 and 1.0 in SNPs that are in LD.

The present invention provides SNPs associated with endometriosis, nucleic acid molecules containing SNPs, methods and reagents for the detection of the SNPs disclosed herein, uses of these SNPs for the development of detection reagents, and assays or kits that utilize such reagents. The SNPs disclosed herein are useful for diagnosing, screening for, and evaluating predisposition to endometriosis and progression of endometriosis. Additionally, such SNPs are useful in the determining individual subject treatment plans and design of clinical trials of devices for possible use in the treatment of endometriosis. Furthermore, such SNPs and their encoded products are useful targets for the development of therapeutic agents. Furthermore, such SNPs combined with other non-genetic clinical factors are useful for diagnosing, screening, evaluating predisposition to endometriosis, assessing risk of progression of endometriosis, determining individual subject treatment plans and design of clinical trials of devices for possible use in the treatment of endometriosis.

SNPs

As used herein, the term "SNP" refers to single nucleotide polymorphisms in DNA. SNPs are usually preceded and followed by highly conserved sequences that vary in less than 1/100 or 1/1000 members of the population. An individual may be homozygous or heterozygous for an allele at each SNP position. A SNP may, in some instances, be referred to as a "cSNP" to denote that the nucleotide sequence containing the SNP is an amino acid "coding" sequence.

A SNP may arise from a substitution of one nucleotide for another at the polymorphic site. Substitutions can be transitions or transversions. A transition is the replacement of one purine nucleotide by another purine nucleotide, or one pyrimidine by another pyrimidine. A transversion is the replacement of a purine by a pyrimidine, or vice versa. A SNP may also be a single base insertion or deletion variant referred to as an "indel".

A synonymous codon change, or silent mutation SNP (terms such as "SNP," "polymorphism," "mutation," "mutant," "variation," and "variant" are used herein interchangeably), is one that does not result in a change of amino acid due to the degeneracy of the genetic code. A substitution that changes a codon coding for one amino acid to a codon coding for a different amino acid (i.e., a non-synonymous codon change) is referred to as a missense mutation. A nonsense mutation results in a type of non-synonymous codon change in which a stop codon is formed, thereby leading to premature termination of a polypeptide chain and a truncated protein. A read-through mutation is another type of non-synonymous codon change that causes the destruction of a stop codon, thereby resulting in an extended polypeptide product. An indel that occur in a coding DNA segment gives rise to a frameshift mutation. While SNPs can be bi-, tri-, or tetra-allelic, the vast majority of the SNPs are bi-allelic, and are thus often referred to as "bi-allelic markers," or "di-allelic markers".

As used herein, references to SNPs and SNP genotypes include individual SNPs and/or haplotypes, which are groups of SNPs that are generally inherited together. Haplotypes can have stronger correlations with diseases or other phenotypic effects compared with individual SNPs, and therefore may provide increased diagnostic accuracy in some cases.

Causative SNPs are those SNPs that produce alterations in gene expression or in the structure and/or function of a gene product, and therefore are predictive of a possible clinical phenotype. One such class includes SNPs falling within regions of genes encoding a polypeptide product, i.e. cSNPs. These SNPs may result in an alteration of the amino acid sequence of the polypeptide product (i.e., non-synonymous codon changes) and give rise to the expression of a defective or other variant protein. Furthermore, in the case of nonsense mutations, a SNP may lead to premature termination of a polypeptide product. Such variant products can result in a pathological condition, e.g., genetic endometriosis.

Causative SNPs do not necessarily have to occur in coding regions; causative SNPs can occur in, for example, any genetic region that can ultimately affect the expression, structure, and/or activity of the protein encoded by a nucleic acid. Such genetic regions include, for example, those involved in transcription, such as SNPs in transcription factor binding domains, SNPs in promoter regions, in areas involved in transcript processing, such as SNPs at intron-exon boundaries that may cause defective splicing, or SNPs in mRNA processing signal sequences such as polyadenylation signal regions and miRNA recognition sites. Some SNPs that are not causative SNPs nevertheless are in close association with, and therefore segregate with, a disease-causing sequence. In this situation, the presence of a SNP correlates with the presence of, or predisposition to, or an increased risk in developing the endometriosis. These SNPs, although not causative, are nonetheless also useful for diagnostics, endometriosis predisposition screening, endometriosis progression risk and other uses.

Methods

An association study of a SNP and a specific disorder involves determining the presence or frequency of the SNP allele in biological samples from individuals with the disorder of interest, such as endometriosis, and comparing the information to that of controls (i.e., individuals who do not have the disorder; controls may be also referred to as "healthy" or "normal" individuals) who are preferably of similar age and race. The appropriate selection of patients and controls is important to the success of SNP association studies. Therefore, a pool of individuals with well-characterized phenotypes is extremely desirable.

A SNP may be screened in tissue samples or any biological sample obtained from an affected individual, and compared to control samples, and selected for its increased (or decreased) occurrence in a specific pathological condition, such as pathologies related to endometriosis. Once a statistically significant association is established between one or more SNP(s) and a pathological condition (or other phenotype) of interest, then the region around the SNP can optionally be thoroughly screened to identify the causative genetic locus/sequence(s) (e.g., causative SNP/mutation, gene, regulatory region, etc.) that influences the pathological condition or phenotype. Association studies may be conducted within the general population and are not limited to studies performed on related individuals in affected families (linkage studies). For diagnostic and prognostic purposes, if a particular SNP site is found to be useful for diagnosing a disease, such as endometriosis, other SNP sites which are in LD with this SNP site would also be expected to be useful for diagnosing the condition. Linkage disequilibrium is described in the human genome as blocks of SNPs along a chromosome segment that do not segregate independently (i.e., that are non-randomly co-inherited). The starting (5' end) and ending (3' end) of these blocks can vary depending on the criteria used for linkage disequilibrium in a given database, such as the value of D' or $r^2$ used to determine linkage disequilibrium.

Table 1 discloses SNPs that have been shown in case-control studies to be associated with endometriosis. Table 1 specifically shows SNPs from the Affymetrix 6.0 GeneChip that all showed significant association with endometriosis and identifying information regarding each SNP in columns labeled "Name" (the NCBI reference SNP identifier, "Chr" (the Chromosome where the SNP is located; note that the chromosome numbered "23" is used interchangeably for chromosome "X"), "Position" (the basepair position on the chromosome indicated), "P-Value" (the "Trend" p-value calculated by PLINK), "OR" (the Odds Ratio for the SNP in question), "F_A" (the minor allele frequency observed in the endometriosis affected cases), "F_U" (the minor allele frequency observed in the control individuals), MA (the Minor Allele of the two allelic variants observed for the SNP), and "FlankSequence" (the DNA sequence surrounding the SNP in question). The two allelic variants observed for the SNP are indicated in square brackets in the middle of the sequence.

Tables 2-528 define the linkage disequilibrium blocks surrounding each of the SNPs identified in Table 1. The linkage disequilibrium blocks were ascertained based upon the criteria set forth by the Haploview (ver. 4.1) computer algorithm under default settings using the HapMap dataset release 22 (Barrett J C et al. "Haploview: analysis and visualization of LD and haplotype maps." Bioinformatics, vol. 21, pp 263-265, 2005). It is noted however, that there may be other SNPs located in the regions covered by the LD blocks but not specifically listed in the LD block tables herein that due to their being located in the same region as SNPs in the LD blocks, have an association with endometriosis and are likewise valuable in determining predisposition to endometriosis.

Each of Tables 2-528 is prefaced by one or more SNPs from Table 1, and includes a list of one or more SNPs that correspond to a linkage disequilibrium block, including the SNPs from Table 1, which are highlighted in bold character within the table. Occasionally, an original SNP marker may not itself be present in the Hapmap SNP list but its presence is inferred based on its chromosomal location and basepair position. Also indicated in the tables is the chromosome, physical position in basepairs, minor allele frequency and observed alleles for each SNP. On rare occasions, a SNP falls outside of a linkage disequilibrium block, in which case no LD block is presented.

The SNPs shown in Tables 1-528 may be useful individually, in combination with one of the other SNPs or in a haplotype involving one of the other SNPs in Tables 1-528. Linkage disequilibrium blocks can be determined from genomewide genetic population studies which results are accessible in private and public databases, and can be visualized or tabularized using, for example, the Haploview software (Barrett J C et al. Haploview: analysis and visualization of LD and haplotype maps. *Bioinformatics*. 2005 Jan. 15). The linkage disequilibrium blocks described in Tables 1-528 were identified using Haploview version 4.1 based on the International HapMap Consortium data release 22.

In accordance with the present invention, SNPs have been identified in a study using a whole-genome case-control approach to identify single nucleotide polymorphisms that were closely associated with the development of endometriosis, as well as SNPs found to be in linkage disequilibrium with (i.e., within the same linkage disequilibrium block as) the endometriosis-associated SNPs, which can provide haplotypes (i.e., groups of SNPs that are co-inherited) to be readily inferred. Thus, the present invention provides individual SNPs associated with endometriosis, as well as combinations of SNPs and haplotypes in genetic regions associated with endometriosis, methods of detecting these polymorphisms in a test sample, methods of determining the risk of an individual of having or developing endometriosis and for clinical sub-classification of endometriosis.

The present invention also provides SNPs associated with endometriosis, as well as SNPs that were previously known in the art, but were not previously known to be associated with endometriosis. Accordingly, the present invention provides novel compositions and methods based on the SNPs disclosed herein, and also provides novel methods of using the known but previously unassociated SNPs in methods relating to endometriosis (e.g., for diagnosing endometriosis. etc.).

Particular SNP alleles of the present invention can be associated with either an increased risk of having or developing endometriosis, or a decreased risk of having or developing endometriosis. SNP alleles that are associated with a decreased risk may be referred to as "protective" alleles, and SNP alleles that are associated with an increased risk may be referred to as "susceptibility" alleles, "risk factors", or "high-risk" alleles. Thus, whereas certain SNPs can be assayed to determine whether an individual possesses a SNP allele that is indicative of an increased risk of having or developing endometriosis (i.e., a susceptibility allele), other SNPs can be assayed to determine whether an individual possesses a SNP allele that is indicative of a decreased risk of having or developing endometriosis (i.e., a protective allele). Similarly, particular SNP alleles of the present invention can be associated with either an increased or decreased likelihood of responding to a particular treatment. The term "altered" may be used herein to encompass either of these two possibilities (e.g., an increased or a decreased risk/likelihood).

Those skilled in the art will readily recognize that nucleic acid molecules may be double-stranded molecules and that reference to a particular site on one strand refers, as well, to the corresponding site on a complementary strand. In defining a SNP position, SNP allele, or nucleotide sequence, reference to an adenine, a thymine (uridine), a cytosine, or a guanine at a particular site on one strand of a nucleic acid molecule also defines the complementary thymine (uridine), adenine, guanine, or cytosine (respectively) at the corresponding site on a complementary strand of the nucleic acid molecule. Thus, reference may be made to either strand in order to refer to a particular SNP position, SNP allele, or nucleotide sequence. Probes and primers may be designed to hybridize to either strand and SNP genotyping methods disclosed herein may generally target either strand. Throughout the specification, in identifying a SNP position, reference is generally made to the forward or "sense" strand, solely for the purpose of convenience. Since endogenous nucleic acid sequences exist in the form of a double helix (a duplex comprising two complementary nucleic acid strands), it is understood that the SNPs disclosed herein will have counterpart nucleic acid sequences and SNPs associated with the complementary "reverse" or "antisense" nucleic acid strand. Such complementary nucleic acid sequences, and the complementary SNPs present in those sequences, are also included within the scope of the present invention.

Isolated Nucleic Acid Molecules

The present invention provides isolated nucleic acid molecules that contain one or more SNPs disclosed in Tables 1-528. Table 1 provides context nucleic acid sequences. Tables 2-528 provide only rs identification numbers; however, the context sequences for such SNPs are known and disclosed in the art, and are not therefore shown in the tables. Isolated nucleic acid molecules contain one or more SNPs identified in Tables 1-528. Isolated nucleic acid molecules containing one or more SNPs disclosed in Tables 1-528 may be interchangeably referred to throughout the present text as "SNP-containing nucleic acid molecules." The isolated nucleic acid molecules of the present invention also include probes and primers (which are described in greater detail below in the section entitled "SNP Detection Reagents"), which may be used for assaying the disclosed SNPs, and isolated full-length genes, transcripts, cDNA molecules, and fragments thereof, which may be used for such purposes as expressing an encoded protein.

As used herein, an "isolated nucleic acid molecule" generally is one that contains a SNP of the present invention or one that hybridizes to such molecule such as a nucleic acid with a complementary sequence, and is separated from most other nucleic acids present in the natural source of the nucleic acid molecule. Moreover, an "isolated" nucleic acid molecule, such as a cDNA molecule containing a SNP of the present invention, can be substantially free of other cellular material, or culture medium when produced by recombinant techniques, or chemical precursors or other chemicals when chemically synthesized. A nucleic acid molecule can be fused to other coding or regulatory sequences and still be considered "isolated." Nucleic acid molecules present in non-human transgenic animals, which do not naturally occur in the animal, are also considered "isolated". For example, recombinant DNA molecules contained in a vector are considered "isolated". Further examples of "isolated" DNA molecules include recombinant DNA molecules maintained in heterologous host cells, and purified (partially or substantially) DNA molecules in solution. Isolated RNA molecules include in vivo or in vitro RNA transcripts of the isolated SNP-containing DNA molecules of the present invention. Isolated nucleic acid molecules according to the present invention further include such molecules produced synthetically.

Generally, an isolated SNP-containing nucleic acid molecule comprises one or more SNP positions disclosed by the present invention with flanking nucleotide sequences on either side of the SNP positions. A flanking sequence can include nucleotide residues that are naturally associated with the SNP site and/or heterologous nucleotide sequences. The flanking sequence may be up to about 100, 60, 50, 30, 25, 20, 15, 10, 8, or 4 nucleotides (or any other length in-between) on either side of a SNP position.

For full-length genes and entire protein-coding sequences, a SNP flanking sequence can be, for example, up to, but not limited to, about 5 KB, 4 KB, 3 KB, 2 KB, 1 KB on either side of the SNP. Furthermore, in such instances, the isolated nucleic acid molecule comprises exonic sequences (including protein-coding and/or non-coding exonic sequences), but may also include intronic sequences. Thus, any protein coding sequence may be either contiguous or separated by introns. The important point is that the nucleic acid is isolated from remote and unimportant flanking sequences and is of appropriate length such that it can be subjected to the specific manipulations or uses described herein such as recombinant protein expression, preparation of probes and primers for assaying the SNP position, and other uses specific to the SNP-containing nucleic acid sequences.

An isolated SNP-containing nucleic acid molecule can comprise, for example, a full-length gene or transcript, such as a gene isolated from genomic DNA (e.g., by cloning or PCR amplification), a cDNA molecule, or an mRNA transcript molecule. Furthermore, fragments of such full-length genes and transcripts that contain one or more SNPs disclosed herein are also encompassed by the present invention, and such fragments may be used, for example, to express any part of a protein, such as a particular functional domain or an antigenic epitope.

Thus, the present invention also encompasses fragments of the nucleic acid sequences contiguous to the SNPs disclosed in Tables 1-528, contiguous nucleotide sequence at least about 8 or more nucleotides, more preferably at least about 12 or more nucleotides, and even more preferably at least about 16 or more nucleotides. Further, a fragment could comprise at least about 18, 20, 22, 25, 30, 40, 50, 60, 100, 250 or 500 (or any other number in-between) nucleotides in length. The length of the fragment will be based on its intended use. For example, the fragment can be useful as a polynucleotide probe or primer. Such fragments can be isolated using nucleotide sequences comprising one of the SNPs in Tables 1-528 for the synthesis of a polynucleotide probe. A labeled probe can then be used, for example, to screen a cDNA library, genomic DNA library, or mRNA to isolate nucleic acid corresponding to the coding region. Further, primers can be used in amplification reactions, such as for purposes of assaying one or more SNPs sites or for cloning specific regions of a gene.

An isolated nucleic acid molecule of the present invention further encompasses a SNP-containing polynucleotide that is the product of any one of a variety of nucleic acid amplification methods, which are used to increase the copy numbers of a polynucleotide of interest in a nucleic acid sample. Such amplification methods are well known in the art, and they include but are not limited to, polymerase chain reaction (PCR) (U.S. Pat. Nos. 4,683,195; and 4,683,202; PCR Technology: Principles and Applications for DNA Amplification, ed. H. A. Erlich, Freeman Press, NY, N.Y., 1992), ligase chain reaction (LCR) (Wu and Wallace, Genomics 4:560, 1989; Landegren et al., Science 241:1077, 1988), strand displacement amplification (SDA) (U.S. Pat. Nos. 5,270,184; and 5,422,252), transcription-mediated amplification (TMA) (U.S. Pat. No. 5,399,491), linked linear amplification (LLA) (U.S. Pat. No. 6,027,923), and the like, and isothermal amplification methods such as nucleic acid sequence based amplification (NASBA), and self-sustained sequence replication (Guatelli et al., Proc. Natl. Acad. Sci. USA 87: 1874, 1990). Based on such methodologies, a person skilled in the art can readily design primers in any suitable regions 5' and 3' to a SNP disclosed herein. Such primers may be used to amplify DNA of any length so long that it contains the SNP of interest in its sequence.

As used herein, an "amplified polynucleotide" of the invention is a SNP-containing nucleic acid molecule whose amount has been increased at least two fold by any nucleic acid amplification method performed in vitro as compared to its starting amount in a test sample. In other preferred embodiments, an amplified polynucleotide is the result of at least ten fold, fifty fold, one hundred fold, one thousand fold, or even ten thousand fold increase as compared to its starting amount in a test sample. In a typical PCR amplification, a polynucleotide of interest is often amplified at least fifty thousand fold in amount over the unamplified genomic DNA, but the precise amount of amplification needed for an assay depends on the sensitivity of the subsequent detection method used.

Generally, an amplified polynucleotide is at least about 16 nucleotides in length. More typically, an amplified polynucleotide is at least about 20 nucleotides in length. In a preferred embodiment of the invention, an amplified polynucleotide is at least about 30 nucleotides in length. In a more preferred embodiment of the invention, an amplified polynucleotide is at least about 32, 40, 45, 50, or 60 nucleotides in length. In yet another preferred embodiment of the invention, an amplified polynucleotide is at least about 100, 200, or 300 nucleotides in length. While the total length of an amplified polynucleotide of the invention can be as long as an exon, an intron or the entire gene where the SNP of interest resides, an amplified product is typically no greater than about 1,000 nucleotides in length (although certain amplification methods may generate amplified products greater than 1000 nucleotides in length). More preferably, an amplified polynucleotide is not greater than about 600 nucleotides in length. It is understood that irrespective of the length of an amplified polynucleotide, a SNP of interest may be located anywhere along its sequence.

In a specific embodiment of the invention, the amplified product is at least about 201 nucleotides in length, comprises one of the nucleotide sequences shown in Tables 1-528. Such a product may have additional sequences on its 5' end or 3' end or both. In another embodiment, the amplified product is about 101 nucleotides in length, and it contains a SNP disclosed herein. Generally, the SNP is located at the middle of the amplified product (e.g., at position 101 in an amplified product that is 201 nucleotides in length, or at position 51 in an amplified product that is 101 nucleotides in length), or within 1, 2, 3, 4, 5, 6, 7, 8, 9, 10, 12, 15, or 20 nucleotides from the middle of the amplified product (however, as indicated above, the SNP of interest may be located anywhere along the length of the amplified product).

The present invention provides isolated nucleic acid molecules that comprise, consist of, or consist essentially of one or more SNPs disclosed herein, complements thereof, and SNP-containing fragments thereof.

Accordingly, the present invention provides nucleic acid molecules that consist of any of the nucleotide sequences comprising one of the SNPs shown in Tables 1-528. A nucleic acid molecule consists of a nucleotide sequence when the nucleotide sequence is the complete nucleotide sequence of the nucleic acid molecule.

The present invention further provides nucleic acid molecules that consist essentially of any of the SNPs shown in Tables 1-528. A nucleic acid molecule consists essentially of a nucleotide sequence when such a nucleotide sequence includes only one of the SNPs disclosed in Tables 1-528, and no other SNPs associated with endometriosis, although additional nucleotide sequence may be included that does not include any additional SNPs associated with endometriosis.

The present invention further provides nucleic acid molecules that comprise any of the SNPs shown in Tables 1-528. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleotide residues, such as residues that are naturally associated with it or heterologous nucleotide sequences. Such a nucleic acid molecule can have one to a few additional nucleotides or can comprise many more additional nucleotides. A brief description of how various types of these nucleic acid molecules can be readily made and isolated are well known to those of ordinary skill in the art (Sambrook and Russell, 2000, Molecular Cloning: A Laboratory Manual, Third ed. Woodbury, N.Y.: CSHL Press; 2001).

Isolated nucleic acid molecules can be in the form of RNA, such as mRNA, or in the form DNA, including cDNA and genomic DNA, which may be obtained, for example, by molecular cloning or produced by chemical synthetic techniques or by a combination thereof (Sambrook and Russell, 2000, Molecular Cloning: A Laboratory Manual, Third ed. Woodbury, N.Y.: CSHL Press; 2001). Furthermore, isolated nucleic acid molecules, particularly SNP detection reagents such as probes and primers, can also be partially or completely in the form of one or more types of nucleic acid analogs, such as peptide nucleic acid (PNA) (U.S. Pat. Nos. 5,539,082; 5,527,675; 5,623,049; 5,714,331). The nucleic acid, especially DNA, can be double-stranded or single-stranded. Single-stranded nucleic acid can be the coding strand (sense strand) or the complementary non-coding strand (anti-sense strand). DNA, RNA, or PNA segments can be assembled, for example, from fragments of the human genome (in the case of DNA or RNA) or single nucleotides, short oligonucleotide linkers, or from a series of oligonucleotides, to provide a synthetic nucleic acid molecule. Nucleic acid molecules can be readily synthesized using the sequences provided herein as a reference; oligonucleotide and PNA oligomer synthesis techniques are well known in the art (see, Corey D R. Peptide nucleic acids: expanding the scope of nucleic acid recognition. Trends Biotechnol. June 1997; 15(6):224-229 and Hyrup B, Nielsen P E. Peptide nucleic acids (PNA): synthesis, properties and potential applications. Bioorg Med Chem. January 1996; 4(1):5-23).

The present invention encompasses nucleic acid analogs that contain modified, synthetic, or non-naturally occurring nucleotides or structural elements or other alternative/modified nucleic acid chemistries known in the art. Such nucleic acid analogs are useful, for example, as detection reagents (e.g., primers/probes) for detecting one or more SNPs identified in Tables 1-528. Furthermore, kits/systems (such as beads, arrays, etc.) that include these analogs are also encompassed by the present invention.

Additional examples of nucleic acid modifications that improve the binding properties and/or stability of a nucleic acid include the use of base analogs such as inosine, intercalators (U.S. Pat. No. 4,835,263) and the minor groove binders (U.S. Pat. No. 5,801,115). Thus, references herein to nucleic acid molecules, SNP-containing nucleic acid molecules, SNP detection reagents (e.g., probes and primers), oligonucleotides/polynucleotides include PNA oligomers and other nucleic acid analogs. Other examples of nucleic acid analogs and alternative/modified nucleic acid chemistries known in the art are described in Beaucage et al. (Current Protocols in Nucleic Acid Chemistry. New York: John Wiley and Sons; 2007).

Further variants of the SNPs disclosed in Tables 1-528, such as naturally occurring allelic variants (as well as orthologs and paralogs) and synthetic variants produced by mutagenesis techniques, can be identified and/or produced using methods well known in the art. Such further variants can comprise a nucleotide sequence that shares at least 70-80%, 80-85%, 85-90%, 91%, 92%, 93%, 94%, 95%, 96%, 97%, 98%, or 99% sequence identity with a nucleic acid sequence contiguous to the SNPs disclosed in Tables 1-528 (or a fragment thereof) and that includes a novel SNP allele disclosed in Tables 1-528. Thus, the present invention specifically contemplates isolated nucleic acid molecule that have a certain degree of sequence variation compared with the sequences shown in Tables 1-528, but that contain a novel SNP allele disclosed herein. In other words, as long as an isolated nucleic acid molecule contains a novel SNP allele disclosed herein, other portions of the nucleic acid molecule that flank the novel SNP allele can vary to some degree from the specific genomic and context sequences surrounding the SNPs listed in Tables 1-528.

The present invention further provides non-coding fragments of the nucleic acid molecules disclosed in Tables 1-528. Preferred non-coding fragments include, but are not limited to, promoter sequences, enhancer sequences, intronic sequences, 5' untranslated regions (UTRs), 3' untranslated regions, gene modulating sequences and gene termination sequences. Such fragments are useful, for example, in controlling heterologous gene expression and in developing screens to identify gene-modulating agents.

SNP Detection Reagents

In a specific aspect of the present invention, the SNPs disclosed herein can be used for the design of SNP detection reagents. As used herein, a "SNP detection reagent" is a reagent that specifically detects a specific target SNP position disclosed herein, and that is preferably specific for a particular nucleotide (allele) of the target SNP position (i.e., the detection reagent preferably can differentiate between different alternative nucleotides at a target SNP position, thereby allowing the identity of the nucleotide present at the target SNP position to be determined). Typically, such detection reagent hybridizes to a target SNP-containing nucleic acid molecule by complementary base-pairing in a sequence specific manner, and discriminates the target variant sequence from other nucleic acid sequences such as an art-known form in a test sample. An example of a detection reagent is a probe that hybridizes to a target nucleic acid containing one or more of the SNPs disclosed herein. In a preferred embodiment, such a probe can differentiate between nucleic acids having a particular nucleotide (allele) at a target SNP position from other nucleic acids that have a different nucleotide at the same target SNP position. In addition, a detection reagent may hybridize to a specific region 5' and/or 3' to a SNP position, particularly a region corresponding to the context sequences provided in the SNPs disclosed herein. Another example of a detection reagent is a primer which acts as an initiation point of nucleotide extension along a complementary strand of a target polynucleotide. The SNP sequence information provided herein is also useful for designing primers, e.g. allele-specific primers, to amplify (e.g., using PCR) any SNP of the present invention.

In one preferred embodiment of the invention, a SNP detection reagent is a synthetic polynucleotide molecule, such as an isolated or synthetic DNA or RNA polynucleotide probe or primer or PNA oligomer, or a combination of DNA, RNA and/or PNA that hybridizes to a segment of a target nucleic acid molecule containing a SNP identified herein. A detection reagent in the form of a polynucleotide may optionally contain modified base analogs, intercalators or minor groove binders. Multiple detection reagents such as probes may be, for example, affixed to a solid support (e.g., arrays or beads) or supplied in solution (e.g., probe/primer sets for enzymatic reactions such as PCR, RT-PCR, TaqMan assays, or primer-extension reactions) to form a SNP detection kit.

A probe or primer typically is a substantially purified oligonucleotide. Such oligonucleotide typically comprises a region of complementary nucleotide sequence that hybridizes under stringent conditions to at least about 8, 10, 12, 16, 18, 20, 22, 25, 30, 40, 50, 60, 100 (or any other number in-between) or more consecutive nucleotides in a target nucleic acid molecule. Depending on the particular assay, the consecutive nucleotides can either include the target SNP position, or be a specific region in close enough proximity 5' and/or 3' to the SNP position to carry out the desired assay.

Other preferred primer and probe sequences can readily be determined using the nucleotide sequences disclosed herein. It will be apparent to one of skill in the art that such primers and probes are directly useful as reagents for genotyping the SNPs of the present invention, and can be incorporated into any kit/system format.

In order to produce a probe or primer specific for a target SNP-containing sequence, the gene/transcript and/or context sequence surrounding the SNP of interest is typically examined using a computer algorithm which starts at the 5' or at the 3' end of the nucleotide sequence. Typical algorithms will then identify oligomers of defined length that are unique to the gene/SNP context sequence, have a GC content within a range suitable for hybridization, lack predicted secondary structure that may interfere with hybridization, and/or possess other desired characteristics or that lack other undesired characteristics.

A primer or probe of the present invention is typically at least about 8 nucleotides in length. In one embodiment of the invention, a primer or a probe is at least about 10 nucleotides in length. In a preferred embodiment, a primer or a probe is at least about 12 nucleotides in length. In a more preferred embodiment, a primer or probe is at least about 16, 17, 18, 19, 20, 21, 22, 23, 24 or 25 nucleotides in length. While the maximal length of a probe can be as long as the target sequence to be detected, depending on the type of assay in which it is employed, it is typically less than about 50, 60, 65, or 70 nucleotides in length. In the case of a primer, it is typically less than about 30 nucleotides in length. In a specific preferred embodiment of the invention, a primer or a probe is within the length of about 18 and about 28 nucleotides. However, in other embodiments, such as nucleic acid arrays and other embodiments in which probes are affixed to a substrate, the probes can be longer, such as on the order of 30-70, 75, 80, 90, 100, or more nucleotides in length (see the section below entitled "SNP Detection Kits and Systems").

For analyzing SNPs, it may be appropriate to use oligonucleotides specific for alternative SNP alleles. Such oligonucleotides which detect single nucleotide variations in target sequences may be referred to by such terms as "allele-specific oligonucleotides", "allele-specific probes", or "allele-specific primers". The design and use of allele-specific probes for analyzing polymorphisms is described in, e.g., Cotton R G H, et al., eds. Mutation Detection: A Practical Approach. New York: Oxford University Press; 1998. Harnes B D, ed. The Practical Approach Series and Saiki R K, et al. Analysis of enzymatically amplified beta-globin and HLA-DQ alpha DNA with allele-specific oligonucleotide probes. Nature. Nov. 13-19 1986; 324(6093): 163-166.

While the design of each allele-specific primer or probe depends on variables such as the precise composition of the nucleotide sequences flanking a SNP position in a target nucleic acid molecule, and the length of the primer or probe, another factor in the use of primers and probes is the stringency of the condition under which the hybridization between the probe or primer and the target sequence is performed. Higher stringency conditions utilize buffers with lower ionic strength and/or a higher reaction temperature, and tend to require a more perfect match between probe/primer and a target sequence in order to form a stable duplex. If the stringency is too high, however, hybridization may not occur at all. In contrast, lower stringency conditions utilize buffers with higher ionic strength and/or a lower reaction temperature, and permit the formation of stable duplexes with more mismatched bases between a probe/primer and a target sequence. By way of example and not limitation, exemplary conditions for high stringency hybridization conditions using an allele-specific probe are as follows: Prehybridization with a solution containing 5× standard saline phosphate EDTA (SSPE), 0.5% NaDodSO$_4$ (SDS) at 55° C., and incubating probe with target nucleic acid molecules in the same solution at the same temperature, followed by washing with a solution containing 2×SSPE, and 0.1% SDS at 55° C. or room temperature.

Moderate stringency hybridization conditions may be used for allele-specific primer extension reactions with a solution containing, e.g., about 50 mM KCl at about 46° C. Alternatively, the reaction may be carried out at an elevated temperature such as 60° C. In another embodiment, a moderately stringent hybridization condition suitable for oligonucleotide ligation assay (OLA) reactions wherein two probes are ligated if they are completely complementary to the target sequence may utilize a solution of about 100 mM KCl at a temperature of 46° C.

In a hybridization-based assay, allele-specific probes can be designed that hybridize to a segment of target DNA from one individual but do not hybridize to the corresponding segment from another individual due to the presence of different polymorphic forms (e.g., alternative SNP alleles/nucleotides) in the respective DNA segments from the two individuals. Hybridization conditions should be sufficiently stringent that there is a significant detectable difference in hybridization intensity between alleles, and preferably an essentially binary response, whereby a probe hybridizes to only one of the alleles or significantly more strongly to one allele. While a probe may be designed to hybridize to a target sequence that contains a SNP site such that the SNP site aligns anywhere along the sequence of the probe, the probe is preferably designed to hybridize to a segment of the target sequence such that the SNP site aligns with a central position of the probe (e.g., a position within the probe that is at least three nucleotides from either end of the probe). This design of probe generally achieves good discrimination in hybridization between different allelic forms.

In another embodiment, a probe or primer may be designed to hybridize to a segment of target DNA such that the SNP aligns with either the 5' most end or the 3' most end of the probe or primer. In a specific preferred embodiment which is particularly suitable for use in a oligonucleotide ligation assay (U.S. Pat. No. 4,988,617), the most 3' nucleotide of the probe aligns with the SNP position in the target sequence.

Oligonucleotide probes and primers may be prepared by methods well known in the art. Chemical synthetic methods include, but are limited to, the phosphotriester method described by Narang et al. (Improved phosphotriester method for the synthesis of gene fragments. Methods Enzymol. 1979; 68:90-98); the phosphodiester method described by Brown et al., (Chemical synthesis and cloning of a tyrosine tRNA gene. Methods Enzymol. 1979; 68:109-151), the diethylphosphoamidate method described by Beaucage and Caruthers (Deoxynucleoside phosphoramidites—A new class of key intermediates for deoxypolynucleotide synthesis. Tetrahedron Letters. 1981; 22(20): 1859-1862); and the solid support method described in U.S. Pat. No. 4,458,066.

Allele-specific probes are often used in pairs (or, less commonly, in sets of 3 or 4, such as if a SNP position is known to have 3 or 4 alleles, respectively, or to assay both strands of a nucleic acid molecule for a target SNP allele), and such pairs may be identical except for a one nucleotide mismatch that represents the allelic variants at the SNP position. Commonly, one member of a pair perfectly matches a reference form of a target sequence that has a more common SNP allele (i.e., the allele that is more frequent in the target population) and the other member of the pair perfectly matches a form of the target sequence that has a less common SNP allele (i.e., the allele that is rarer in the target population). In the case of an array, multiple pairs of probes can be immobilized on the same support for simultaneous analysis of multiple different polymorphisms.

In one type of PCR-based assay, an allele-specific primer hybridizes to a region on a target nucleic acid molecule that overlaps a SNP position and only primes amplification of one allelic form to which the primer exhibits perfect complementarity (Gibbs R A, et al. Detection of single DNA base differences by competitive oligonucleotide priming. Nucleic Acids Res. Apr. 11 1989; 17(7):2437-2448). Typically, the primer's 3'-most nucleotide is aligned with and complementary to the SNP position of the target nucleic acid molecule. This primer is used in conjunction with a second primer that hybridizes at a distal site. Amplification proceeds from the two primers, producing a detectable product that indicates which allelic form is present in the test sample. A control is usually performed with a second pair of primers, one of which shows a single base mismatch at the polymorphic site and the other of which exhibits perfect complementarity to a distal site. The single-base mismatch prevents amplification or substantially reduces amplification efficiency, so that either no detectable product is formed or it is formed in lower amounts or at a slower pace. The method generally works most effectively when the mismatch is at the 3'-most position of the oligonucleotide (i.e., the 3'-most position of the oligonucleotide aligns with the target SNP position) because this position is most destabilizing to elongation from the primer (see, e.g., WIPO patent WO/1993/022456). This PCR-based assay can be utilized as part of the TaqMan assay, described below.

In a specific embodiment of the invention, a primer of the invention contains a sequence substantially complementary to a segment of a target SNP-containing nucleic acid molecule except that the primer has a mismatched nucleotide in one of the three nucleotide positions at the 3'-most end of the primer, such that the mismatched nucleotide does not base pair with a particular allele at the SNP site. In a preferred embodiment, the mismatched nucleotide in the primer is the second from the last nucleotide at the 3'-most position of the primer. In a more preferred embodiment, the mismatched nucleotide in the primer is the last nucleotide at the 3'-most position of the primer.

In another embodiment of the invention, a SNP detection reagent of the invention is labeled with a fluorogenic reporter dye that emits a detectable signal. While the preferred reporter dye is a fluorescent dye, any reporter dye that can be attached to a detection reagent such as an oligonucleotide probe or primer is suitable for use in the invention. Such dyes include, but are not limited to, Acridine, AMCA, BODIPY, Cascade Blue, Cy2, Cy3, Cy5, Cy7, Dabcyl, Edans, Eosin, Erythrosin, Fluorescein, 6-Fam, Tet, Joe, Hex, Oregon Green, Rhodamine, Rhodol Green, Tamra, Rox, and Texas Red.

In yet another embodiment of the invention, the detection reagent may be further labeled with a quencher dye such as Tamra, especially when the reagent is used as a self-quenching probe such as a TaqMan (U.S. Pat. Nos. 5,210,015 and 5,538,848) or Molecular Beacon probe (U.S. Pat. Nos. 5,118,801 and 5,312,728), or other stemless or linear beacon probe (Livak K J, et al. Oligonucleotides with fluorescent dyes at opposite ends provide a quenched probe system useful for detecting PCR product and nucleic acid hybridization. PCR Methods Appl. June 1995; 4(6):357-362. Tyagi S, Kramer F R. Molecular beacons: probes that fluoresce upon hybridization. Nat Biotechnol. March 1996; 14(3):303-308. Nazarenko I A, et al. A closed tube format for amplification and detection of DNA based on energy transfer. Nucleic Acids Res. Jun. 15 1997; 25(12):2516-2521).

The detection reagents of the invention may also contain other labels, including but not limited to, biotin for streptavidin binding and oligonucleotide for binding to another complementary oligonucleotide such as pairs of zipcodes.

The present invention also contemplates reagents that do not contain (or that are complementary to) a SNP nucleotide identified herein but that are used to assay one or more SNPs disclosed herein. For example, primers that flank, but do not hybridize directly to a target SNP position provided herein are useful in primer extension reactions in which the primers hybridize to a region adjacent to the target SNP position (i.e., within one or more nucleotides from the target SNP site). During the primer extension reaction, a primer is typically not able to extend past a target SNP site if a particular nucleotide (allele) is present at that target SNP site, and the primer extension product can readily be detected in order to determine which SNP allele is present at the target SNP site. For example, particular ddNTPs are typically used in the primer extension reaction to terminate primer extension once a ddNTP is incorporated into the extension product (a primer extension product which includes a ddNTP at the 3'-most end of the primer extension product, and in which the ddNTP corresponds to a SNP disclosed herein, is a composition that is encompassed by the present invention). Thus, reagents that bind to a nucleic acid molecule in a region adjacent to a SNP site, even though the bound sequences do not necessarily include the SNP site itself, are also encompassed by the present invention.

SNP Detection Kits and Systems

A person skilled in the art will recognize that, based on the SNP and associated sequence information disclosed herein, detection reagents can be developed and used to assay any SNP of the present invention individually or in combination, and such detection reagents can be readily incorporated into one of the established kit or system formats which are well known in the art. The terms "kits" and "systems", as used herein in the context of SNP detection reagents, are intended to refer to such things as combinations of multiple SNP detection reagents, or one or more SNP detection reagents in combination with one or more other types of elements or components (e.g., other types of biochemical reagents, containers, packages such as packaging intended for commercial sale, substrates to which SNP detection reagents are attached, electronic hardware components, etc.). Accordingly, the present invention further provides SNP detection kits and systems, including but not limited to, packaged probe and primer sets (e.g., TaqMan probe/primer sets), arrays/microarrays of nucleic acid molecules, and beads that contain one or more probes, primers, or other detection reagents for detecting one or more SNPs of the present invention. The kits/systems can optionally include various electronic hardware components; for example, arrays ("DNA chips") and microfluidic systems ("lab-on-a-chip" systems) provided by various manufacturers typically comprise hardware components. Other kits/systems (e.g., probe/primer sets) may not include electronic hardware components, but may be comprised of, for example, one or more SNP detection reagents (along with, optionally, other biochemical reagents) packaged in one or more containers.

In some embodiments, a SNP detection kit typically contains one or more detection reagents and other components (e.g., a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction, such as amplification and/or detection of a SNP-containing nucleic acid molecule. A kit may further contain means for determining the amount of a target nucleic acid, and means for comparing the amount with a standard, and can comprise instructions for using the kit to detect the SNP-containing nucleic acid molecule of interest. In one embodiment of the present invention, kits are provided which contain the necessary reagents to carry out one or more assays to detect one or more SNPs disclosed herein. In a preferred embodiment of the present invention, SNP detection kits/systems are in the form of nucleic acid arrays, or compartmentalized kits, including microfluidic/lab-on-a-chip systems.

SNP detection kits/systems may contain, for example, one or more probes, or pairs of probes, that hybridize to a nucleic acid molecule at or near each target SNP position. Multiple pairs of allele-specific probes may be included in the kit/system to simultaneously assay large numbers of SNPs, at least one of which is a SNP of the present invention. In some kits/systems, the allele-specific probes are immobilized to a substrate such as an array or bead. For example, the same substrate can comprise allele-specific probes for detecting at least 1; 10; 100; 1000; 10,000; 100,000; 500,000 (or any other number in-between) or substantially all of the SNPs disclosed herein.

The terms "arrays," "microarrays," and "DNA chips" are used herein interchangeably to refer to an array of distinct polynucleotides affixed to a substrate, such as glass, plastic, paper, nylon or other type of membrane, filter, chip, or any other suitable solid support. The polynucleotides can be synthesized directly on the substrate, or synthesized separate from the substrate and then affixed to the substrate. In one embodiment, the microarray is prepared and used according to the methods described in U.S. Pat. No. 5,837,832 (to Chee et al.), PCT application WO1995/011995 (to Chee et al.), Lockhart et al. (Expression monitoring by hybridization to high-density oligonucleotide arrays. Nat Biotechnol. December 1996; 14(13):1675-1680); and Schena et al. (Parallel human genome analysis: microarray-based expression monitoring of 1000 genes. Proc Natl Acad Sci USA. Oct. 1 1996; 93(20):10614-10619), all of which are incorporated herein in their entirety by reference. In other embodiments, such arrays are produced by the methods described in U.S. Pat. No. 5,807,522 (to Brown et al.).

Nucleic acid arrays are reviewed in the following references: Zammatteo et al. (New chips for molecular biology and diagnostics. Biotechnol Annu Rev. 2002; 8:85-101); Sosnowski et al. (Active microelectronic array system for DNA hybridization, genotyping and pharmacogenomic applications. Psychiatr Genet. December 2002; 12(4):181-192); Heller (DNA microarray technology: devices, systems, and applications. Annu Rev Biomed Eng. 2002; 4:129-153); Kolchinsky and Mirzabekov (Analysis of SNPs and other genomic variations using gel-based chips. Hum Mutat. April 2002; 19(4):343-360); and McGall and Christians (High-density genechip oligonucleotide probe arrays. Adv Biochem Eng Biotechnol. 2002; 77:21-42).

Any number of probes, such as allele-specific probes, may be implemented in an array, and each probe or pair of probes can hybridize to a different SNP position. In the case of polynucleotide probes, they can be synthesized at designated areas (or synthesized separately and then affixed to designated areas) on a substrate using a light-directed chemical process. Each DNA chip can contain, for example, thousands to millions of individual synthetic polynucleotide probes arranged in a grid-like pattern and miniaturized (e.g., to the size of a dime). Preferably, probes are attached to a solid support in an ordered, addressable array.

A microarray can be composed of a large number of unique, single-stranded polynucleotides fixed to a solid support. Typical polynucleotides are preferably about 6-60 nucleotides in length, more preferably about 15-30 nucleotides in length, and most preferably about 18-25 nucleotides in length. For certain types of microarrays or other detection kits/systems, it may be preferable to use oligonucleotides that are only about 7-20 nucleotides in length. In other types of arrays, such as arrays used in conjunction with chemiluminescent detection technology, preferred probe lengths can be, for example, about 15-80 nucleotides in length, preferably about 50-70 nucleotides in length, more preferably about 55-65 nucleotides in length, and most preferably about 60 nucleotides in length. The microarray or detection kit can contain polynucleotides that cover the known 5' or 3' sequence of the target SNP site, sequential polynucleotides that cover the full-length sequence of a gene/transcript; or unique polynucleotides selected from particular areas along the length of a target gene/transcript sequence, particularly areas corresponding to one or more SNPs disclosed herein. Polynucleotides used in the microarray or detection kit can be specific to a SNP or SNPs of interest (e.g., specific to a particular SNP allele at a target SNP site, or specific to particular SNP alleles at multiple different SNP sites), or specific to a polymorphic gene/transcript or genes/transcripts of interest.

Hybridization assays based on polynucleotide arrays rely on the differences in hybridization stability of the probes to perfectly matched and mismatched target sequence variants. For SNP genotyping, it is generally preferable that stringency conditions used in hybridization assays are high enough such that nucleic acid molecules that differ from one another at as little as a single SNP position can be differentiated (e.g., typical SNP hybridization assays are designed so that hybridization will occur only if one particular nucleotide is present at a SNP position, but will not occur if an alternative nucleotide is present at that SNP position). Such high stringency conditions may be preferable when using, for example, nucleic acid arrays of allele-specific probes for SNP detection. Such high stringency conditions are described in the preceding section, and are well known to those skilled in the art and can be found in, for example, Ausubel et al. (Current Protocols in Molecular Biology. New York: John Wiley and Sons; 2007).

In other embodiments, the arrays are used in conjunction with chemiluminescent detection technology. The following patents and patent applications, which are all hereby incorporated by reference, provide additional information pertaining to chemiluminescent detection: U.S. patent application Ser. Nos. 10/620,332 and 10/620,333 describe chemiluminescent approaches for microarray detection; U.S. Pat. Nos. 6,124,478, 6,107,024, 5,994,073, 5,981,768, 5,871,958, 5,843,681, 5,800,999, and 5,773,628 describe methods and compositions of dioxetane for performing chemiluminescent detection; and U.S. published application US2002/0110828 discloses methods and compositions for microarray controls.

In one embodiment of the invention, a nucleic acid array can comprise an array of probes of about 15-25 nucleotides in length. In a further embodiment, a nucleic acid array can comprise an array of probes of about 15-75 nucleotides in length. In yet further embodiments, a nucleic acid array can comprise any number of probes, in which at least one probe is capable of detecting one or more SNPs disclosed in Table 1 and/or at least one probe comprises a fragment of one of the sequences selected from the group consisting of those disclosed herein, and sequences complementary thereto, said fragment comprising at least about 8 consecutive nucleotides, preferably 10, 12, 15, 16, 18, 20, more preferably 22, 25, 30, 40, 47, 50, 55, 60, 65, 70, 80, 90, 100, or more consecutive nucleotides (or any other number in-between) and containing (or being complementary to) a SNP. In some embodiments, the nucleotide complementary to the SNP site is within 5, 4, 3, 2, or 1 nucleotide from the center of the probe, more preferably at the center of said probe.

A polynucleotide probe can be synthesized on the surface of the substrate by using a chemical coupling procedure and an ink jet application apparatus, as described in PCT application WO95/251116 (to Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more polynucleotides, or any other number which lends itself to the efficient use of commercially available instrumentation.

Using such arrays or other kits/systems, the present invention provides methods of identifying the SNPs disclosed herein in a test sample. Such methods typically involve incubating a test sample of nucleic acids with an array comprising one or more probes corresponding to at least one SNP position of the present invention, and assaying for binding of a nucleic acid from the test sample with one or more of the probes. Conditions for incubating a SNP detection reagent (or a kit/system that employs one or more such SNP detection reagents) with a test sample vary. Incubation conditions depend on such factors as the format employed in the assay, the detection methods employed, and the type and nature of the detection reagents used in the assay. One skilled in the art will recognize that any one of the commonly available hybridization, amplification and array assay formats can readily be adapted to detect the SNPs disclosed herein.

A SNP detection kit/system of the present invention may include components that are used to prepare nucleic acids from a test sample for the subsequent amplification and/or detection of a SNP-containing nucleic acid molecule. Such sample preparation components can be used to produce nucleic acid extracts, including DNA and/or RNA, extracts from any bodily fluids. In a preferred embodiment of the invention, the bodily fluid is blood, saliva or buccal swabs. The test samples used in the above-described methods will vary based on such factors as the assay format, nature of the detection method, and the specific tissues, cells or extracts used as the test sample to be assayed. Methods of preparing nucleic acids are well known in the art and can be readily adapted to obtain a sample that is compatible with the system utilized.

In yet another form of the kit in addition to reagents for preparation of nucleic acids and reagents for detection of one of the SNPs of this invention, the kit may include a questionnaire inquiring about non-genetic clinical factors such as age, gender, BMI, pelvic pain, infertility or any other non-genetic clinical factors known to be associated with endometriosis.

Another form of kit contemplated by the present invention is a compartmentalized kit. A compartmentalized kit includes any kit in which reagents are contained in separate containers. Such containers include, for example, small glass containers, plastic containers, strips of plastic, glass or paper, or arraying material such as silica. Such containers allow one to efficiently transfer reagents from one compartment to another compartment such that the test samples and reagents are not cross-contaminated, or from one container to another vessel not included in the kit, and the agents or solutions of each container can be added in a quantitative fashion from one compartment to another or to another vessel. Such containers may include, for example, one or more containers which will accept the test sample, one or more containers which contain at least one probe or other SNP detection reagent for detecting one or more SNPs of the present invention, one or more containers which contain wash reagents (such as phosphate buffered saline, Tris-buffers, etc.), and one or more containers which contain the reagents used to reveal the presence of the bound probe or other SNP detection reagents. The kit can optionally further comprise compartments and/or reagents for, for example, nucleic acid amplification or other enzymatic reactions such as primer extension reactions, hybridization, ligation, electrophoresis (preferably capillary electrophoresis), mass spectrometry, and/or laser-induced fluorescent detection. The kit may also include instructions for using the kit. Exemplary compartmentalized kits include microfluidic devices known in the art (see, e.g., Weigl B H, et al. Lab-on-a-chip for drug development. Adv Drug Deliv Rev. Feb. 24 2003; 55(3):349-377). In such microfluidic devices, the containers may be referred to as, for example, microfluidic "compartments", "chambers", or "channels".

Microfluidic devices, which may also be referred to as "lab-on-a-chip" systems, biomedical micro-electro-mechanical systems (bioMEMs), or multicomponent integrated systems, are exemplary kits/systems of the present invention for analyzing SNPs. Such systems miniaturize and compartmentalize processes such as probe/target hybridization, nucleic acid amplification, and capillary electrophoresis reactions in a single functional device. Such microfluidic devices typically utilize detection reagents in at least one aspect of the system, and such detection reagents may be used to detect one or more SNPs of the present invention. One example of a microfluidic system is disclosed in U.S. Pat. No. 5,589,136, which describes the integration of PCR amplification and capillary electrophoresis in chips. Exemplary microfluidic systems comprise a pattern of microchannels designed onto a glass, silicon, quartz, or plastic wafer included on a microchip. The movements of the samples may be controlled by electric, electroosmotic or hydrostatic forces applied across different areas of the microchip to create functional microscopic valves and pumps with no moving parts. Varying the voltage can be used as a means to control the liquid flow at intersections between the micromachined channels and to change the liquid flow rate for pumping across different sections of the microchip. See, for example, U.S. Pat. No. 6,153,073 (to Dubrow et al.), and U.S. Pat. No. 6,156,181 (to Parce et al).

For genotyping SNPs, a microfluidic system may integrate, for example, nucleic acid amplification, primer extension, capillary electrophoresis, and a detection method such as laser induced fluorescence detection.

Uses of Nucleic Acid Molecules

The nucleic acid molecules of the present invention have a variety of uses, especially in the diagnosis and treatment of endometriosis. For example, the nucleic acid molecules are useful as hybridization probes, such as for genotyping SNPs in messenger RNA, transcript, cDNA, genomic DNA, amplified DNA or other nucleic acid molecules comprising one of the SNPs disclosed in Tables 1-528, as well as their orthologs.

A probe can hybridize to any nucleotide sequence along the entire length of a nucleic acid molecule encompassing a SNP of the present invention. Preferably, a probe of the present invention hybridizes to a region of a target sequence that encompasses a SNP. More preferably, a probe hybridizes to a SNP-containing target sequence in a sequence-specific manner such that it distinguishes the target sequence from other nucleotide sequences which vary from the target sequence only by which nucleotide is present at the SNP site. Such a probe is particularly useful for detecting the presence of a SNP-containing nucleic acid in a test sample, or for determining which nucleotide (allele) is present at a particular SNP site (i.e., genotyping the SNP site).

A nucleic acid hybridization probe may be used for determining the presence, level, form, and/or distribution of nucleic acid expression. The nucleic acid whose level is determined can be DNA or RNA. Accordingly, probes specific for the SNPs described herein can be used to assess the presence, expression and/or gene copy number in a given cell, tissue, or organism. These uses are relevant for diagnosis of disorders involving an increase or decrease in gene expression relative to normal levels. In vitro techniques for detection of mRNA include, for example, Northern blot hybridizations and in situ hybridizations. In vitro techniques for detecting DNA include Southern blot hybridizations and in situ hybridizations (Sambrook J, Russell D W. Molecular Cloning: A Laboratory Manual. Third ed. Woodbury, N.Y.: CSHL Press; 2001).

Probes can be used as part of a diagnostic test kit for identifying cells or tissues in which a variant protein is expressed, such as by measuring the level of a variant protein-encoding nucleic acid (e.g., mRNA) in a sample of cells from a subject or determining if a polynucleotide contains a SNP of interest.

Thus, the nucleic acid molecules of the invention can be used as hybridization probes to detect the SNPs disclosed herein, thereby determining whether an individual with the polymorphisms is at risk for endometriosis or has developed early stage endometriosis. Detection of a SNP associated with an endometriosis phenotype provides a diagnostic and/or a prognostic tool for an active endometriosis and/or genetic predisposition to the endometriosis.

The nucleic acid molecules of the invention are also useful as primers to amplify any given region of a nucleic acid molecule, particularly a region containing a SNP of the present invention.

The nucleic acid molecules of the invention are also useful for constructing vectors containing a gene regulatory region of the nucleic acid molecules of the present invention. Further, the nucleic acid molecules of the invention also have therapeutic use in the form of siRNA (small interfering RNA).

SNP Genotyping Methods

The process of determining which specific nucleotide (i.e., allele) is present at each of one or more SNP positions, such as a SNP position in a nucleic acid molecule characterized by a SNP of the present invention, is referred to as SNP genotyping. The present invention provides methods of SNP genotyping, such as for use in screening for endometriosis or related pathologies, or determining predisposition thereto, or determining responsiveness to a form of treatment, or in genome mapping or SNP association analysis, etc.

Nucleic acid samples can be genotyped to determine which allele(s) is/are present at any given genetic region (e.g., SNP position) of interest by methods well known in the art. The neighboring sequence can be used to design SNP detection reagents such as oligonucleotide probes, which may optionally be implemented in a kit format. Exemplary SNP genotyping methods are described in Chen et al. (Single nucleotide polymorphism genotyping: biochemistry, protocol, cost and throughput. Pharmacogenomics J. 2003; 3(2):77-96); Kwok et al., (Detection of single nucleotide polymorphisms. Curr Issues Mol Biol. April 2003; 5(2):43-60); Shi, (Technologies for individual genotyping: detection of genetic polymorphisms in drug targets and disease genes. Am J Pharmacogenomics. 2002; 2(3):197-205); and Kwok, (Methods for genotyping single nucleotide polymorphisms. Annu Rev Genomics Hum Genet. 2001; 2:235-258). Exemplary techniques for high-throughput SNP genotyping are described in Marnellos, (High-throughput SNP analysis for genetic association studies. Curr Opin Drug Discov Devel. May 2003; 6(3):317-321). Common SNP genotyping methods include, but are not limited to, TaqMan assays, molecular beacon assays, nucleic acid arrays, allele-specific primer extension, allele-specific PCR, arrayed primer extension, homogeneous primer extension assays, primer extension with detection by mass spectrometry, mass spectrometry with or with monoisotopic dNTPs (U.S. Pat. No. 6,734,294), pyrosequencing, multiplex primer extension sorted on genetic arrays, ligation with rolling circle amplification, homogeneous ligation, OLA (U.S. Pat. No. 4,988,167), multiplex ligation reaction sorted on genetic arrays, restriction-fragment length polymorphism, single base extension-tag assays, and the Invader assay. Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, electrospray mass spectrometry, and electrical detection.

Various methods for detecting polymorphisms include, but are not limited to, methods in which protection from cleavage agents is used to detect mismatched bases in RNA/RNA or RNA/DNA duplexes (Myers R M, et al. A general method for saturation mutagenesis of cloned DNA fragments. Science. Jul. 19 1985; 229(4710):242-247. Cotton R G H, et al. Reactivity of Cytosine and Thymine in Single-Base-Pair Mismatches with Hydroxylamine and Osmium Tetroxide and Its Application to the Study of Mutations. PNAS. Jun. 15, 1988; 85(12):4397-4401. Saleeba J A, Cotton R G. Chemical cleavage of mismatch to detect mutations. Methods Enzymol. 1993; 217:286-295), comparison of the electrophoretic mobility of variant and wild type nucleic acid molecules (Orita M, et al. Detection of polymorphisms of human DNA by gel electrophoresis as single-strand conformation polymorphisms. Proc Natl Acad Sci USA. April 1989; 86(8):2766-2770. Cotton R G H. Current methods of mutation detection. Mutation Research. 1993; 285:125-144. Hayashi K. PCR-SSCP: a method for detection of mutations. Genet Anal Tech Appl. June 1992; 9(3):73-79), and assaying the movement of polymorphic or wild-type fragments in polyacrylamide gels containing a gradient of denaturant using denaturing gradient gel electrophoresis (DGGE) (Myers R M, et al. Detection of single base substitutions in total genomic DNA. Nature. Feb. 7-13 1985; 313(6002):495-498). Sequence variations at specific locations can also be assessed by nuclease protection assays such as RNase and S1 protection or chemical cleavage methods.

In a preferred embodiment, SNP genotyping is performed using the TaqMan assay, which is also known as the 5' nuclease assay (U.S. Pat. Nos. 5,210,015 and 5,538,848). The TaqMan assay detects the accumulation of a specific amplified product during PCR. The TaqMan assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively, or vice versa.

Alternatively, the reporter dye may be at the 5' or 3' most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target SNP-containing template which is amplified during PCR, and the probe is designed to hybridize to the target SNP site only if a particular SNP allele is present.

Preferred TaqMan primer and probe sequences can readily be determined using the SNP and associated nucleic acid sequence information provided herein. A number of computer programs, such as Primer Express (Applied Biosystems, Foster City, Calif.), can be used to rapidly obtain optimal primer/probe sets. It will be apparent to one of skill in the art that such primers and probes for detecting the SNPs of the present invention are useful in diagnostic assays for endometriosis and related pathologies, and can be readily incorporated into a kit format. The present invention also includes modifications of the Taqman assay well known in the art such as the use of Molecular Beacon probes (U.S. Pat. Nos. 5,118,801 and 5,312,728) and other variant formats (U.S. Pat. Nos. 5,866,336 and 6,117,635).

Another preferred method for genotyping the SNPs of the present invention is the use of two oligonucleotide probes in an OLA (see, e.g., U.S. Pat. No. 4,988,617). In this method, one probe hybridizes to a segment of a target nucleic acid with its 3' most end aligned with the SNP site. A second probe hybridizes to an adjacent segment of the target nucleic acid molecule directly 3' to the first probe. The two juxtaposed probes hybridize to the target nucleic acid molecule, and are ligated in the presence of a linking agent such as a ligase if there is perfect complementarity between the 3' most nucleotide of the first probe with the SNP site. If there is a mismatch, ligation would not occur. After the reaction, the ligated probes are separated from the target nucleic acid molecule, and detected as indicators of the presence of a SNP.

The following patents, patent applications, and published international patent applications, which are all hereby incorporated by reference, provide additional information pertaining to techniques for carrying out various types of OLA: U.S. Pat. Nos. 6,027,889, 6,268,148, 5,494,810, 5,830,711, and 6,054,564 describe OLA strategies for performing SNP detection; WIPO patents WO/1997/031256 and WO/2000/056927 describe OLA strategies for performing SNP detection using universal arrays, wherein a zipcode sequence can be introduced into one of the hybridization probes, and the resulting product, or amplified product, hybridized to a universal zip code array; WIPO patent WO/2001/092579 (and U.S. application Ser. No. 09/584,905) describes OLA (or LDR) followed by PCR, wherein zipcodes are incorporated into OLA probes, and amplified PCR products are determined by electrophoretic or universal zipcode array readout; U.S. application 60/427,818, 60/445,636, and 60/445,494 describe SNPlex methods and software for multiplexed SNP detection using OLA followed by PCR, wherein zipcodes are incorporated into OLA probes, and amplified PCR products are hybridized with a zipchute reagent, and the identity of the SNP determined from electrophoretic readout of the zipchute. In some embodiments, OLA is carried out prior to PCR (or another method of nucleic acid amplification). In other embodiments, PCR (or another method of nucleic acid amplification) is carried out prior to OLA.

Another method for SNP genotyping is based on mass spectrometry. Mass spectrometry takes advantage of the unique mass of each of the four nucleotides of DNA. SNPs can be unambiguously genotyped by mass spectrometry by measuring the differences in the mass of nucleic acids having alternative SNP alleles. MALDI-TOF (Matrix Assisted Laser Desorption Ionization-Time of Flight) mass spectrometry technology is preferred for extremely precise determinations of molecular mass, such as SNPs. Numerous approaches to SNP analysis have been developed based on mass spectrometry. Preferred mass spectrometry-based methods of SNP genotyping include primer extension assays, which can also be utilized in combination with other approaches, such as traditional gel-based formats and microarrays.

The following references provide further information describing mass spectrometry-based methods for SNP genotyping: Bocker (SNP and mutation discovery using base-specific cleavage and MALDI-TOF mass spectrometry. Bioinformatics. 2003; 19 Suppl 1:i44-53), Storm et al. (MALDI-TOF mass spectrometry-based SNP genotyping. Methods Mol Biol. 2003; 212:241-262), Jurinke et al. (The use of MassARRAY technology for high throughput genotyping. Adv Biochem Eng Biotechnol. 2002; 77:57-74), and Jurinke et al. (Automated genotyping using the DNA MassArray technology. Methods Mol Biol. 2002; 187:179-192).

An even more preferred method for genotyping the SNPs of the present invention is the use of electrospray mass spectrometry for direct analysis of an amplified nucleic acid (see, e.g., U.S. Pat. No. 6,734,294). In this method, in one aspect, an amplified nucleic acid product may be isotopically enriched in an isotope of oxygen (O), carbon (C), nitrogen (N) or any combination of those elements. In a preferred embodiment the amplified nucleic acid is isotopically enriched to a level of greater than 99.9% in the elements of $O^{16}$, $C^{12}$ $^{and}$ $N^{14}$ The amplified isotopically enriched product can then be analyzed by electrospray mass spectrometry to determine the nucleic acid composition and the corresponding SNP genotyping. Isotopically enriched amplified products result in a corresponding increase in sensitivity and accuracy in the mass spectrum. In another aspect of this method an amplified nucleic acid that is not isotopically enriched can also have composition and SNP genotype determined by electrospray mass spectrometry.

SNPs can also be scored by direct DNA sequencing. A variety of automated sequencing procedures can be utilized (Naeve C W, et al. Accuracy of automated DNA sequencing: a multi-laboratory comparison of sequencing results. Biotechniques. September 1995; 19(3):448-453), including sequencing by mass spectrometry (see, e.g., WIPO patent WO/1994/016101; Cohen A S, et al. Emerging technologies for sequencing antisense oligonucleotides: capillary electrophoresis and mass spectrometry. Adv Chromatogr. 1996; 36:127-162; and Griffin H G, Griffin A M. DNA sequencing. Recent innovations and future trends. Appl Biochem Biotechnol. January-February 1993; 38(1-2):147-159). The nucleic acid sequences of the present invention enable one of ordinary skill in the art to readily design sequencing primers for such automated sequencing procedures. Commercial instrumentation, such as the Applied Biosystems 377, 3100, 3700, 3730, and 3730×1 DNA Analyzers (Foster City, Calif.), is commonly used in the art for automated sequencing.

SNP genotyping can include the steps of, for example, collecting a biological sample from a human subject (e.g., sample of tissues, cells, fluids, secretions, etc.), isolating nucleic acids (e.g., genomic DNA, mRNA or both) from the cells of the sample, contacting the nucleic acids with one or more primers which specifically hybridize to a region of the isolated nucleic acid containing a target SNP under conditions such that hybridization and amplification of the target nucleic acid region occurs, and determining the nucleotide present at the SNP position of interest, or, in some assays, detecting the presence or absence of an amplification product (assays can be designed so that hybridization and/or amplification will only occur if a particular SNP allele is present or absent). In some assays, the size of the amplification product is detected and compared to the length of a control sample; for example, deletions and insertions can be detected by a change in size of the amplified product compared to a normal genotype.

SNP genotyping is useful for numerous practical applications, as described below. Examples of such applications include, but are not limited to, SNP-endometriosis association analysis, endometriosis predisposition screening, endometriosis diagnosis, endometriosis prognosis, endometriosis progression monitoring, determining therapeutic strategies based on an individual's genotype, and stratifying a patient population for clinical trials for a treatment such as minimally invasive device for the treatment of endometriosis.

Analysis of Genetic Association Between SNPs and Phenotypic Traits

SNP genotyping for endometriosis diagnosis, endometriosis predisposition screening, endometriosis prognosis and endometriosis treatment and other uses described herein, typically relies on initially establishing a genetic association between one or more specific SNPs and the particular phenotypic traits of interest.

In a genetic association study, the cause of interest to be tested is a certain allele or a SNP or a combination of alleles or a haplotype from several SNPs. Thus, tissue specimens (e.g., saliva) from the sampled individuals may be collected and genomic DNA genotyped for the SNP(s) of interest. In addition to the phenotypic trait of interest, other information such as demographic (e.g., age, gender, ethnicity, etc.), clinical, and environmental information that may influence the outcome of the trait can be collected to further characterize and define the sample set. Specifically, in an endometriosis genetic association study, clinical information such as body mass index, age and diet may be collected. In many cases, these factors are known to be associated with diseases and/or SNP allele frequencies. There are likely gene-environment and/or gene-gene interactions as well. Analysis methods to address gene-environment and gene-gene interactions (for example, the effects of the presence of both susceptibility alleles at two different genes can be greater than the effects of the individual alleles at two genes combined) are discussed below.

After all the relevant phenotypic and genotypic information has been obtained, statistical analyses are carried out to determine if there is any significant correlation between the presence of an allele or a genotype with the phenotypic characteristics of an individual. Preferably, data inspection and cleaning are first performed before carrying out statistical tests for genetic association. Epidemiological and clinical data of the samples can be summarized by descriptive statistics with tables and graphs. Data validation is preferably performed to check for data completion, inconsistent entries, and outliers. Chi-squared tests may then be used to check for significant differences between cases and controls for discrete and continuous variables, respectively. To ensure genotyping quality, Hardy-Weinberg disequilibrium tests can be performed on cases and controls separately. Significant deviation from Hardy-Weinberg equilibrium (HWE) in both cases and controls for individual markers can be indicative of genotyping errors. If HWE is violated in a majority of markers, it is indicative of population substructure that should be further investigated. Moreover, Hardy-Weinberg disequilibrium in cases only can indicate genetic association of the markers with the disease of interest. (Weir B S. Genetic Data Analysis: Methods for Discrete Population Genetic Data. Sunderland, Mass.: Sinauer Associates; 1990).

To test whether an allele of a single SNP is associated with the case or control status of a phenotypic trait, one skilled in the art can compare allele frequencies in cases and controls. Standard chi-squared tests and Fisher exact tests can be carried out on a 2×2 table (2 SNP alleles×2 outcomes in the categorical trait of interest). To test whether genotypes of a SNP are associated, chi-squared tests can be carried out on a 3×2 table (3 genotypes×2 outcomes). Score tests are also carried out for genotypic association to contrast the three genotypic frequencies (major homozygotes, heterozygotes and minor homozygotes) in cases and controls, and to look for trends using 3 different modes of inheritance, namely dominant (with contrast coefficients 2, −1, −1), additive (with contrast coefficients 1, 0, −1) and recessive (with contrast coefficients 1, 1, −2). Odds ratios for minor versus major alleles, and odds ratios for heterozygote and homozygote variants versus the wild type genotypes are calculated with the desired confidence limits, usually 95%. In the present study a software algorithm, PLINK, has been applied to automate the calculation of Hardy-Weinberg equilibrium, chi-square, p-values and odds-ratios for very large numbers of SNPs and Case-Control individuals simultaneously (Purcell S, et al. PLINK: a tool set for whole-genome association and population-based linkage analyses. Am J Hum Genet. September 2007; 81(3):559-575).

In order to control for confounding effects and to test for interactions a stepwise multiple logistic regression analysis using statistical packages such as SAS or R may be performed. Logistic regression is a model-building technique in which the best fitting and most parsimonious model is built to describe the relation between the dichotomous outcome (for instance, getting a certain endometriosis or not) and a set of independent variables (for instance, genotypes of different associated genes, and the associated demographic and environmental factors). The most common model is one in which the logit transformation of the odds ratios is expressed as a linear combination of the variables (main effects) and their cross-product terms (interactions) (Hosmer D W, Lemeshow S. Applied Logistic Regression. Second ed. Hoboken, N.J.: Wiley-Interscience; 2000). To test whether a certain variable or interaction is significantly associated with the outcome, coefficients in the model are first estimated and then tested for statistical significance of their departure from zero.

In addition to performing association tests one marker at a time, haplotype association analysis may also be performed to study a number of markers that are closely linked together. Haplotype association tests can have better power than genotypic or allelic association tests when the tested markers are not the disease-causing mutations themselves but are in linkage disequilibrium with such mutations. In order to perform haplotype association effectively, marker-marker linkage disequilibrium measures, both D' and $r^2$, are typically calculated for the markers within a gene to elucidate the haplotype structure. Recent studies (Daly M J, et al. High-resolution haplotype structure in the human genome. Nat Genet. October 2001; 29(2):229-232) in linkage disequilibrium indicate that SNPs within a gene are organized in block pattern, and a high degree of linkage disequilibrium exists within blocks and very little linkage disequilibrium exists between blocks. Haplotype association with the endometriosis status can be performed using such blocks once they have been elucidated.

Haplotype association tests can be carried out in a similar fashion as the allelic and genotypic association tests. Each haplotype is analogous to an allele in a multi-allelic marker. One skilled in the art can either compare the haplotype frequencies in cases and controls or test genetic association with different pairs of haplotypes. It has been proposed (Schaid D J, et al. Score tests for association between traits and haplotypes when linkage phase is ambiguous. Am J Hum Genet. February 2002; 70(2):425-434) that score tests can be done on haplotypes using the program "haplo.score". In that method, haplotypes are first inferred by EM algorithm and score tests are carried out with a generalized linear model (GLM) framework that allows the adjustment of other factors.

An important decision in the performance of genetic association tests is the determination of the significance level at which significant association can be declared when the p-value of the tests reaches that level. In an exploratory analysis where positive hits will be followed up in subsequent confirmatory testing, an unadjusted p-value <0.1 (a significance level on the lenient side) may be used for generating hypotheses for significant association of a SNP with certain phenotypic characteristics of endometriosis. It is preferred that a p-value <0.05 (a significance level traditionally used in the art) is achieved in order for a SNP to be considered to have an association with endometriosis. It is more preferred that a p-value <0.01 (a significance level on the stringent side) is achieved for an association to be declared. Permutation tests to control for the false discovery rates, FDR, can further be employed (Schaid D J, et al. Score tests for association between traits and haplotypes when linkage phase is ambiguous. Am J Hum Genet. February 2002; 70(2):425-434). Such methods to control for multiplicity would be preferred when the tests are dependent and controlling for false discovery rates is sufficient as opposed to controlling for the experiment-wise error rates.

In replication studies using samples from different populations after statistically significant markers have been identified in the exploratory stage, meta-analyses can then be performed by combining evidence of different studies, such as the original study and the replication study (Rothman K J, Greenland S, eds. Modern Epidemiology. Second ed. Philadelphia, Pa.: Lippincott Williams & Wilkins; 1998, 643-673). If available, association results known in the art for the same SNPs can be included in the meta-analyses.

Since both genotyping and endometriosis status classification can involve errors, sensitivity analyses may be performed to see how odds ratios and p-values would change upon various estimates on genotyping and endometriosis classification error rates.

Once individual risk factors, genetic or non-genetic, have been found for the predisposition to endometriosis, the next step is to set up a classification/prediction scheme to predict the category (for instance, endometriosis or no endometriosis) that an individual will be in depending on his genotypes of associated SNPs and other non-genetic risk factors. Logistic regression for discrete trait and linear regression for continuous trait are standard techniques for such tasks (Draper N R, Smith H. Applied Regression Analysis. Third ed. Hoboken, N.J.: Wiley-Interscience; 1998). Moreover, other techniques can also be used for setting up classification. Such techniques include, but are not limited to, MART, CART, neural network, and discriminant analyses that are suitable for use in comparing the performance of different methods (Hastie T, et al. The Elements of Statistical Learning: Data Mining, Inference, and Prediction. New York: Springer; 2001).

Endometriosis Diagnosis and Predisposition Screening

Information on association/correlation between genotypes and endometriosis-related phenotypes can be exploited in several ways. For example, in the case of a highly statistically significant association between one or more SNPs with predisposition to a disease for which treatment is available, detection of such a genotype pattern in an individual may justify particular treatment, or at least the institution of regular monitoring of the individual. In the case of a weaker but still statistically significant association between a SNP and a human disease, immediate therapeutic intervention or monitoring may not be justified after detecting the susceptibility allele or SNP.

The SNPs of the invention may contribute to endometriosis in an individual in different ways. Some polymorphisms occur within a protein coding sequence and contribute to endometriosis phenotype by affecting protein structure. Other polymorphisms occur in noncoding regions but may exert phenotypic effects indirectly via influence on, for example, replication, transcription, and/or translation. A single SNP may affect more than one phenotypic trait. Likewise, a single phenotypic trait may be affected by multiple SNPs in different genes.

The SNPs of the invention may contribute to endometriosis in an individual in different ways. Some polymorphisms occur within a protein coding sequence and contribute to endometriosis phenotype by affecting protein structure. Other polymorphisms occur in noncoding regions but may exert phenotypic effects indirectly via influence on, for example, replication, transcription, and/or translation. A single SNP may affect more than one phenotypic trait. Likewise, a single phenotypic trait may be affected by multiple SNPs in different genes.

Haplotypes are particularly useful in that, for example, fewer SNPs can be genotyped to determine if a particular genomic region harbors a locus that influences a particular phenotype, such as in linkage disequilibrium-based SNP association analysis.

Linkage disequilibrium (LD) refers to the co-inheritance of alleles (e.g., alternative nucleotides) at two or more different SNP sites at frequencies greater than would be expected from the separate frequencies of occurrence of each allele in a given population. The expected frequency of co-occurrence of two alleles that are inherited independently is the frequency of the first allele multiplied by the frequency of the second allele. Alleles that co-occur at expected frequencies are said to be in "linkage equilibrium". In contrast, LD refers to any non-random genetic association between allele(s) at two or more different SNP sites, which is generally due to the physical proximity of the two loci along a chromosome. LD can occur when two or more SNPs sites are in close physical proximity to each other on a given chromosome and therefore alleles at these SNP sites will tend to remain unseparated for multiple generations with the consequence that a particular nucleotide (allele) at one SNP site will show a non-random association with a particular nucleotide (allele) at a different SNP site located nearby. Hence, genotyping one of the SNP sites will give almost the same information as genotyping the other SNP site that is in LD.

For diagnostic purposes, if a particular SNP site is found to be useful for diagnosing endometriosis, then the skilled artisan would recognize that other SNP sites which are in LD with this SNP site would also be useful for diagnosing the condition. Various degrees of LD can be encountered between two or more SNPs with the result being that some SNPs are more closely associated (i.e., in stronger LD) than others. Furthermore, the physical distance over which LD extends along a chromosome differs between different regions of the genome, and therefore the degree of physical separation between two or more SNP sites necessary for LD to occur can differ between different regions of the genome.

For diagnostic applications, polymorphisms (e.g., SNPs and/or haplotypes) that are not the actual disease-causing (causative) polymorphisms, but are in LD with such causative polymorphisms, are also useful. In such instances, the genotype of the polymorphism(s) that is/are in LD with the causative polymorphism is predictive of the genotype of the causative polymorphism and, consequently, predictive of the phenotype (e.g., endometriosis) that is influenced by the causative SNP(s). Thus, polymorphic markers that are in LD with causative polymorphisms are useful as diagnostic markers, and are particularly useful when the actual causative polymorphism(s) is/are unknown.

Linkage disequilibrium in the human genome is reviewed in: International HapMap Consortium, (A haplotype map of the human genome. Nature. Oct. 27 2005; 437(7063):1299-1320); Wall and Pritchard (Haplotype blocks and linkage disequilibrium in the human genome. Nat Rev Genet. August 2003; 4(8):587-597); Garner and Slatkin (On selecting markers for association studies: patterns of linkage disequilibrium between two and three diallelic loci. Genet Epidemiol. January 2003; 24(1):57-67); Ardlie et al. (Patterns of linkage disequilibrium in the human genome. Nat Rev Genet. April 2002; 3(4):299-309); and Remm and Metspalu (High-density genotyping and linkage disequilibrium in the human genome using chromosome 22 as a model. Curr Opin Chem Biol. February 2002; 6(1):24-30).

The contribution or association of particular SNPs and/or SNP haplotypes with endometriosis phenotypes, such as endometriosis, enables the SNPs of the present invention to be used to develop superior diagnostic tests capable of identifying individuals who express a detectable trait, such as endometriosis as the result of a specific genotype, or individuals whose genotype places them at an increased or decreased risk of developing a detectable trait at a subsequent time as compared to individuals who do not have that genotype. As described herein, diagnostics may be based on a single SNP or a group of SNPs. Combined detection of a plurality of SNPs (for example, 2, 3, 4, 5, 6, 7, 8, 9, 10, 11, 12, 13, 14, 15, 16, 17, 18, 19, 20, 24, 25, 30, 32, 48, 50, 64, 96, 100, or any other number in-between, or more, of the SNPs provided in Tables 1-528 typically increases the probability of an accurate diagnosis. For example, the presence of a single SNP known to correlate with endometriosis might indicate a odds ratio of 1.5 that an individual has or is at risk of developing endometriosis, whereas detection of five SNPs, each of which correlates with endometriosis, might indicate an odds ratio of 9.5 that an individual has or is at risk of developing endometriosis. To further increase the accuracy of diagnosis or predisposition screening, analysis of the SNPs of the present invention can be combined with that of other polymorphisms or other risk factors of endometriosis, such as gender and age.

It will, of course, be understood by practitioners skilled in the treatment or diagnosis of endometriosis that the present invention generally does not intend to provide an absolute identification of individuals who are at risk (or less at risk) of developing endometriosis and/or pathologies related to endometriosis, but rather to indicate a certain increased (or decreased) degree or likelihood of developing the endometriosis based on statistically significant association results. However, this information is extremely valuable as it can be used to, for example, initiate earlier preventive treatments or to allow an individual carrying one or more significant SNPs or SNP haplotypes to regularly scheduled physical exams to monitor for the appearance or change of their endometriosis in order to identify and begin treatment of the endometriosis at an early stage.

The diagnostic techniques of the present invention may employ a variety of methodologies to determine whether a test subject has a SNP or a SNP pattern associated with an increased or decreased risk of developing a detectable trait or whether the individual suffers from a detectable trait as a result of a particular polymorphism/mutation, including, for example, methods which enable the analysis of individual chromosomes for haplotyping, family studies, single sperm DNA analysis, or somatic hybrids. The trait analyzed using the diagnostics of the invention may be any detectable trait that is commonly observed in pathologies and disorders related to endometriosis.

Another aspect of the present invention relates to a method of determining whether an individual is at risk (or less at risk) of developing one or more traits or whether an individual expresses one or more traits as a consequence of possessing a particular trait-causing or trait-influencing allele. These methods generally involve obtaining a nucleic acid sample from an individual and assaying the nucleic acid sample to determine which nucleotide(s) is/are present at one or more SNP positions, wherein the assayed nucleotide(s) is/are indicative of an increased or decreased risk of developing the trait or indicative that the individual expresses the trait as a result of possessing a particular trait-causing or trait-influencing allele.

The SNPs of the present invention also can be used to identify novel therapeutic targets for endometriosis. For example, genes containing the disease-associated variants ("variant genes") or their products, as well as genes or their products that are directly or indirectly regulated by or interacting with these variant genes or their products, can be targeted for the development of therapeutics that, for example, treat the endometriosis or prevent or delay endometriosis onset. The therapeutics may be composed of, for example, small molecules, proteins, protein fragments or peptides, antibodies, nucleic acids, or their derivatives or mimetics which modulate the functions or levels of the target genes or gene products.

The SNPs/haplotypes of the present invention are also useful for improving many different aspects of the drug development process. For example, individuals can be selected for clinical trials based on their SNP genotype. Individuals with SNP genotypes that indicate that they are most likely to respond to or most likely to benefit from a device or a drug can be included in the trials and those individuals whose SNP genotypes indicate that they are less likely to or would not respond to a device or a drug, or suffer adverse reactions, can be eliminated from the clinical trials. This not only improves the safety of clinical trials, but also will enhance the chances that the trial will demonstrate statistically significant efficacy. Furthermore, the SNPs of the present invention may explain why certain previously developed devices or drugs performed poorly in clinical trials and may help identify a subset of the population that would benefit from a drug that had previously performed poorly in clinical trials, thereby "rescuing" previously developed therapeutic treatment methods or drugs, and enabling the methods or drug to be made available to a particular endometriosis patient population that can benefit from it.

Pharmaceutical Compositions

Any of the endometriosis-associated proteins, and encoding nucleic acid molecules, disclosed herein can be used as therapeutic targets (or directly used themselves as therapeutic compounds) for treating endometriosis and related pathologies, and the present disclosure enables therapeutic compounds (e.g., small molecules, antibodies, therapeutic proteins, RNAi and antisense molecules, etc.) to be developed that target (or are comprised of) any of these therapeutic targets.

Variant Proteins Encoded by SNP-Containing Nucleic Acid Molecules

The present invention provides SNP-containing nucleic acid molecules, some of which encode proteins having variant amino acid sequences as compared to the art-known (i.e., wild-type) proteins. These variants will generally be referred to herein as variant proteins/peptides/polypeptides, or polymorphic proteins/peptides/polypeptides of the present invention. The terms "protein", "peptide", and "polypeptide" are used herein interchangeably.

A variant protein of the present invention may be encoded by, for example, a nonsynonymous nucleotide substitution at any one of the cSNP positions disclosed herein. In addition, variant proteins may also include proteins whose expression, structure, and/or function is altered by a SNP disclosed herein, such as a SNP that creates or destroys a stop codon, a SNP that affects splicing, and a SNP in control/regulatory elements, e.g. promoters, enhancers, or transcription factor binding domains.

Uses of Variant Proteins

The variant proteins of the present invention can be used in a variety of ways, including but not limited to, in assays to determine the biological activity of a variant protein, such as in a panel of multiple proteins for high-throughput screening; to raise antibodies or to elicit another type of immune response; as a reagent (including the labeled reagent) in assays designed to quantitatively determine levels of the variant protein (or its binding partner) in biological fluids; as a marker for cells or tissues in which it is preferentially expressed (either constitutively or at a particular stage of tissue differentiation or development or in a endometriosis state); as a target for screening for a therapeutic agent; and as a direct therapeutic agent to be administered into a human subject. Any of the variant proteins disclosed herein may be developed into reagent grade or kit format for commercialization as research products. Methods for performing the uses listed above are well known to those skilled in the art (see, e.g., Sambrook J, Russell D W. Molecular Cloning: A Laboratory Manual. Third ed. Woodbury, N.Y.: CSHL Press; 2001 and Berger S L, Kimmel A R, eds. Guide to Molecular Cloning Techniques. New York: Academic Press; 1987. Methods in Enzymology; No. 152).

Computer-Related Embodiments

The SNPs provided in the present invention may be "provided" in a variety of mediums to facilitate use thereof. As used in this section, "provided" refers to a manufacture, other than an isolated nucleic acid molecule, that contains SNP information of the present invention. Such a manufacture provides the SNP information in a form that allows a skilled artisan to examine the manufacture using means not directly applicable to examining the SNPs or a subset thereof as they exist in nature or in purified form. The SNP information that may be provided in such a form includes any of the SNP information provided by the present invention such as, for example, polymorphic nucleic acid and/or amino acid sequence information, information about observed SNP alleles, alternative codons, populations, allele frequencies, SNP types, and/or affected proteins, or any other information provided by the present invention in Table 1 or in Tables 2-528.

In one application of this embodiment, the SNPs of the present invention can be recorded on a computer readable medium. As used herein, "computer readable medium" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable media can be used to create a manufacture comprising computer readable medium having recorded thereon a nucleotide sequence of the present invention. One such medium is provided with the present application, namely, the present application contains computer readable medium (CD-R) that has nucleic acid sequences (and encoded protein sequences) containing SNPs provided/recorded thereon in ASCII text format in a Sequence Listing along with accompanying Tables that contain detailed SNP and sequence information.

As used herein, "recorded" refers to a process for storing information on computer readable medium. A skilled artisan can readily adopt any of the presently known methods for recording information on computer readable medium to generate manufactures comprising the SNP information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide/amino acid sequence information of the present invention on computer readable medium. For example, the sequence information can be represented in a word processing text file, formatted in commercially-available software such as WordPerfect and Microsoft Word, represented in the form of an ASCII file, or stored in a database application, such as OB2, Sybase, Oracle, or the like. A skilled artisan can readily adapt any number of data processor structuring formats (e.g., text file or database) in order to obtain computer readable medium having recorded thereon the SNP information of the present invention.

By providing the SNPs of the present invention in computer readable form, a skilled artisan can routinely access the SNP information for a variety of purposes. Computer software is publicly available which allows a skilled artisan to access sequence information provided in a computer readable medium. Examples of publicly available computer software include BLAST (Altschul S F, et al. Basic local alignment search tool. J Mol Biol. Oct. 5 1990; 215(3):403-410) and BLAZE (Brutlag D L, et al. BLAZE: An implementation of the Smith-Waterman comparison algorithm on a massively parallel computer. Computers and Chemistry. 1993; 17:203-207) search algorithms.

The present invention further provides systems, particularly computer-based systems, which contain the SNP information described herein. Such systems may be designed to store and/or analyze information on, for example, a large number of SNP positions, or information on SNP genotypes from a large number of individuals. The SNP information of the present invention represents a valuable information source. The SNP information of the present invention stored/analyzed in a computer-based system may be used for such computer-intensive applications as determining or analyzing SNP allele frequencies in a population, mapping endometriosis genes, genotype-phenotype association studies, grouping SNPs into haplotypes, correlating SNP haplotypes with response to particular treatments or for various other bioinformatic, pharmacogenomic or drug development.

As used herein, "a computer-based system" refers to the hardware means, software means, and data storage means used to analyze the SNP information of the present invention. The minimum hardware means of the computer-based systems of the present invention typically comprises a central processing unit (CPU), input means, output means, and data storage means. A skilled artisan can readily appreciate that any one of the currently available computer-based systems are suitable for use in the present invention. Such a system can be changed into a system of the present invention by utilizing the SNP information provided on the CD-R, or a subset thereof, without any experimentation.

As stated above, the computer-based systems of the present invention comprise a data storage means having stored therein SNPs of the present invention and the necessary hardware means and software means for supporting and implementing a search means. As used herein, "data storage means" refers to memory which can store SNP information of the present invention, or a memory access means which can access manufactures having recorded thereon the SNP information of the present invention.

As used herein, "search means" refers to one or more programs or algorithms that are implemented on the computer-based system to identify or analyze SNPs in a target sequence based on the SNP information stored within the data storage means. Search means can be used to determine which nucleotide is present at a particular SNP position in the target sequence. As used herein, a "target sequence" can be any DNA sequence containing the SNP position(s) to be searched or queried.

As used herein, "a target structural motif," or "target motif," refers to any rationally selected sequence or combination of sequences containing a SNP position in which the sequence(s) is chosen based on a three-dimensional configuration that is formed upon the folding of the target motif. There are a variety of target motifs known in the art.

Protein target motifs include, but are not limited to, enzymatic active sites and signal sequences. Nucleic acid target motifs include, but are not limited to, promoter sequences, hairpin structures, and inducible expression elements (protein binding sequences).

A variety of structural formats for the input and output means can be used to input and output the information in the computer-based systems of the present invention. An exemplary format for an output means is a display that depicts the presence or absence of specified nucleotides (alleles) at particular SNP positions of interest. Such presentation can provide a rapid, binary scoring system for many SNPs simultaneously.

EXAMPLES

Overview of Association Study

Endometriosis is a debilitating disease, characterized by the presence of endometrium (glands and stroma) at sites outside of the uterus, which is estimated to affect approximately 14% of all women. Endometrioses often leads to pain, local inflammation, scarring and decreased fertility. This example identifies genetic loci in the form of SNPs associated with endometriosis.

A Genome Wide Association study was performed to identify SNPs associated with Endometriosis. The Affymetrix 6.0 GeneChip technology platform was employed in the study to ascertain genotypic information across a total of 906,600 individual SNPs. In all, 588 individuals diagnosed with Endometriosis were tested and compared to 1535 control individuals. All individuals were of Caucasian decent as determined by Principal Component Analysis implemented in the computer algorithm EIGENSTRAT (Nature Genetics 38, 904-909 (2006) Published online: 23 Jul. 2006; |doi:10.1038/ng1847 Principal components analysis corrects for stratification in genome-wide association studies Alkes L Pricel, 2, Nick J Patterson2, Robert M Plenge2, 3, Michael E Weinblatt3, Nancy A Shadick3 & David Reichl, 2.

A statistical software tool, PLINK, specifically developed to test for genetic association, was used to calculate p values for each SNP, enabling identification of a set of candidate SNPs that showed statistically significant association to Endometriosis. All members in the study (cases and controls), were collected from the same geographical region, with participants from different ethnic groups being analyzed separately.

Scanning the Entire Genome

The Affymetrix GeneChip 6.0 mapping array was used to scan the whole genome. Briefly, 250 ng of genomic DNA was digested with either NspI or StyI restriction endonuclease and digested fragments were ligated to adapters that contained a universal sequence. The ligated products were then amplified using the polymerase chain reaction (PCR) to amplify fragments between 250-2000 bp in length. The PCR products were purified and diluted to a standard concentration. Furthermore, the PCR products were then fragmented with a DNase enzyme to approximately 25-150 bp in length. This fragmentation process further reduced the complexity of the genomic sample. The fragmented PCR products were then labeled with a biotin/streptavidin system and allowed to hybridize to the microarray. After hybridization the arrays were stained and non-specific binding was removed through a series of increasingly stringent washes. The genotypes were determined by fluorescent signal detection in an Affymetrix GCS 3000 scanner. Finally, genotypes were called using the BIRDSEED algorithm which is integrated into Affymetrix PowerTool software.

Selection of SNPs for Quality and Association

A SNP is a DNA sequence variation, occurring when a single nucleotide—adenine (A), thymine (T), cytosine (C) or guanine (G)—in the genome differs between individuals. A variation must occur in at least 1% of the population to be considered a SNP. Variations that occur in less than 1% of the population are, by definition considered to be mutations whether they cause disease or not. SNPs make up 90% of all human genetic variations, and occur every 300 to 1000 bases along the human genome. On average, two of every three SNPs substitute cytosine (C) with thymine (T). For the data to be considered valid for an individual chip, two internal quality control measures were used: SNP genotypes must have exceeded an overall call rate of >93% and any SNP that did not have at least a 96% call rate across all subjects was eliminated as having possible genotyping errors. SNPs that were monomorphic, having less than 1% apparent variation in both cases and controls, were also eliminated from analysis. In addition, SNPs that failed a Hardy-Weinberg equilibrium test in the control population only, using a p-value threshold of 0.001, were also eliminated. After filtering, about 640,000 SNPs were available for analysis. Genotypes were analyzed for significance using PLINK and LD blocks were identified using Haploview 4.1 software using the HapMap dataset release 22 as a reference.

GeneChip microarrays consist of small DNA fragments (referred to as probes), chemically synthesized at specific locations on a coated quartz surface. The precise location where each probe is synthesized is called a feature, and millions of features can be contained on one array. The probes which represent a sequence known to contain a human SNP were selected by Affymetrix based on reliability, sensitivity and specificity. In addition to these criteria, the probes were selected to cover the human genome at approximately equal intervals.

Identification of Endometriosis Affected Individuals

Individuals were determined to have endometriosis after medical record review by a single physician. In this study, only patients with visually confirmed disease (either by laparoscopy or other surgical intervention) were included as cases. The controls included individuals without prior history of endometriosis.

Endometriosis Associated SNPs

After sorting all remaining candidate SNPs by p-value, 663 SNPs with p-values less than or equal to 0.001 were selected as Primary SNPs.

Linkage Disequilibrium Blocks

As described above, the human genome includes extensive regions of linkage disequilibrium that undergo very minimal recombination. As a result, any SNP located within the same LD blocks as any of the primary SNPs listed in Table 1 contributes haplotype information for refined diagnostic discrimination and to the further identification of the causative mutation. Therefore, by virtue of linkage disequilibrium, a set of additional SNPs that have been determined to be in linkage disequilibrium with any of the primary SNPs are listed in Tables 2-528. Specifically, by using the Haploview software package in conjunction with the Caucasian population of the HapMap data set (release 22) LD blocks were identified around all SNPs listed in Table 1. Each of the Tables 2-528 represent SNPs located within the LD block(s) surrounding all SNPs from Table 1.

Tables

Lengthy table referenced here

US11287425-20220329-T00001

Please refer to the end of the specification for access instructions.

Lengthy table referenced here

US11287425-20220329-T00002

Please refer to the end of the specification for access instructions.

Lengthy table referenced here

US11287425-20220329-T00003

Please refer to the end of the specification for access instructions.

Lengthy table referenced here

US11287425-20220329-T00004

Please refer to the end of the specification for access instructions.

Lengthy table referenced here

US11287425-20220329-T00005

Please refer to the end of the specification for access instructions.

Lengthy table referenced here

US11287425-20220329-T00006

Please refer to the end of the specification for access instructions.

Lengthy table referenced here

US11287425-20220329-T00007

Please refer to the end of the specification for access instructions.

Lengthy table referenced here
US11287425-20220329-T00008
Please refer to the end of the specification for access instructions.

Lengthy table referenced here
US11287425-20220329-T00009
Please refer to the end of the specification for access instructions.

Lengthy table referenced here
US11287425-20220329-T00010
Please refer to the end of the specification for access instructions.

Lengthy table referenced here
US11287425-20220329-T00011
Please refer to the end of the specification for access instructions.

Lengthy table referenced here
US11287425-20220329-T00012
Please refer to the end of the specification for access instructions.

Lengthy table referenced here
US11287425-20220329-T00013
Please refer to the end of the specification for access instructions.

Lengthy table referenced here
US11287425-20220329-T00014
Please refer to the end of the specification for access instructions.

Lengthy table referenced here
US11287425-20220329-T00015
Please refer to the end of the specification for access instructions.

Lengthy table referenced here
US11287425-20220329-T00016
Please refer to the end of the specification for access instructions.

Lengthy table referenced here
US11287425-20220329-T00017
Please refer to the end of the specification for access instructions.

Lengthy table referenced here
US11287425-20220329-T00018
Please refer to the end of the specification for access instructions.

Lengthy table referenced here
US11287425-20220329-T00019
Please refer to the end of the specification for access instructions.

Lengthy table referenced here
US11287425-20220329-T00020
Please refer to the end of the specification for access instructions.

Lengthy table referenced here
US11287425-20220329-T00021
Please refer to the end of the specification for access instructions.

Lengthy table referenced here
US11287425-20220329-T00022
Please refer to the end of the specification for access instructions.

Lengthy table referenced here
US11287425-20220329-T00023
Please refer to the end of the specification for access instructions.

Lengthy table referenced here
US11287425-20220329-T00024
Please refer to the end of the specification for access instructions.

Lengthy table referenced here
US11287425-20220329-T00025
Please refer to the end of the specification for access instructions.

Lengthy table referenced here
US11287425-20220329-T00026
Please refer to the end of the specification for access instructions.

Lengthy table referenced here
US11287425-20220329-T00027
Please refer to the end of the specification for access instructions.

Lengthy table referenced here
US11287425-20220329-T00028
Please refer to the end of the specification for access instructions.

Lengthy table referenced here
US11287425-20220329-T00029
Please refer to the end of the specification for access instructions.

Lengthy table referenced here
US11287425-20220329-T00030
Please refer to the end of the specification for access instructions.

Lengthy table referenced here
US11287425-20220329-T00031
Please refer to the end of the specification for access instructions.

Lengthy table referenced here
US11287425-20220329-T00032
Please refer to the end of the specification for access instructions.

Lengthy table referenced here
US11287425-20220329-T00033
Please refer to the end of the specification for access instructions.

Lengthy table referenced here
US11287425-20220329-T00034
Please refer to the end of the specification for access instructions.

Lengthy table referenced here
US11287425-20220329-T00035
Please refer to the end of the specification for access instructions.

Lengthy table referenced here
US11287425-20220329-T00036
Please refer to the end of the specification for access instructions.

Lengthy table referenced here
US11287425-20220329-T00037
Please refer to the end of the specification for access instructions.

Lengthy table referenced here
US11287425-20220329-T00038
Please refer to the end of the specification for access instructions.

Lengthy table referenced here
US11287425-20220329-T00039
Please refer to the end of the specification for access instructions.

Lengthy table referenced here
US11287425-20220329-T00040
Please refer to the end of the specification for access instructions.

Lengthy table referenced here
US11287425-20220329-T00041
Please refer to the end of the specification for access instructions.

Lengthy table referenced here
US11287425-20220329-T00042
Please refer to the end of the specification for access instructions.

Lengthy table referenced here
US11287425-20220329-T00043
Please refer to the end of the specification for access instructions.

Lengthy table referenced here
US11287425-20220329-T00044
Please refer to the end of the specification for access instructions.

Lengthy table referenced here
US11287425-20220329-T00045
Please refer to the end of the specification for access instructions.

Lengthy table referenced here
US11287425-20220329-T00046
Please refer to the end of the specification for access instructions.

Lengthy table referenced here
US11287425-20220329-T00047
Please refer to the end of the specification for access instructions.

Lengthy table referenced here
US11287425-20220329-T00048
Please refer to the end of the specification for access instructions.

Lengthy table referenced here
US11287425-20220329-T00049
Please refer to the end of the specification for access instructions.

Lengthy table referenced here
US11287425-20220329-T00050
Please refer to the end of the specification for access instructions.

Lengthy table referenced here
US11287425-20220329-T00051
Please refer to the end of the specification for access instructions.

Lengthy table referenced here
US11287425-20220329-T00052
Please refer to the end of the specification for access instructions.

Lengthy table referenced here
US11287425-20220329-T00053
Please refer to the end of the specification for access instructions.

Lengthy table referenced here
US11287425-20220329-T00054
Please refer to the end of the specification for access instructions.

Lengthy table referenced here
US11287425-20220329-T00055
Please refer to the end of the specification for access instructions.

Lengthy table referenced here
US11287425-20220329-T00056
Please refer to the end of the specification for access instructions.

Lengthy table referenced here
US11287425-20220329-T00057
Please refer to the end of the specification for access instructions.

Lengthy table referenced here
US11287425-20220329-T00058
Please refer to the end of the specification for access instructions.

Lengthy table referenced here
US11287425-20220329-T00059
Please refer to the end of the specification for access instructions.

Lengthy table referenced here
US11287425-20220329-T00060
Please refer to the end of the specification for access instructions.

Lengthy table referenced here
US11287425-20220329-T00061
Please refer to the end of the specification for access instructions.

Lengthy table referenced here
US11287425-20220329-T00062
Please refer to the end of the specification for access instructions.

Lengthy table referenced here
US11287425-20220329-T00063
Please refer to the end of the specification for access instructions.

Lengthy table referenced here
US11287425-20220329-T00064
Please refer to the end of the specification for access instructions.

Lengthy table referenced here
US11287425-20220329-T00065
Please refer to the end of the specification for access instructions.

Lengthy table referenced here
US11287425-20220329-T00066
Please refer to the end of the specification for access instructions.

Lengthy table referenced here
US11287425-20220329-T00067
Please refer to the end of the specification for access instructions.

Lengthy table referenced here
US11287425-20220329-T00068
Please refer to the end of the specification for access instructions.

Lengthy table referenced here
US11287425-20220329-T00069
Please refer to the end of the specification for access instructions.

Lengthy table referenced here
US11287425-20220329-T00070
Please refer to the end of the specification for access instructions.

Lengthy table referenced here
US11287425-20220329-T00071
Please refer to the end of the specification for access instructions.

Lengthy table referenced here
US11287425-20220329-T00072
Please refer to the end of the specification for access instructions.

Lengthy table referenced here
US11287425-20220329-T00073
Please refer to the end of the specification for access instructions.

Lengthy table referenced here
US11287425-20220329-T00074
Please refer to the end of the specification for access instructions.

Lengthy table referenced here
US11287425-20220329-T00075
Please refer to the end of the specification for access instructions.

Lengthy table referenced here
US11287425-20220329-T00076
Please refer to the end of the specification for access instructions.

Lengthy table referenced here
US11287425-20220329-T00077
Please refer to the end of the specification for access instructions.

Lengthy table referenced here
US11287425-20220329-T00078
Please refer to the end of the specification for access instructions.

Lengthy table referenced here
US11287425-20220329-T00079
Please refer to the end of the specification for access instructions.

Lengthy table referenced here
US11287425-20220329-T00080
Please refer to the end of the specification for access instructions.

Lengthy table referenced here
US11287425-20220329-T00081
Please refer to the end of the specification for access instructions.

Lengthy table referenced here
US11287425-20220329-T00082
Please refer to the end of the specification for access instructions.

Lengthy table referenced here
US11287425-20220329-T00083
Please refer to the end of the specification for access instructions.

Lengthy table referenced here
US11287425-20220329-T00084
Please refer to the end of the specification for access instructions.

Lengthy table referenced here
US11287425-20220329-T00085
Please refer to the end of the specification for access instructions.

Lengthy table referenced here
US11287425-20220329-T00086
Please refer to the end of the specification for access instructions.

Lengthy table referenced here
US11287425-20220329-T00087
Please refer to the end of the specification for access instructions.

Lengthy table referenced here
US11287425-20220329-T00088
Please refer to the end of the specification for access instructions.

Lengthy table referenced here
US11287425-20220329-T00089
Please refer to the end of the specification for access instructions.

Lengthy table referenced here
US11287425-20220329-T00090
Please refer to the end of the specification for access instructions.

Lengthy table referenced here
US11287425-20220329-T00091
Please refer to the end of the specification for access instructions.

Lengthy table referenced here
US11287425-20220329-T00092
Please refer to the end of the specification for access instructions.

Lengthy table referenced here
US11287425-20220329-T00093
Please refer to the end of the specification for access instructions.

Lengthy table referenced here
US11287425-20220329-T00094
Please refer to the end of the specification for access instructions.

Lengthy table referenced here
US11287425-20220329-T00095
Please refer to the end of the specification for access instructions.

Lengthy table referenced here
US11287425-20220329-T00096
Please refer to the end of the specification for access instructions.

Lengthy table referenced here
US11287425-20220329-T00097
Please refer to the end of the specification for access instructions.

Lengthy table referenced here
US11287425-20220329-T00098
Please refer to the end of the specification for access instructions.

Lengthy table referenced here
US11287425-20220329-T00099
Please refer to the end of the specification for access instructions.

Lengthy table referenced here
US11287425-20220329-T00100
Please refer to the end of the specification for access instructions.

Lengthy table referenced here
US11287425-20220329-T00101
Please refer to the end of the specification for access instructions.

Lengthy table referenced here
US11287425-20220329-T00102
Please refer to the end of the specification for access instructions.

Lengthy table referenced here
US11287425-20220329-T00103
Please refer to the end of the specification for access instructions.

Lengthy table referenced here
US11287425-20220329-T00104
Please refer to the end of the specification for access instructions.

Lengthy table referenced here
US11287425-20220329-T00105
Please refer to the end of the specification for access instructions.

Lengthy table referenced here
US11287425-20220329-T00106
Please refer to the end of the specification for access instructions.

Lengthy table referenced here
US11287425-20220329-T00107
Please refer to the end of the specification for access instructions.

Lengthy table referenced here
US11287425-20220329-T00108
Please refer to the end of the specification for access instructions.

Lengthy table referenced here
US11287425-20220329-T00109
Please refer to the end of the specification for access instructions.

Lengthy table referenced here
US11287425-20220329-T00110
Please refer to the end of the specification for access instructions.

Lengthy table referenced here
US11287425-20220329-T00111
Please refer to the end of the specification for access instructions.

Lengthy table referenced here
US11287425-20220329-T00112
Please refer to the end of the specification for access instructions.

Lengthy table referenced here
US11287425-20220329-T00113
Please refer to the end of the specification for access instructions.

Lengthy table referenced here
US11287425-20220329-T00114
Please refer to the end of the specification for access instructions.

Lengthy table referenced here
US11287425-20220329-T00115
Please refer to the end of the specification for access instructions.

Lengthy table referenced here
US11287425-20220329-T00116
Please refer to the end of the specification for access instructions.

Lengthy table referenced here
US11287425-20220329-T00117
Please refer to the end of the specification for access instructions.

Lengthy table referenced here
US11287425-20220329-T00118
Please refer to the end of the specification for access instructions.

Lengthy table referenced here
US11287425-20220329-T00119
Please refer to the end of the specification for access instructions.

Lengthy table referenced here
US11287425-20220329-T00120
Please refer to the end of the specification for access instructions.

Lengthy table referenced here
US11287425-20220329-T00121
Please refer to the end of the specification for access instructions.

Lengthy table referenced here
US11287425-20220329-T00122
Please refer to the end of the specification for access instructions.

Lengthy table referenced here
US11287425-20220329-T00123
Please refer to the end of the specification for access instructions.

Lengthy table referenced here
US11287425-20220329-T00124
Please refer to the end of the specification for access instructions.

Lengthy table referenced here
US11287425-20220329-T00125
Please refer to the end of the specification for access instructions.

Lengthy table referenced here
US11287425-20220329-T00126
Please refer to the end of the specification for access instructions.

Lengthy table referenced here
US11287425-20220329-T00127
Please refer to the end of the specification for access instructions.

Lengthy table referenced here
US11287425-20220329-T00128
Please refer to the end of the specification for access instructions.

Lengthy table referenced here
US11287425-20220329-T00129
Please refer to the end of the specification for access instructions.

Lengthy table referenced here
US11287425-20220329-T00130
Please refer to the end of the specification for access instructions.

Lengthy table referenced here
US11287425-20220329-T00131
Please refer to the end of the specification for access instructions.

Lengthy table referenced here
US11287425-20220329-T00132
Please refer to the end of the specification for access instructions.

Lengthy table referenced here
US11287425-20220329-T00133
Please refer to the end of the specification for access instructions.

Lengthy table referenced here
US11287425-20220329-T00134
Please refer to the end of the specification for access instructions.

Lengthy table referenced here
US11287425-20220329-T00135
Please refer to the end of the specification for access instructions.

Lengthy table referenced here
US11287425-20220329-T00136
Please refer to the end of the specification for access instructions.

Lengthy table referenced here
US11287425-20220329-T00137
Please refer to the end of the specification for access instructions.

Lengthy table referenced here
US11287425-20220329-T00138
Please refer to the end of the specification for access instructions.

Lengthy table referenced here
US11287425-20220329-T00139
Please refer to the end of the specification for access instructions.

Lengthy table referenced here
US11287425-20220329-T00140
Please refer to the end of the specification for access instructions.

Lengthy table referenced here
US11287425-20220329-T00141
Please refer to the end of the specification for access instructions.

Lengthy table referenced here
US11287425-20220329-T00142
Please refer to the end of the specification for access instructions.

Lengthy table referenced here
US11287425-20220329-T00143
Please refer to the end of the specification for access instructions.

Lengthy table referenced here
US11287425-20220329-T00144
Please refer to the end of the specification for access instructions.

Lengthy table referenced here
US11287425-20220329-T00145
Please refer to the end of the specification for access instructions.

Lengthy table referenced here
US11287425-20220329-T00146
Please refer to the end of the specification for access instructions.

Lengthy table referenced here
US11287425-20220329-T00147
Please refer to the end of the specification for access instructions.

Lengthy table referenced here
US11287425-20220329-T00148
Please refer to the end of the specification for access instructions.

Lengthy table referenced here
US11287425-20220329-T00149
Please refer to the end of the specification for access instructions.

Lengthy table referenced here
US11287425-20220329-T00150
Please refer to the end of the specification for access instructions.

Lengthy table referenced here
US11287425-20220329-T00151
Please refer to the end of the specification for access instructions.

Lengthy table referenced here
US11287425-20220329-T00152
Please refer to the end of the specification for access instructions.

Lengthy table referenced here
US11287425-20220329-T00153
Please refer to the end of the specification for access instructions.

Lengthy table referenced here
US11287425-20220329-T00154
Please refer to the end of the specification for access instructions.

Lengthy table referenced here
US11287425-20220329-T00155
Please refer to the end of the specification for access instructions.

Lengthy table referenced here
US11287425-20220329-T00156
Please refer to the end of the specification for access instructions.

Lengthy table referenced here
US11287425-20220329-T00157
Please refer to the end of the specification for access instructions.

Lengthy table referenced here
US11287425-20220329-T00158
Please refer to the end of the specification for access instructions.

Lengthy table referenced here
US11287425-20220329-T00159
Please refer to the end of the specification for access instructions.

Lengthy table referenced here
US11287425-20220329-T00160
Please refer to the end of the specification for access instructions.

Lengthy table referenced here
US11287425-20220329-T00161
Please refer to the end of the specification for access instructions.

Lengthy table referenced here
US11287425-20220329-T00162
Please refer to the end of the specification for access instructions.

Lengthy table referenced here
US11287425-20220329-T00163
Please refer to the end of the specification for access instructions.

Lengthy table referenced here
US11287425-20220329-T00164
Please refer to the end of the specification for access instructions.

Lengthy table referenced here
US11287425-20220329-T00165
Please refer to the end of the specification for access instructions.

Lengthy table referenced here
US11287425-20220329-T00166
Please refer to the end of the specification for access instructions.

Lengthy table referenced here
US11287425-20220329-T00167
Please refer to the end of the specification for access instructions.

Lengthy table referenced here
US11287425-20220329-T00168
Please refer to the end of the specification for access instructions.

Lengthy table referenced here
US11287425-20220329-T00169
Please refer to the end of the specification for access instructions.

Lengthy table referenced here
US11287425-20220329-T00170
Please refer to the end of the specification for access instructions.

Lengthy table referenced here
US11287425-20220329-T00171
Please refer to the end of the specification for access instructions.

Lengthy table referenced here
US11287425-20220329-T00172
Please refer to the end of the specification for access instructions.

Lengthy table referenced here
US11287425-20220329-T00173
Please refer to the end of the specification for access instructions.

Lengthy table referenced here
US11287425-20220329-T00174
Please refer to the end of the specification for access instructions.

Lengthy table referenced here
US11287425-20220329-T00175
Please refer to the end of the specification for access instructions.

Lengthy table referenced here
US11287425-20220329-T00176
Please refer to the end of the specification for access instructions.

Lengthy table referenced here
US11287425-20220329-T00177
Please refer to the end of the specification for access instructions.

Lengthy table referenced here
US11287425-20220329-T00178
Please refer to the end of the specification for access instructions.

Lengthy table referenced here
US11287425-20220329-T00179
Please refer to the end of the specification for access instructions.

Lengthy table referenced here
US11287425-20220329-T00180
Please refer to the end of the specification for access instructions.

Lengthy table referenced here
US11287425-20220329-T00181
Please refer to the end of the specification for access instructions.

Lengthy table referenced here
US11287425-20220329-T00182
Please refer to the end of the specification for access instructions.

Lengthy table referenced here
US11287425-20220329-T00183
Please refer to the end of the specification for access instructions.

Lengthy table referenced here
US11287425-20220329-T00184
Please refer to the end of the specification for access instructions.

Lengthy table referenced here
US11287425-20220329-T00185
Please refer to the end of the specification for access instructions.

Lengthy table referenced here
US11287425-20220329-T00186
Please refer to the end of the specification for access instructions.

Lengthy table referenced here
US11287425-20220329-T00187
Please refer to the end of the specification for access instructions.

Lengthy table referenced here
US11287425-20220329-T00188
Please refer to the end of the specification for access instructions.

Lengthy table referenced here
US11287425-20220329-T00189
Please refer to the end of the specification for access instructions.

Lengthy table referenced here
US11287425-20220329-T00190
Please refer to the end of the specification for access instructions.

Lengthy table referenced here
US11287425-20220329-T00191
Please refer to the end of the specification for access instructions.

Lengthy table referenced here
US11287425-20220329-T00192
Please refer to the end of the specification for access instructions.

Lengthy table referenced here
US11287425-20220329-T00193
Please refer to the end of the specification for access instructions.

Lengthy table referenced here
US11287425-20220329-T00194
Please refer to the end of the specification for access instructions.

Lengthy table referenced here
US11287425-20220329-T00195
Please refer to the end of the specification for access instructions.

Lengthy table referenced here
US11287425-20220329-T00196
Please refer to the end of the specification for access instructions.

Lengthy table referenced here
US11287425-20220329-T00197
Please refer to the end of the specification for access instructions.

Lengthy table referenced here
US11287425-20220329-T00198
Please refer to the end of the specification for access instructions.

Lengthy table referenced here
US11287425-20220329-T00199
Please refer to the end of the specification for access instructions.

Lengthy table referenced here
US11287425-20220329-T00200
Please refer to the end of the specification for access instructions.

Lengthy table referenced here
US11287425-20220329-T00201
Please refer to the end of the specification for access instructions.

Lengthy table referenced here
US11287425-20220329-T00202
Please refer to the end of the specification for access instructions.

Lengthy table referenced here
US11287425-20220329-T00203
Please refer to the end of the specification for access instructions.

Lengthy table referenced here
US11287425-20220329-T00204
Please refer to the end of the specification for access instructions.

Lengthy table referenced here
US11287425-20220329-T00205
Please refer to the end of the specification for access instructions.

Lengthy table referenced here
US11287425-20220329-T00206
Please refer to the end of the specification for access instructions.

Lengthy table referenced here
US11287425-20220329-T00207
Please refer to the end of the specification for access instructions.

Lengthy table referenced here
US11287425-20220329-T00208
Please refer to the end of the specification for access instructions.

Lengthy table referenced here
US11287425-20220329-T00209
Please refer to the end of the specification for access instructions.

Lengthy table referenced here
US11287425-20220329-T00210
Please refer to the end of the specification for access instructions.

Lengthy table referenced here
US11287425-20220329-T00211
Please refer to the end of the specification for access instructions.

Lengthy table referenced here
US11287425-20220329-T00212
Please refer to the end of the specification for access instructions.

Lengthy table referenced here
US11287425-20220329-T00213
Please refer to the end of the specification for access instructions.

Lengthy table referenced here
US11287425-20220329-T00214
Please refer to the end of the specification for access instructions.

Lengthy table referenced here
US11287425-20220329-T00215
Please refer to the end of the specification for access instructions.

Lengthy table referenced here
US11287425-20220329-T00216
Please refer to the end of the specification for access instructions.

Lengthy table referenced here
US11287425-20220329-T00217
Please refer to the end of the specification for access instructions.

Lengthy table referenced here
US11287425-20220329-T00218
Please refer to the end of the specification for access instructions.

Lengthy table referenced here
US11287425-20220329-T00219
Please refer to the end of the specification for access instructions.

Lengthy table referenced here
US11287425-20220329-T00220
Please refer to the end of the specification for access instructions.

Lengthy table referenced here
US11287425-20220329-T00221
Please refer to the end of the specification for access instructions.

Lengthy table referenced here
US11287425-20220329-T00222
Please refer to the end of the specification for access instructions.

Lengthy table referenced here
US11287425-20220329-T00223
Please refer to the end of the specification for access instructions.

Lengthy table referenced here
US11287425-20220329-T00224
Please refer to the end of the specification for access instructions.

Lengthy table referenced here
US11287425-20220329-T00225
Please refer to the end of the specification for access instructions.

Lengthy table referenced here
US11287425-20220329-T00226
Please refer to the end of the specification for access instructions.

Lengthy table referenced here
US11287425-20220329-T00227
Please refer to the end of the specification for access instructions.

Lengthy table referenced here
US11287425-20220329-T00228
Please refer to the end of the specification for access instructions.

Lengthy table referenced here
US11287425-20220329-T00229
Please refer to the end of the specification for access instructions.

Lengthy table referenced here
US11287425-20220329-T00230
Please refer to the end of the specification for access instructions.

Lengthy table referenced here
US11287425-20220329-T00231
Please refer to the end of the specification for access instructions.

Lengthy table referenced here
US11287425-20220329-T00232
Please refer to the end of the specification for access instructions.

Lengthy table referenced here
US11287425-20220329-T00233
Please refer to the end of the specification for access instructions.

Lengthy table referenced here
US11287425-20220329-T00234
Please refer to the end of the specification for access instructions.

Lengthy table referenced here
US11287425-20220329-T00235
Please refer to the end of the specification for access instructions.

Lengthy table referenced here
US11287425-20220329-T00236
Please refer to the end of the specification for access instructions.

Lengthy table referenced here
US11287425-20220329-T00237
Please refer to the end of the specification for access instructions.

Lengthy table referenced here
US11287425-20220329-T00238
Please refer to the end of the specification for access instructions.

Lengthy table referenced here
US11287425-20220329-T00239
Please refer to the end of the specification for access instructions.

Lengthy table referenced here
US11287425-20220329-T00240
Please refer to the end of the specification for access instructions.

Lengthy table referenced here
US11287425-20220329-T00241
Please refer to the end of the specification for access instructions.

Lengthy table referenced here
US11287425-20220329-T00242
Please refer to the end of the specification for access instructions.

Lengthy table referenced here
US11287425-20220329-T00243
Please refer to the end of the specification for access instructions.

Lengthy table referenced here
US11287425-20220329-T00244
Please refer to the end of the specification for access instructions.

Lengthy table referenced here
US11287425-20220329-T00245
Please refer to the end of the specification for access instructions.

Lengthy table referenced here
US11287425-20220329-T00246
Please refer to the end of the specification for access instructions.

Lengthy table referenced here
US11287425-20220329-T00247
Please refer to the end of the specification for access instructions.

Lengthy table referenced here
US11287425-20220329-T00248
Please refer to the end of the specification for access instructions.

Lengthy table referenced here
US11287425-20220329-T00249
Please refer to the end of the specification for access instructions.

Lengthy table referenced here
US11287425-20220329-T00250
Please refer to the end of the specification for access instructions.

Lengthy table referenced here
US11287425-20220329-T00251
Please refer to the end of the specification for access instructions.

Lengthy table referenced here
US11287425-20220329-T00252
Please refer to the end of the specification for access instructions.

Lengthy table referenced here
US11287425-20220329-T00253
Please refer to the end of the specification for access instructions.

Lengthy table referenced here
US11287425-20220329-T00254
Please refer to the end of the specification for access instructions.

Lengthy table referenced here
US11287425-20220329-T00255
Please refer to the end of the specification for access instructions.

Lengthy table referenced here
US11287425-20220329-T00256
Please refer to the end of the specification for access instructions.

Lengthy table referenced here
US11287425-20220329-T00257
Please refer to the end of the specification for access instructions.

Lengthy table referenced here
US11287425-20220329-T00258
Please refer to the end of the specification for access instructions.

Lengthy table referenced here
US11287425-20220329-T00259
Please refer to the end of the specification for access instructions.

Lengthy table referenced here
US11287425-20220329-T00260
Please refer to the end of the specification for access instructions.

Lengthy table referenced here
US11287425-20220329-T00261
Please refer to the end of the specification for access instructions.

Lengthy table referenced here
US11287425-20220329-T00262
Please refer to the end of the specification for access instructions.

Lengthy table referenced here
US11287425-20220329-T00263
Please refer to the end of the specification for access instructions.

Lengthy table referenced here
US11287425-20220329-T00264
Please refer to the end of the specification for access instructions.

Lengthy table referenced here
US11287425-20220329-T00265
Please refer to the end of the specification for access instructions.

Lengthy table referenced here
US11287425-20220329-T00266
Please refer to the end of the specification for access instructions.

Lengthy table referenced here
US11287425-20220329-T00267
Please refer to the end of the specification for access instructions.

Lengthy table referenced here
US11287425-20220329-T00268
Please refer to the end of the specification for access instructions.

Lengthy table referenced here
US11287425-20220329-T00269
Please refer to the end of the specification for access instructions.

Lengthy table referenced here
US11287425-20220329-T00270
Please refer to the end of the specification for access instructions.

Lengthy table referenced here
US11287425-20220329-T00271
Please refer to the end of the specification for access instructions.

Lengthy table referenced here
US11287425-20220329-T00272
Please refer to the end of the specification for access instructions.

Lengthy table referenced here
US11287425-20220329-T00273
Please refer to the end of the specification for access instructions.

Lengthy table referenced here
US11287425-20220329-T00274
Please refer to the end of the specification for access instructions.

Lengthy table referenced here
US11287425-20220329-T00275
Please refer to the end of the specification for access instructions.

Lengthy table referenced here
US11287425-20220329-T00276
Please refer to the end of the specification for access instructions.

Lengthy table referenced here
US11287425-20220329-T00277
Please refer to the end of the specification for access instructions.

Lengthy table referenced here
US11287425-20220329-T00278
Please refer to the end of the specification for access instructions.

Lengthy table referenced here
US11287425-20220329-T00279
Please refer to the end of the specification for access instructions.

Lengthy table referenced here
US11287425-20220329-T00280
Please refer to the end of the specification for access instructions.

Lengthy table referenced here
US11287425-20220329-T00281
Please refer to the end of the specification for access instructions.

Lengthy table referenced here
US11287425-20220329-T00282
Please refer to the end of the specification for access instructions.

Lengthy table referenced here
US11287425-20220329-T00283
Please refer to the end of the specification for access instructions.

Lengthy table referenced here
US11287425-20220329-T00284
Please refer to the end of the specification for access instructions.

Lengthy table referenced here
US11287425-20220329-T00285
Please refer to the end of the specification for access instructions.

Lengthy table referenced here
US11287425-20220329-T00286
Please refer to the end of the specification for access instructions.

Lengthy table referenced here
US11287425-20220329-T00287
Please refer to the end of the specification for access instructions.

Lengthy table referenced here
US11287425-20220329-T00288
Please refer to the end of the specification for access instructions.

Lengthy table referenced here
US11287425-20220329-T00289
Please refer to the end of the specification for access instructions.

Lengthy table referenced here
US11287425-20220329-T00290
Please refer to the end of the specification for access instructions.

Lengthy table referenced here
US11287425-20220329-T00291
Please refer to the end of the specification for access instructions.

Lengthy table referenced here
US11287425-20220329-T00292
Please refer to the end of the specification for access instructions.

Lengthy table referenced here
US11287425-20220329-T00293
Please refer to the end of the specification for access instructions.

Lengthy table referenced here
US11287425-20220329-T00294
Please refer to the end of the specification for access instructions.

Lengthy table referenced here
US11287425-20220329-T00295
Please refer to the end of the specification for access instructions.

Lengthy table referenced here
US11287425-20220329-T00296
Please refer to the end of the specification for access instructions.

Lengthy table referenced here
US11287425-20220329-T00297
Please refer to the end of the specification for access instructions.

Lengthy table referenced here
US11287425-20220329-T00298
Please refer to the end of the specification for access instructions.

Lengthy table referenced here
US11287425-20220329-T00299
Please refer to the end of the specification for access instructions.

Lengthy table referenced here
US11287425-20220329-T00300
Please refer to the end of the specification for access instructions.

Lengthy table referenced here
US11287425-20220329-T00301
Please refer to the end of the specification for access instructions.

Lengthy table referenced here
US11287425-20220329-T00302
Please refer to the end of the specification for access instructions.

Lengthy table referenced here
US11287425-20220329-T00303
Please refer to the end of the specification for access instructions.

Lengthy table referenced here
US11287425-20220329-T00304
Please refer to the end of the specification for access instructions.

Lengthy table referenced here
US11287425-20220329-T00305
Please refer to the end of the specification for access instructions.

Lengthy table referenced here
US11287425-20220329-T00306
Please refer to the end of the specification for access instructions.

Lengthy table referenced here
US11287425-20220329-T00307
Please refer to the end of the specification for access instructions.

Lengthy table referenced here
US11287425-20220329-T00308
Please refer to the end of the specification for access instructions.

Lengthy table referenced here
US11287425-20220329-T00309
Please refer to the end of the specification for access instructions.

Lengthy table referenced here
US11287425-20220329-T00310
Please refer to the end of the specification for access instructions.

Lengthy table referenced here
US11287425-20220329-T00311
Please refer to the end of the specification for access instructions.

Lengthy table referenced here
US11287425-20220329-T00312
Please refer to the end of the specification for access instructions.

Lengthy table referenced here
US11287425-20220329-T00313
Please refer to the end of the specification for access instructions.

Lengthy table referenced here
US11287425-20220329-T00314
Please refer to the end of the specification for access instructions.

Lengthy table referenced here
US11287425-20220329-T00315
Please refer to the end of the specification for access instructions.

Lengthy table referenced here
US11287425-20220329-T00316
Please refer to the end of the specification for access instructions.

Lengthy table referenced here
US11287425-20220329-T00317
Please refer to the end of the specification for access instructions.

Lengthy table referenced here
US11287425-20220329-T00318
Please refer to the end of the specification for access instructions.

Lengthy table referenced here
US11287425-20220329-T00319
Please refer to the end of the specification for access instructions.

Lengthy table referenced here
US11287425-20220329-T00320
Please refer to the end of the specification for access instructions.

Lengthy table referenced here
US11287425-20220329-T00321
Please refer to the end of the specification for access instructions.

Lengthy table referenced here
US11287425-20220329-T00322
Please refer to the end of the specification for access instructions.

Lengthy table referenced here
US11287425-20220329-T00323
Please refer to the end of the specification for access instructions.

Lengthy table referenced here
US11287425-20220329-T00324
Please refer to the end of the specification for access instructions.

Lengthy table referenced here
US11287425-20220329-T00325
Please refer to the end of the specification for access instructions.

Lengthy table referenced here
US11287425-20220329-T00326
Please refer to the end of the specification for access instructions.

Lengthy table referenced here
US11287425-20220329-T00327
Please refer to the end of the specification for access instructions.

Lengthy table referenced here
US11287425-20220329-T00328
Please refer to the end of the specification for access instructions.

Lengthy table referenced here
US11287425-20220329-T00329
Please refer to the end of the specification for access instructions.

Lengthy table referenced here
US11287425-20220329-T00330
Please refer to the end of the specification for access instructions.

Lengthy table referenced here
US11287425-20220329-T00331
Please refer to the end of the specification for access instructions.

Lengthy table referenced here
US11287425-20220329-T00332
Please refer to the end of the specification for access instructions.

Lengthy table referenced here
US11287425-20220329-T00333
Please refer to the end of the specification for access instructions.

Lengthy table referenced here
US11287425-20220329-T00334
Please refer to the end of the specification for access instructions.

Lengthy table referenced here
US11287425-20220329-T00335
Please refer to the end of the specification for access instructions.

Lengthy table referenced here
US11287425-20220329-T00336
Please refer to the end of the specification for access instructions.

Lengthy table referenced here
US11287425-20220329-T00337
Please refer to the end of the specification for access instructions.

Lengthy table referenced here
US11287425-20220329-T00338
Please refer to the end of the specification for access instructions.

Lengthy table referenced here
US11287425-20220329-T00339
Please refer to the end of the specification for access instructions.

Lengthy table referenced here
US11287425-20220329-T00340
Please refer to the end of the specification for access instructions.

Lengthy table referenced here
US11287425-20220329-T00341
Please refer to the end of the specification for access instructions.

Lengthy table referenced here
US11287425-20220329-T00342
Please refer to the end of the specification for access instructions.

Lengthy table referenced here
US11287425-20220329-T00343
Please refer to the end of the specification for access instructions.

Lengthy table referenced here
US11287425-20220329-T00344
Please refer to the end of the specification for access instructions.

Lengthy table referenced here
US11287425-20220329-T00345
Please refer to the end of the specification for access instructions.

Lengthy table referenced here
US11287425-20220329-T00346
Please refer to the end of the specification for access instructions.

Lengthy table referenced here
US11287425-20220329-T00347
Please refer to the end of the specification for access instructions.

Lengthy table referenced here
US11287425-20220329-T00348
Please refer to the end of the specification for access instructions.

Lengthy table referenced here
US11287425-20220329-T00349
Please refer to the end of the specification for access instructions.

Lengthy table referenced here
US11287425-20220329-T00350
Please refer to the end of the specification for access instructions.

Lengthy table referenced here
US11287425-20220329-T00351
Please refer to the end of the specification for access instructions.

Lengthy table referenced here
US11287425-20220329-T00352
Please refer to the end of the specification for access instructions.

Lengthy table referenced here
US11287425-20220329-T00353
Please refer to the end of the specification for access instructions.

Lengthy table referenced here
US11287425-20220329-T00354
Please refer to the end of the specification for access instructions.

Lengthy table referenced here
US11287425-20220329-T00355
Please refer to the end of the specification for access instructions.

Lengthy table referenced here
US11287425-20220329-T00356
Please refer to the end of the specification for access instructions.

Lengthy table referenced here
US11287425-20220329-T00357
Please refer to the end of the specification for access instructions.

Lengthy table referenced here
US11287425-20220329-T00358
Please refer to the end of the specification for access instructions.

Lengthy table referenced here
US11287425-20220329-T00359
Please refer to the end of the specification for access instructions.

Lengthy table referenced here
US11287425-20220329-T00360
Please refer to the end of the specification for access instructions.

Lengthy table referenced here
US11287425-20220329-T00361
Please refer to the end of the specification for access instructions.

Lengthy table referenced here
US11287425-20220329-T00362
Please refer to the end of the specification for access instructions.

Lengthy table referenced here
US11287425-20220329-T00363
Please refer to the end of the specification for access instructions.

Lengthy table referenced here
US11287425-20220329-T00364
Please refer to the end of the specification for access instructions.

Lengthy table referenced here
US11287425-20220329-T00365
Please refer to the end of the specification for access instructions.

Lengthy table referenced here
US11287425-20220329-T00366
Please refer to the end of the specification for access instructions.

Lengthy table referenced here
US11287425-20220329-T00367
Please refer to the end of the specification for access instructions.

Lengthy table referenced here
US11287425-20220329-T00368
Please refer to the end of the specification for access instructions.

Lengthy table referenced here
US11287425-20220329-T00369
Please refer to the end of the specification for access instructions.

Lengthy table referenced here
US11287425-20220329-T00370
Please refer to the end of the specification for access instructions.

Lengthy table referenced here
US11287425-20220329-T00371
Please refer to the end of the specification for access instructions.

Lengthy table referenced here
US11287425-20220329-T00372
Please refer to the end of the specification for access instructions.

Lengthy table referenced here
US11287425-20220329-T00373
Please refer to the end of the specification for access instructions.

Lengthy table referenced here
US11287425-20220329-T00374
Please refer to the end of the specification for access instructions.

Lengthy table referenced here
US11287425-20220329-T00375
Please refer to the end of the specification for access instructions.

Lengthy table referenced here
US11287425-20220329-T00376
Please refer to the end of the specification for access instructions.

Lengthy table referenced here
US11287425-20220329-T00377
Please refer to the end of the specification for access instructions.

Lengthy table referenced here
US11287425-20220329-T00378
Please refer to the end of the specification for access instructions.

Lengthy table referenced here
US11287425-20220329-T00379
Please refer to the end of the specification for access instructions.

Lengthy table referenced here
US11287425-20220329-T00380
Please refer to the end of the specification for access instructions.

Lengthy table referenced here
US11287425-20220329-T00381
Please refer to the end of the specification for access instructions.

Lengthy table referenced here
US11287425-20220329-T00382
Please refer to the end of the specification for access instructions.

Lengthy table referenced here
US11287425-20220329-T00383
Please refer to the end of the specification for access instructions.

Lengthy table referenced here
US11287425-20220329-T00384
Please refer to the end of the specification for access instructions.

Lengthy table referenced here
US11287425-20220329-T00385
Please refer to the end of the specification for access instructions.

Lengthy table referenced here
US11287425-20220329-T00386
Please refer to the end of the specification for access instructions.

Lengthy table referenced here
US11287425-20220329-T00387
Please refer to the end of the specification for access instructions.

Lengthy table referenced here
US11287425-20220329-T00388
Please refer to the end of the specification for access instructions.

Lengthy table referenced here
US11287425-20220329-T00389
Please refer to the end of the specification for access instructions.

Lengthy table referenced here
US11287425-20220329-T00390
Please refer to the end of the specification for access instructions.

Lengthy table referenced here
US11287425-20220329-T00391
Please refer to the end of the specification for access instructions.

Lengthy table referenced here
US11287425-20220329-T00392
Please refer to the end of the specification for access instructions.

Lengthy table referenced here
US11287425-20220329-T00393
Please refer to the end of the specification for access instructions.

Lengthy table referenced here
US11287425-20220329-T00394
Please refer to the end of the specification for access instructions.

Lengthy table referenced here
US11287425-20220329-T00395
Please refer to the end of the specification for access instructions.

Lengthy table referenced here
US11287425-20220329-T00396
Please refer to the end of the specification for access instructions.

Lengthy table referenced here
US11287425-20220329-T00397
Please refer to the end of the specification for access instructions.

Lengthy table referenced here
US11287425-20220329-T00398
Please refer to the end of the specification for access instructions.

Lengthy table referenced here
US11287425-20220329-T00399
Please refer to the end of the specification for access instructions.

Lengthy table referenced here
US11287425-20220329-T00400
Please refer to the end of the specification for access instructions.

Lengthy table referenced here
US11287425-20220329-T00401
Please refer to the end of the specification for access instructions.

Lengthy table referenced here
US11287425-20220329-T00402
Please refer to the end of the specification for access instructions.

Lengthy table referenced here
US11287425-20220329-T00403
Please refer to the end of the specification for access instructions.

Lengthy table referenced here
US11287425-20220329-T00404
Please refer to the end of the specification for access instructions.

Lengthy table referenced here
US11287425-20220329-T00405
Please refer to the end of the specification for access instructions.

Lengthy table referenced here
US11287425-20220329-T00406
Please refer to the end of the specification for access instructions.

Lengthy table referenced here
US11287425-20220329-T00407
Please refer to the end of the specification for access instructions.

Lengthy table referenced here
US11287425-20220329-T00408
Please refer to the end of the specification for access instructions.

Lengthy table referenced here
US11287425-20220329-T00409
Please refer to the end of the specification for access instructions.

Lengthy table referenced here
US11287425-20220329-T00410
Please refer to the end of the specification for access instructions.

Lengthy table referenced here
US11287425-20220329-T00411
Please refer to the end of the specification for access instructions.

Lengthy table referenced here
US11287425-20220329-T00412
Please refer to the end of the specification for access instructions.

Lengthy table referenced here
US11287425-20220329-T00413
Please refer to the end of the specification for access instructions.

Lengthy table referenced here
US11287425-20220329-T00414
Please refer to the end of the specification for access instructions.

Lengthy table referenced here
US11287425-20220329-T00415
Please refer to the end of the specification for access instructions.

Lengthy table referenced here
US11287425-20220329-T00416
Please refer to the end of the specification for access instructions.

Lengthy table referenced here
US11287425-20220329-T00417
Please refer to the end of the specification for access instructions.

Lengthy table referenced here
US11287425-20220329-T00418
Please refer to the end of the specification for access instructions.

Lengthy table referenced here
US11287425-20220329-T00419
Please refer to the end of the specification for access instructions.

Lengthy table referenced here
US11287425-20220329-T00420
Please refer to the end of the specification for access instructions.

Lengthy table referenced here
US11287425-20220329-T00421
Please refer to the end of the specification for access instructions.

Lengthy table referenced here
US11287425-20220329-T00422
Please refer to the end of the specification for access instructions.

Lengthy table referenced here
US11287425-20220329-T00423
Please refer to the end of the specification for access instructions.

Lengthy table referenced here
US11287425-20220329-T00424
Please refer to the end of the specification for access instructions.

Lengthy table referenced here
US11287425-20220329-T00425
Please refer to the end of the specification for access instructions.

Lengthy table referenced here
US11287425-20220329-T00426
Please refer to the end of the specification for access instructions.

Lengthy table referenced here
US11287425-20220329-T00427
Please refer to the end of the specification for access instructions.

Lengthy table referenced here
US11287425-20220329-T00428
Please refer to the end of the specification for access instructions.

Lengthy table referenced here
US11287425-20220329-T00429
Please refer to the end of the specification for access instructions.

Lengthy table referenced here
US11287425-20220329-T00430
Please refer to the end of the specification for access instructions.

Lengthy table referenced here
US11287425-20220329-T00431
Please refer to the end of the specification for access instructions.

Lengthy table referenced here
US11287425-20220329-T00432
Please refer to the end of the specification for access instructions.

Lengthy table referenced here
US11287425-20220329-T00433
Please refer to the end of the specification for access instructions.

Lengthy table referenced here
US11287425-20220329-T00434
Please refer to the end of the specification for access instructions.

Lengthy table referenced here
US11287425-20220329-T00435
Please refer to the end of the specification for access instructions.

Lengthy table referenced here
US11287425-20220329-T00436
Please refer to the end of the specification for access instructions.

Lengthy table referenced here
US11287425-20220329-T00437
Please refer to the end of the specification for access instructions.

Lengthy table referenced here
US11287425-20220329-T00438
Please refer to the end of the specification for access instructions.

Lengthy table referenced here
US11287425-20220329-T00439
Please refer to the end of the specification for access instructions.

Lengthy table referenced here
US11287425-20220329-T00440
Please refer to the end of the specification for access instructions.

Lengthy table referenced here
US11287425-20220329-T00441
Please refer to the end of the specification for access instructions.

Lengthy table referenced here
US11287425-20220329-T00442
Please refer to the end of the specification for access instructions.

Lengthy table referenced here
US11287425-20220329-T00443
Please refer to the end of the specification for access instructions.

Lengthy table referenced here
US11287425-20220329-T00444
Please refer to the end of the specification for access instructions.

Lengthy table referenced here
US11287425-20220329-T00445
Please refer to the end of the specification for access instructions.

Lengthy table referenced here
US11287425-20220329-T00446
Please refer to the end of the specification for access instructions.

Lengthy table referenced here
US11287425-20220329-T00447
Please refer to the end of the specification for access instructions.

Lengthy table referenced here
US11287425-20220329-T00448
Please refer to the end of the specification for access instructions.

Lengthy table referenced here
US11287425-20220329-T00449
Please refer to the end of the specification for access instructions.

Lengthy table referenced here
US11287425-20220329-T00450
Please refer to the end of the specification for access instructions.

Lengthy table referenced here
US11287425-20220329-T00451
Please refer to the end of the specification for access instructions.

Lengthy table referenced here
US11287425-20220329-T00452
Please refer to the end of the specification for access instructions.

Lengthy table referenced here
US11287425-20220329-T00453
Please refer to the end of the specification for access instructions.

Lengthy table referenced here
US11287425-20220329-T00454
Please refer to the end of the specification for access instructions.

Lengthy table referenced here
US11287425-20220329-T00455
Please refer to the end of the specification for access instructions.

Lengthy table referenced here
US11287425-20220329-T00456
Please refer to the end of the specification for access instructions.

Lengthy table referenced here
US11287425-20220329-T00457
Please refer to the end of the specification for access instructions.

Lengthy table referenced here
US11287425-20220329-T00458
Please refer to the end of the specification for access instructions.

Lengthy table referenced here
US11287425-20220329-T00459
Please refer to the end of the specification for access instructions.

Lengthy table referenced here
US11287425-20220329-T00460
Please refer to the end of the specification for access instructions.

Lengthy table referenced here
US11287425-20220329-T00461
Please refer to the end of the specification for access instructions.

Lengthy table referenced here
US11287425-20220329-T00462
Please refer to the end of the specification for access instructions.

Lengthy table referenced here
US11287425-20220329-T00463
Please refer to the end of the specification for access instructions.

Lengthy table referenced here
US11287425-20220329-T00464
Please refer to the end of the specification for access instructions.

Lengthy table referenced here
US11287425-20220329-T00465
Please refer to the end of the specification for access instructions.

Lengthy table referenced here
US11287425-20220329-T00466
Please refer to the end of the specification for access instructions.

Lengthy table referenced here
US11287425-20220329-T00467
Please refer to the end of the specification for access instructions.

Lengthy table referenced here
US11287425-20220329-T00468
Please refer to the end of the specification for access instructions.

Lengthy table referenced here
US11287425-20220329-T00469
Please refer to the end of the specification for access instructions.

Lengthy table referenced here
US11287425-20220329-T00470
Please refer to the end of the specification for access instructions.

Lengthy table referenced here
US11287425-20220329-T00471
Please refer to the end of the specification for access instructions.

Lengthy table referenced here
US11287425-20220329-T00472
Please refer to the end of the specification for access instructions.

Lengthy table referenced here
US11287425-20220329-T00473
Please refer to the end of the specification for access instructions.

Lengthy table referenced here
US11287425-20220329-T00474
Please refer to the end of the specification for access instructions.

Lengthy table referenced here
US11287425-20220329-T00475
Please refer to the end of the specification for access instructions.

Lengthy table referenced here
US11287425-20220329-T00476
Please refer to the end of the specification for access instructions.

Lengthy table referenced here
US11287425-20220329-T00477
Please refer to the end of the specification for access instructions.

Lengthy table referenced here
US11287425-20220329-T00478
Please refer to the end of the specification for access instructions.

Lengthy table referenced here
US11287425-20220329-T00479
Please refer to the end of the specification for access instructions.

Lengthy table referenced here
US11287425-20220329-T00480
Please refer to the end of the specification for access instructions.

Lengthy table referenced here
US11287425-20220329-T00481
Please refer to the end of the specification for access instructions.

Lengthy table referenced here
US11287425-20220329-T00482
Please refer to the end of the specification for access instructions.

Lengthy table referenced here
US11287425-20220329-T00483
Please refer to the end of the specification for access instructions.

Lengthy table referenced here
US11287425-20220329-T00484
Please refer to the end of the specification for access instructions.

Lengthy table referenced here
US11287425-20220329-T00485
Please refer to the end of the specification for access instructions.

Lengthy table referenced here
US11287425-20220329-T00486
Please refer to the end of the specification for access instructions.

Lengthy table referenced here
US11287425-20220329-T00487
Please refer to the end of the specification for access instructions.

Lengthy table referenced here
US11287425-20220329-T00488
Please refer to the end of the specification for access instructions.

Lengthy table referenced here
US11287425-20220329-T00489
Please refer to the end of the specification for access instructions.

Lengthy table referenced here
US11287425-20220329-T00490
Please refer to the end of the specification for access instructions.

Lengthy table referenced here
US11287425-20220329-T00491
Please refer to the end of the specification for access instructions.

Lengthy table referenced here
US11287425-20220329-T00492
Please refer to the end of the specification for access instructions.

Lengthy table referenced here
US11287425-20220329-T00493
Please refer to the end of the specification for access instructions.

Lengthy table referenced here
US11287425-20220329-T00494
Please refer to the end of the specification for access instructions.

Lengthy table referenced here
US11287425-20220329-T00495
Please refer to the end of the specification for access instructions.

Lengthy table referenced here
US11287425-20220329-T00496
Please refer to the end of the specification for access instructions.

Lengthy table referenced here
US11287425-20220329-T00497
Please refer to the end of the specification for access instructions.

Lengthy table referenced here
US11287425-20220329-T00498
Please refer to the end of the specification for access instructions.

Lengthy table referenced here
US11287425-20220329-T00499
Please refer to the end of the specification for access instructions.

Lengthy table referenced here
US11287425-20220329-T00500
Please refer to the end of the specification for access instructions.

Lengthy table referenced here
US11287425-20220329-T00501
Please refer to the end of the specification for access instructions.

Lengthy table referenced here
US11287425-20220329-T00502
Please refer to the end of the specification for access instructions.

Lengthy table referenced here
US11287425-20220329-T00503
Please refer to the end of the specification for access instructions.

Lengthy table referenced here
US11287425-20220329-T00504
Please refer to the end of the specification for access instructions.

Lengthy table referenced here
US11287425-20220329-T00505
Please refer to the end of the specification for access instructions.

Lengthy table referenced here
US11287425-20220329-T00506
Please refer to the end of the specification for access instructions.

Lengthy table referenced here
US11287425-20220329-T00507
Please refer to the end of the specification for access instructions.

Lengthy table referenced here
US11287425-20220329-T00508
Please refer to the end of the specification for access instructions.

Lengthy table referenced here
US11287425-20220329-T00509
Please refer to the end of the specification for access instructions.

Lengthy table referenced here
US11287425-20220329-T00510
Please refer to the end of the specification for access instructions.

Lengthy table referenced here
US11287425-20220329-T00511
Please refer to the end of the specification for access instructions.

Lengthy table referenced here

US11287425-20220329-T00512

Please refer to the end of the specification for access instructions.

Lengthy table referenced here

US11287425-20220329-T00513

Please refer to the end of the specification for access instructions.

Lengthy table referenced here

US11287425-20220329-T00514

Please refer to the end of the specification for access instructions.

Lengthy table referenced here

US11287425-20220329-T00515

Please refer to the end of the specification for access instructions.

Lengthy table referenced here

US11287425-20220329-T00516

Please refer to the end of the specification for access instructions.

Lengthy table referenced here

US11287425-20220329-T00517

Please refer to the end of the specification for access instructions.

Lengthy table referenced here

US11287425-20220329-T00518

Please refer to the end of the specification for access instructions.

Lengthy table referenced here

US11287425-20220329-T00519

Please refer to the end of the specification for access instructions.

Lengthy table referenced here

US11287425-20220329-T00520

Please refer to the end of the specification for access instructions.

Lengthy table referenced here

US11287425-20220329-T00521

Please refer to the end of the specification for access instructions.

Lengthy table referenced here

US11287425-20220329-T00522

Please refer to the end of the specification for access instructions.

Lengthy table referenced here

US11287425-20220329-T00523

Please refer to the end of the specification for access instructions.

Lengthy table referenced here

US11287425-20220329-T00524

Please refer to the end of the specification for access instructions.

Lengthy table referenced here

US11287425-20220329-T00525

Please refer to the end of the specification for access instructions.

Lengthy table referenced here

US11287425-20220329-T00526

Please refer to the end of the specification for access instructions.

Lengthy table referenced here

US11287425-20220329-T00527

Please refer to the end of the specification for access instructions.

Lengthy table referenced here

US11287425-20220329-T00528

Please refer to the end of the specification for access instructions.

LENGTHY TABLES

The patent contains a lengthy table section. A copy of the table is available in electronic form from the USPTO web site (https://seqdata.uspto.gov/?pageRequest=docDetail&DocID=US11287425B2). An electronic copy of the table will also be available from the USPTO upon request and payment of the fee set forth in 37 CFR 1.19(b)(3).

What is claimed is:

1. A method for detecting the presence of a single nucleotide polymorphism (SNP) in genetic material from a human female subject having endometriosis, the method comprising: detecting one or more A alleles at SNP rs17265665 in the genetic material, wherein detecting comprises performing: DNA sequencing, hybridization with a complementary probe, an oligonucleotide ligation assay, a PCR based assay, or any combination thereof.

2. The method of claim 1, further comprising detecting one or more G alleles at SNP rs7629235.

3. The method of claim 1, wherein said method further comprises recording at least one endometriosis related clinical factor of said human female subject, wherein said endometriosis related clinical factor comprises age at menarche, body mass index (BMI), pelvic pain, infertility, or any combination thereof.

4. The method of claim 1, wherein said method further comprises administering to said human female subject a therapeutic agent, wherein said therapeutic agent at least partially compensates for said endometriosis.

5. The method of claim 1, wherein said human female subject is a fetus.

6. The method of claim 1, further comprising detecting one or more A alleles at SNP rs6804141.

7. The method of claim 1, further comprising detecting one or more T alleles at SNP rs1010146.

8. The method of claim 1, further comprising detecting one or more A alleles at SNP rs17594526.

9. The method of claim 1, wherein the genetic material comprises a tissue sample.

* * * * *